(12) United States Patent
Chekalyuk

(10) Patent No.: US 8,970,841 B2
(45) Date of Patent: Mar. 3, 2015

(54) SPECTRAL AND TEMPORAL LASER FLUORESCENCE ANALYSIS SUCH AS FOR NATURAL AQUATIC ENVIRONMENTS

(75) Inventor: Alexander Chekalyuk, Bridgewater, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 141 days.

(21) Appl. No.: 13/513,786

(22) PCT Filed: Dec. 3, 2010

(86) PCT No.: PCT/US2010/058891
§ 371 (c)(1),
(2), (4) Date: Sep. 11, 2012

(87) PCT Pub. No.: WO2011/069067
PCT Pub. Date: Jun. 9, 2011

(65) Prior Publication Data
US 2012/0324986 A1 Dec. 27, 2012

Related U.S. Application Data

(60) Provisional application No. 61/266,756, filed on Dec. 4, 2009.

(51) Int. Cl.
*G01J 3/30* (2006.01)
*G01J 3/28* (2006.01)
(Continued)

(52) U.S. Cl.
CPC ............... *G01N 21/6408* (2013.01); *G01J 3/02* (2013.01); *G01J 3/0264* (2013.01); *G01J 3/4406* (2013.01);
(Continued)

(58) Field of Classification Search
None
See application file for complete search history.

(56) References Cited

U.S. PATENT DOCUMENTS

| 4,084,905 A | 4/1978 | Schreiber et al. |
| 4,293,225 A | 10/1981 | Wheaton et al. |

(Continued)

FOREIGN PATENT DOCUMENTS

| CN | 102753959 A | 10/2012 |
| WO | WO-2010058891 A1 | 5/2010 |
| WO | WO-2011069067 A1 | 6/2011 |

OTHER PUBLICATIONS

"CICEET Progress Report for the period Sep. 15, 2004 Through Mar. 15, 2005; dvanced Laser Fluorescence (ALF) Technology for Estuarine and Coastal Environmental Biomonitoring", http://ciceet.unh.edu/progressreports/2005/3_2005/chekalyuk2003/, 6 pgs.

(Continued)

*Primary Examiner* — Kara E Geisel
*Assistant Examiner* — Hina F Ayub
(74) *Attorney, Agent, or Firm* — Schwegman Lundberg & Woessner, P.A.

(57) ABSTRACT

An Advanced Laser Fluorometer (ALF) can combine spectrally and temporally resolved measurements of laser-stimulated emission (LSE) for characterization of dissolved and particulate matter, including fluorescence constituents, in liquids. Spectral deconvolution (SDC) analysis of LSE spectral measurements can accurately retrieve information about individual fluorescent bands, such as can be attributed to chlorophyll-a (Chl-a), phycobiliprotein (PBP) pigments, or chromophoric dissolved organic matter (CDOM), among others. Improved physiological assessments of photosynthesizing organisms can use SDC analysis and temporal LSE measurements to assess variable fluorescence corrected for SDC-retrieved background fluorescence. Fluorescence assessments of Chl-a concentration based on LSE spectral measurements can be improved using photo-physiological information from temporal measurements. Quantitative assessments of PBP pigments, CDOM, and other fluorescent constituents, as well as basic structural characterizations of photosynthesizing populations, can be performed using SDC analysis of LSE spectral measurements.

25 Claims, 23 Drawing Sheets

(51) Int. Cl.
| | |
|---|---|
| *G01N 21/25* | (2006.01) |
| *G01N 21/64* | (2006.01) |
| *G01J 3/02* | (2006.01) |
| *G01J 3/44* | (2006.01) |
| *G01N 21/65* | (2006.01) |
| *G01N 21/63* | (2006.01) |

(52) U.S. Cl.
CPC ............ *G01N 21/6486* (2013.01); *G01N 21/65* (2013.01); *G01N 2021/635* (2013.01); *G01N 2021/6419* (2013.01)
USPC ............ 356/326; 356/317; 356/318; 356/417

(56) References Cited

U.S. PATENT DOCUMENTS

| | | |
|---|---|---|
| 4,542,104 A | 9/1985 | Stryer et al. |
| 4,942,303 A | 7/1990 | Kolber et al. |
| 5,422,719 A | 6/1995 | Goldstein |
| 5,426,306 A | 6/1995 | Kolber et al. |
| 6,121,053 A | 9/2000 | Kolber et al. |
| 7,209,223 B1 | 4/2007 | Hull et al. |
| 7,236,248 B2 | 6/2007 | Kirkpatrick et al. |
| 7,301,158 B1 | 11/2007 | Hoang |
| 7,474,400 B2 | 1/2009 | Tartakovsky |
| 2003/0134325 A1 | 7/2003 | Cubicciotti |
| 2008/0035858 A1 | 2/2008 | Hegazi |
| 2009/0173892 A1 | 7/2009 | Courtney et al. |

OTHER PUBLICATIONS

"International Application Serial No. PCT/US2010/058891, Search Report mailed Feb. 22, 2011", 2.

"International Application Serial No. PCT/US2010/058891, Written opinion mailed Feb. 22, 2011", 6.

Chekalyuk, A M, et al., "Pump-During-Probe Fluorometry of Phytoplankton: Group-Specific Photosynthetic Characteristics From Individual Cell Analysis", SPIE vol. 2963, 840-845.

Chekalyuk, Alexander M, et al., "Advanced Laser Fluorescence (ALF) Technology for Estuarine and Coastal Environmental Biomonitoring", A Final Report Submitted to the NOAA/UNH Cooperative Institute for Coastal and Estuarine Environmental Technology (CICEET), (Mar. 31, 2006), 23 pgs.

Chekalyuk, Alexander M, et al., "Laser fluorescence analysis of phytoplankton across a frontal zone in the California Current ecosystem", Journal of Plankton Research, 2012, Retrieved from the Internet: <http://plankt.oxfordjournals.org/content/early/2012/05/16/plankt.fbs034.full.pdf>, (2012), 17 pgs.

Chekalyuk, Alexander, et al., "Photo-physiological variability in phytoplankton chlorophyll fluorescence and assessment of chlorophyll concentration", Optics Express vol. 19, No. 23, (Nov. 7, 2011), 22643-22658.

Chekalyuk,, A, "Advanced laser fluorometry of natural aquatic environments", URL:http://www.aslo.org/lomethods/free/2008/0591.pdf, (Dec. 1, 2008), 591-609.

Olson, R, "Photosynthetic Characteristics of Marine Phytoplankton from Pump-During-Probe Fluorometry of Individual Cells at Sea", http://www.whoi.edulcmslfiles/Olson_etaLCytometry1999_58518.pdf, (Sep. 1999), 1-13.

Olson, Robert J, et al., "Phytoplankton Photosynthetic Characteristics from Fluorescence Induction Assays of Individual Cells", Limnology and Oceanography, vol. 41, No. 6. (Sep. 1996), pp. 1253-1263, (Sep. 1996), 1253-1263.

Zabriskie, D W, et al., "Estimation of Fermentation Biomass Concentration by Measuring Culture Fluorescence", Applied and Environmental Microbiology 35(2), (Feb. 1798), 337-343.

"International Application Serial No. PCT/US2010/058891, International Preliminary Report on Patentabiliy mailed Jun. 14, 2012", 8 pgs.

Chinese Application Serial No. 201080063201.6, Office Action mailed Dec. 27, 2013, w/English translation, 19 pgs.

Chinese Application Serial No. 201080063201.6, Response filed Jul. 10, 2014 to Office Action mailed, w/English claims, 15 pgs.

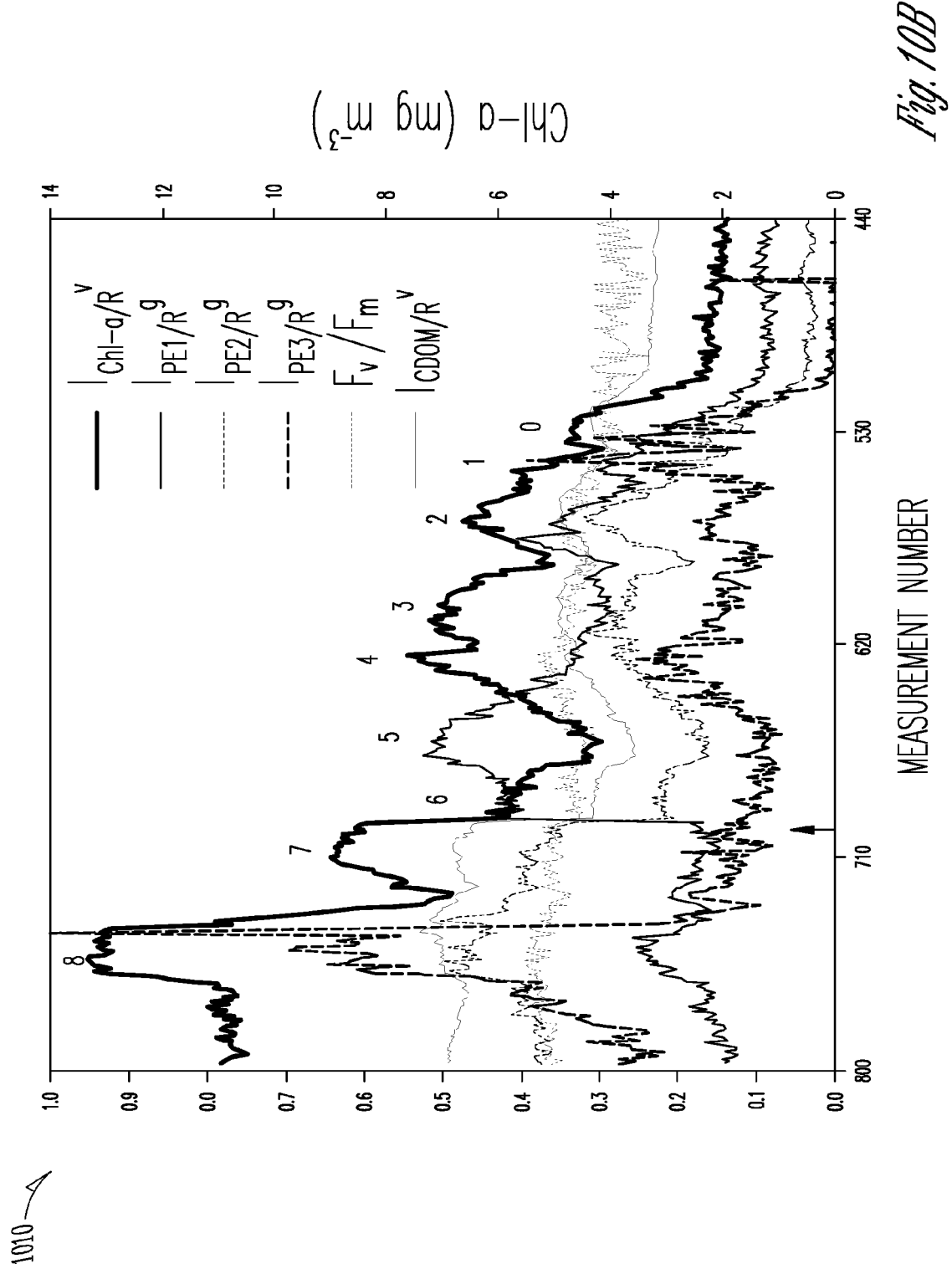

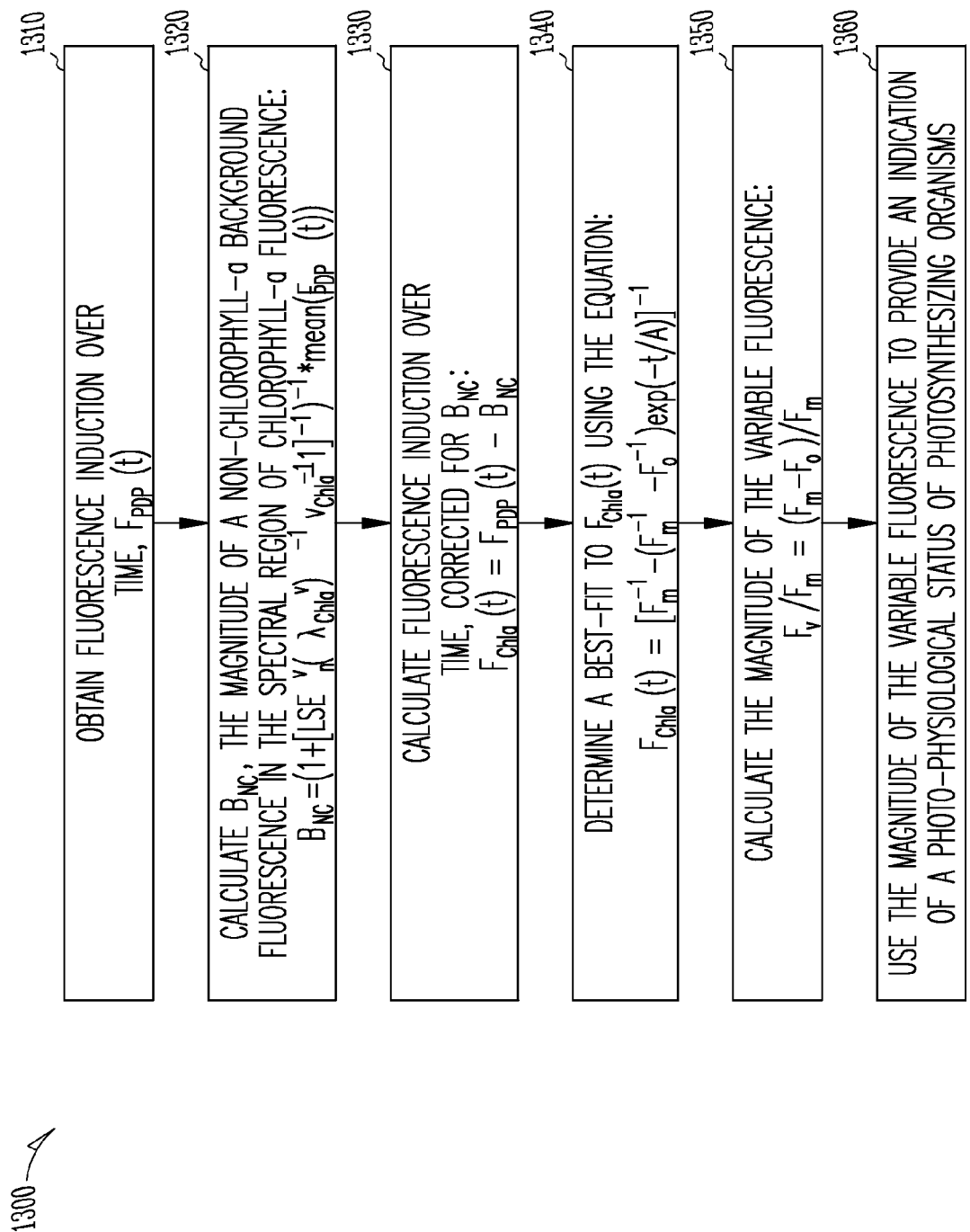

SPECTRAL AND TEMPORAL LASER FLUORESCENCE ANALYSIS SUCH AS FOR NATURAL AQUATIC ENVIRONMENTS

CLAIM OF PRIORITY

This application is a nationalization under 35 U.S.C. §371 from International Application Serial No. PCT/US2010/058891, filed Dec. 3, 2010, and published as WO2011/069067 on Jun. 9, 2011, which claims the benefit of priority of Chekalyuk U.S. Provisional Patent Application Ser. No. 61/266,756, entitled ANALYSIS OF FLUORESCENT AQUATIC CONSTITUENTS USING SPECTRAL DECONVOLUTION AND INDUCTION OF LASER-STIMULATED EMISSION, filed on Dec. 4, 2009, the contents of which applications and publication are hereby incorporated by reference herein in their entirety.

STATEMENT REGARDING FEDERALLY SPONSORED RESEARCH DEVELOPMENT

This invention was made with government support under award number OCE-07-24561 from NSF (Ocean Technology and Interdisciplinary Coordination Program), under award number NNX07AN44G from NASA (Ocean Biology and Biogeochemistry program), and under award number NA03NOS4190195 from NOAA/UNH (Cooperative Institute for Coastal and Estuarine Environment Technology. The government has certain rights in this invention.

BACKGROUND

Fluorescence analysis of natural aquatic environments, such as including oceanic, estuarine, or fresh waters, can be based on measurements of water emission, such as in response to a laser, LED, Xenon flash tube, or other sources of fluorescence excitation. Fluorescence analysis can be used to retrieve information about the fluorescent constituents in a water body or sample. For example, in vivo fluorescence of chlorophyll-a (Chl-a) and accessory phycobiliprotein (PBP) pigments can be broadly used as an index of phytoplankton biomass, and can provide useful information for structural or photo-physiological characterization of mixed algal populations. A broadband chromophoric dissolved organic matter (CDOM) fluorescence emission can be used to assess CDOM abundance, or to assess qualitative characteristics of CDOM.

There can be significant spectral complexity of the actively stimulated emission of natural waters. This can be due to an overlap between water Raman (WR) scattering and the fluorescence bands of aquatic constituents. Most commercially available field fluorometers use spectrally broad excitation sources and relatively narrow band emission detection, and often do not provide adequate spectral resolution to ensure reliable assessment of fluorescent constituents in spectrally complex natural waters.

Spectral measurements of water emission can be performed, such as using a plurality of light excitation sources, wherein at least one excitation source can have a wavelength that is different from other sources. Fluorescence and absorbance characteristics, such as over a plurality of wavelengths, can be detected. Hull et al., in U.S. Pat. No. 7,209,223, entitled OPTICAL DEVICE FOR MEASURING OPTICAL PROPERTIES OF A SAMPLE AND METHOD RELATING THERETO, refers to detecting a continuous, broadband spectrum of emission wavelengths, and a signal interpretation system to interpret a continuous fluorescence emission spectrum. Kolber et al., in U.S. Pat. No. 6,121,053, entitled MULTIPLE PROTOCOL FLUOROMETER AND METHOD, refers to measuring spectrally-resolved variable fluorescence components, among other functional and optical characteristics of phytoplankton and other plants.

Temporally-resolved measurements of water emission can be performed, such as using a light source, a cut-off filter, and photo-detector. Schrieber et al., in U.S. Pat. No. 4,084,905, entitled APPARATUS FOR DETECTING AND MEASURING FLUORESCENCE EMISSION, refers to detecting and measuring a time course of fluorescence, including using an initial fluorescence yield to measure chlorophyll concentrations.

OVERVIEW

Advanced laser fluorometry can provide spectral deconvolution (SDC) analysis of laser-stimulated emission (LSE) of a liquid which includes dissolved and particulate matter. In an example, the liquid can include a natural water sample including fluorescent constituents. Laser excitation, such as at 405 or 532 nm, can be used for assessment of chlorophyll-a, phycoerythrin, and chromophoric dissolved organic matter (CDOM), among other liquid or aquatic constituents. The Advanced Laser Fluorometer (ALF) instrument can obtain spectrally-resolved measurements of LSE from a water sample and temporally-resolved measurements of LSE induction from the same water sample. The ALF can be used to compute a characteristic of one or more fluorescent substances in the water sample, such as a quantitative or physiological characteristic. In an example, computing a characteristic of a fluorescent substance can include using information from one of the spectrally-resolved or temporally-resolved measurements to adjust the other of the spectrally-resolved or temporally-resolved measurement.

Active fluorescence analysis of natural aquatic environments, such as including oceanic, estuarine, or fresh waters, can be based on measurements of LSE from water, such as to retrieve qualitative and quantitative information about the in-situ fluorescent constituents. For example, in vivo fluorescence of Chl-a and PBP pigments can be used as an index of phytoplankton biomass and can provide useful information for structural or photo-physiological characterization of mixed algal populations. A broadband CDOM fluorescence emission can be used for assessment of CDOM abundance and its qualitative characterization.

There can be significant spectral complexity of the actively excited emission of liquids. In an example including a water volume, the spectral complexity can be due to overlap between water Raman (WR) scattering and the fluorescence bands associated with various aquatic constituents. Not accounting for the spectral complexity can lead to severe problems in interpreting fluorescence measurements, and can compromise the accuracy of the fluorescence assessments. To address this issue, one approach can be (i) to use blue and green narrow-band laser excitation to selectively stimulate the constituent fluorescence and simplify the overlapped spectral patterns, (ii) to conduct broadband spectral measurements of laser-stimulated emission (LSE), and (iii) to use spectral deconvolution analysis of the LSE signatures to retrieve information about the aquatic fluorescent constituents from their overlapped spectral patterns. Some of these principles, such as multi-wavelength LSE excitation or broadband spectral detection, can be implemented, such as in shipboard or airborne laser fluorosensors. Nonetheless, most commercially available field fluorometers use spectrally broad fluorescence excitation, and do not provide adequate spectral resolution to ensure reliable assessment of the fluorescent constituents in spectrally complex natural waters.

The present inventor has recognized, among other things, that a problem to be solved can include improving the accuracy of analysis of fluorescent constituents in liquids using spectrally-resolved or temporally-resolved active fluorescence measurements of liquids, such as to provide a quantitative or qualitative assessment of liquid constituents or their physiological status. In an example, the present subject matter can provide a solution to this problem, such as using advanced laser fluorometry methods and measurement techniques embodied in a new field instrument, the Advanced Laser Fluorometer (ALF). The ALF instrument can be capable of fast, broadband, flow-through LSE spectral measurements or photo-physiological assessments of phytoplankton. An analytical technique, spectral deconvolution (SDC) has been developed and integrated with the ALF instrument. The SDC technique can allow for real-time assessments or characterization of key liquid constituents, such as CDOM, Chl-a, or PBP pigments, among others. Such real-time assessments or characterization can be carried out in a broad range of environments, including natural aquatic environments. The SDC analysis can be integrated with measurements of variable fluorescence, $F_v/F_m$, corrected for the SDC-retrieved non-chlorophyll background fluorescence, $B_{NC}$, to improve photo-physiological assessments of photosynthesizing microorganisms.

The ALF instrument can be a portable instrument that can provide underway flow-through measurements or discrete sample analysis, such as in one or more various shipboard or stationary settings (see, e.g., FIGS. 1A and 1B). ALF deployments in diverse water types, such as in the Atlantic or Pacific Oceans, Chesapeake, Del. or Monterey Bays, or in a number of estuaries and rivers, revealed significant spectral complexity of natural waters, which can be analyzed using the broadband SDC analysis described herein. For example, ALF deployments in the Atlantic and Pacific Oceans, Chesapeake, Del. and Monterey Bays revealed significant spectral complexity of LSE. Considerable variability in chlorophyll-a fluorescence peak, 673-685 nm, was detected. High correlation ($R^2=0.93$) was observed in diverse water types between chlorophyll-a concentration and fluorescence normalized to water Raman scattering. Four unidentified red bands, peaking at 615, 625, 644 and 662 nm, were detected in the LSE excited at 405 nm. Significant variability in the $B_{NC}$/chlorophyll-a ratio was observed in diverse waters. Examples of the ALF spectral correction of $F_v/F_m$, underway shipboard measurements of horizontal variability, and vertical distributions compiled from the discrete samples analyses are presented. The field deployments have demonstrated the utility of the ALF technique as an integrated tool for research and observations.

The SDC analytical technique described herein was developed at least in part on the basis of laboratory and field measurements. These can be used to retrieve from the LSE signatures the individual spectral bands of liquid constituents for their qualitative and quantitative assessment, and can provide for spectral correction of the variable fluorescence measurements integrated with the SDC retrievals. Initial experimental field measurements have demonstrated the utility of the ALF/SDC analytical suite as an informative integrated tool for research and bioenvironmental monitoring.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 10A and 10B illustrate an example of the shipboard underway ALF measurements.

FIG. 13 illustrates generally an example that can include using information from a spectrally-resolved measurement to improve an assessment based on a temporally-resolved measurement.

DETAILED DESCRIPTION

This document describes, among other things, an Advanced Laser Fluorometer (ALF) that can combine spectrally and temporally resolved measurements of laser-stimulated emission (LSE) such as for characterization of dissolved and particulate matter, including fluorescence constituents, in liquids. Spectral deconvolution (SDC) analysis of LSE spectral measurements can accurately retrieve information about individual fluorescent bands, such as can be attributed to chlorophyll-a (Chl-a), phycobiliprotein (PBP) pigments, or chromophoric dissolved organic matter (CDOM), among others. Improved physiological assessments of photosynthesizing organisms can use SDC analysis and temporal LSE measurements to assess variable fluorescence corrected for SDC-retrieved background fluorescence. Fluorescence assessments of Chl-a concentration based on LSE spectral measurements can be improved using photo-physiological information from temporal measurements. Quantitative assessments of PBP pigments, CDOM, and other fluorescent constituents, as well as basic structural characterizations of photosynthesizing populations, can be performed using SDC analysis of LSE spectral measurements.

Examples of Materials and Procedures
Advanced Laser Fluorometer

Figure 2:
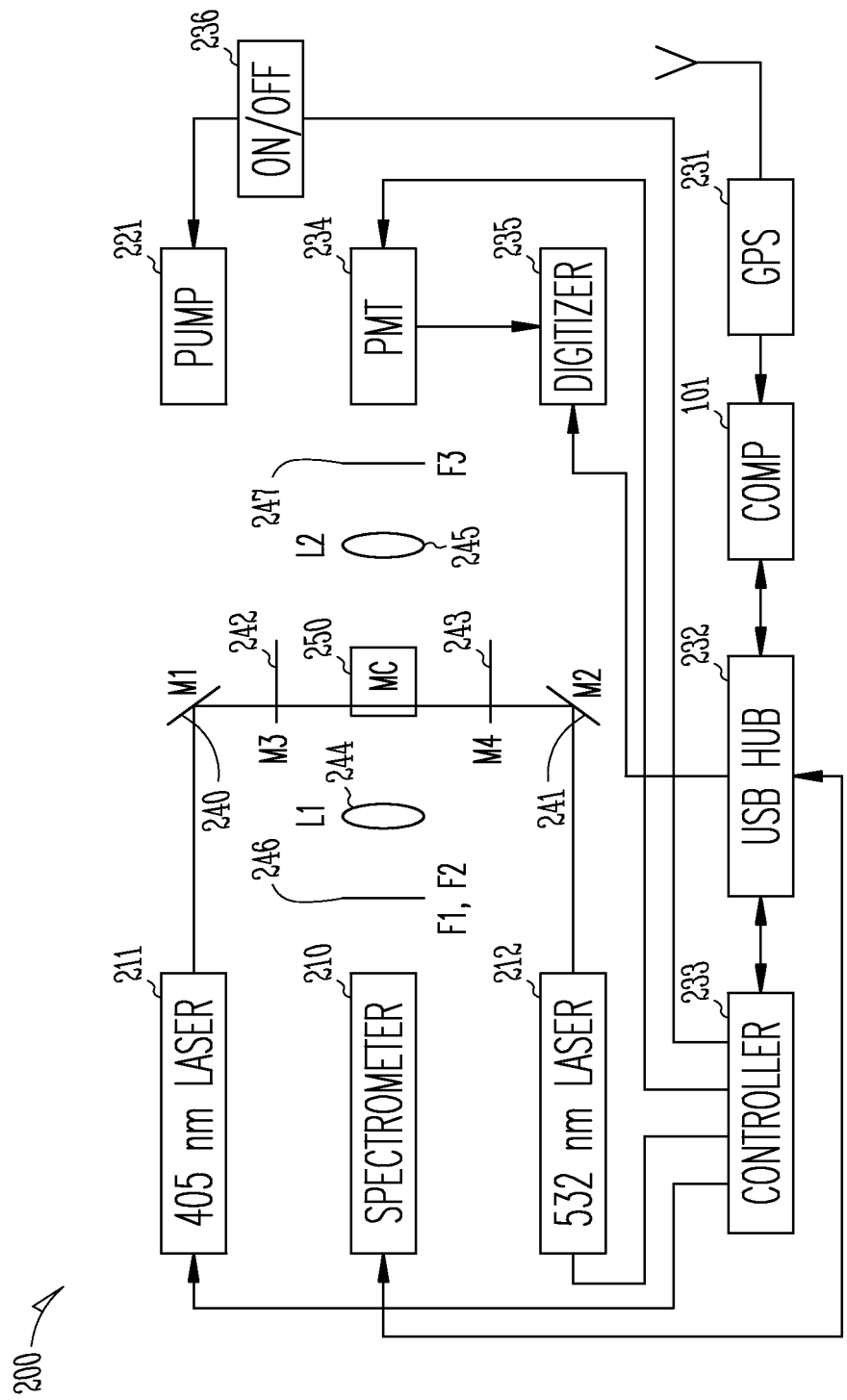
FIG. 2 illustrates generally a block diagram of the ALF instrument.

FIG. 2 illustrates a diagram of an example of an ALF instrument configuration. Emission of a violet or blue laser 211 (e.g., 50 mW at 405 nm; Power Technology) or green laser 212 (e.g., 50 mW at 532 nm; World Star Tech) can be alternatively directed, such as via steering mirrors M1 240, and M2 241, in a water sample, such as can be pumped through a glass measurement cell MC 250 (e.g., RF-1010-f, Spectrocell). In an example, dichroic mirrors, M3 242 and M4 243, (e.g., 430ASP and 505ALP, Omega Optical) can be used to reflect laser beams back to the measurement cell MC 250, such as to increase the signal intensity. The LSE can be collected, such as with a lens L1 244 (e.g., f=25 mm; 25 mm diam.). The collected LSE can be directed through a collimating lens and 0.6 mm optical fiber to an input slit of a spectrometer 210 (e.g., BTC111, B&WTek, Inc.) that can be configured to measure the LSE spectrum, such as in the 380-808 nm range (e.g., 2048 pixels). In an example, the spectrometer 210 can include a first measurement circuit, such as can be configured to obtain a spectral measurement of LSE. In an example, the spectrometer 210 can include a second measurement circuit, such as can be configured to obtain a temporal measurement of LSE induction.

In an example, long-pass and notch filters F1 and F2 246 (e.g., 420ALP, Omega Optical, and RNF-532.0, CVI Laser) can serve to reduce laser-induced elastic scattering in the analyzed LSE spectra. To conduct temporally-resolved measurements of emission from the analyzed water, one or more laser flashes can be used to stimulate the sample. Emission can be measured using light collection and filtration optics, a photosensor, and a waveform digitizer. In an example, temporal pump-during-probe (PDP) measurements, such as of Chl-a fluorescence induction, can be stimulated with 200 µs PDP flashes of a 405 nm laser, which can be TTL-modulated such as at a 5 Hz repetition rate. The laser can be appropriately focused in a water sample such as to ensure the Chl-a fluorescence induction occurs over a single-turnover, i.e., sub-100 µs time scale. A sample flow rate such as 100 ml/min can help to promote or ensure assaying the low-light adapted phytoplankton cells with individual PDP laser flashes. In an example, a sensor for temporally-resolved measurements can include an LSE-collection system, such as a lens L2 245 (e.g., f=25 mm; 25 mm diam.), a band-pass interference filter F3 247 (e.g., 685.0-10-75, Intor), and a photomultiplier sensor, PMT 234 (e.g., H7710-02, Hamamatsu), and a waveform digitizer 235 such as a 20 MHz 12 bit oscilloscope USB board (e.g., 3224, Pico Technology). In an example, the waveform digitizer 235 can include a second measurement circuit that can be configured to obtain temporally-resolved measurements of LSE.

Figure 1A:
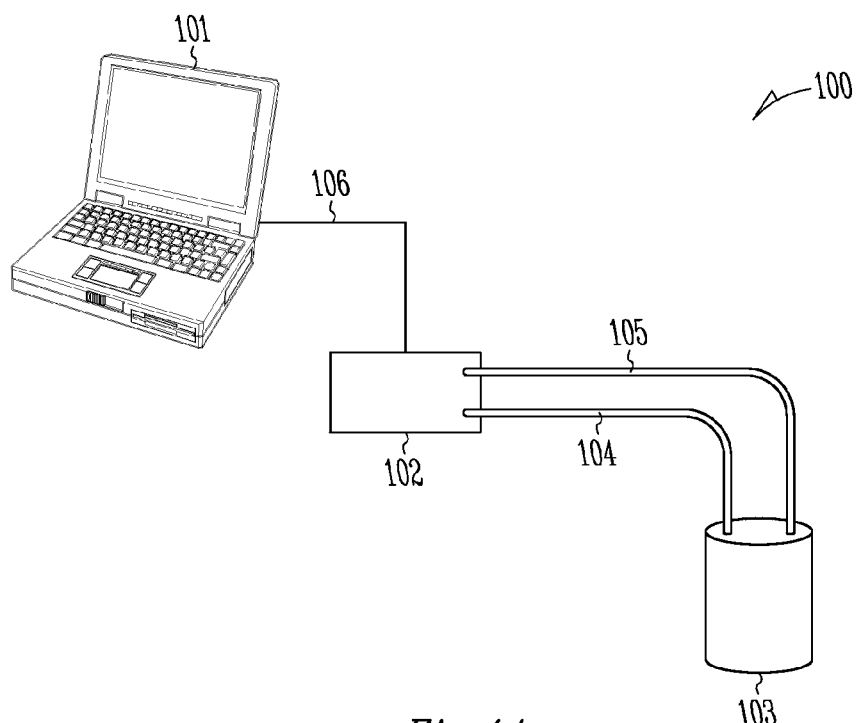
FIG. 1A illustrates generally the Advanced Laser Fluorometer (ALF) configured for the laboratory sample analysis.
Figure 1B:
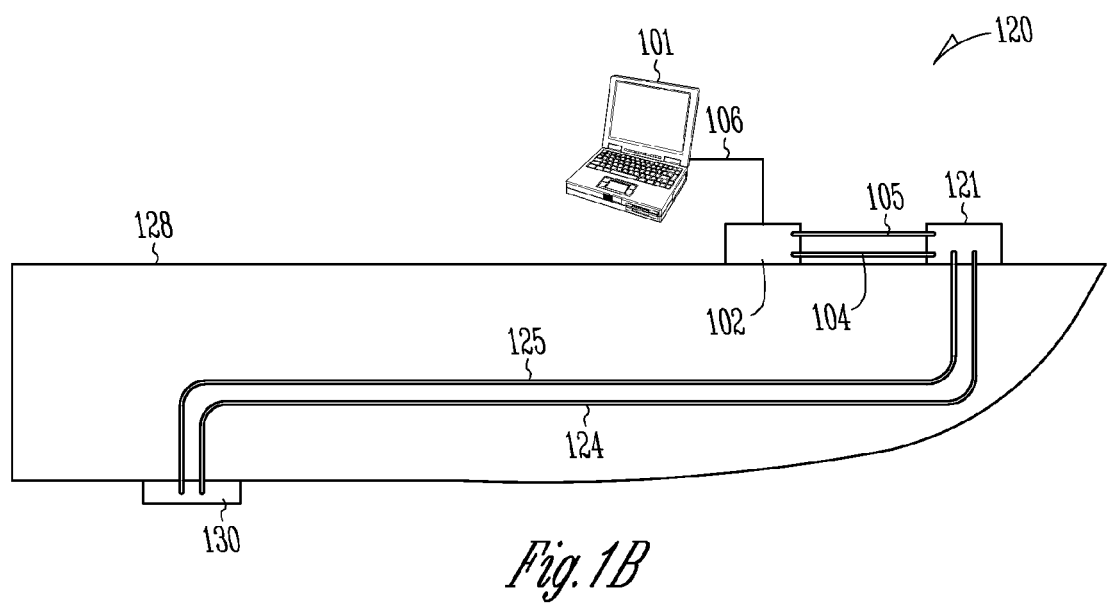
FIG. 1B illustrates generally the Advance Laser Fluorometer (ALF) configured for flow-through underway measurements onboard a motorboat.
Figure 3:
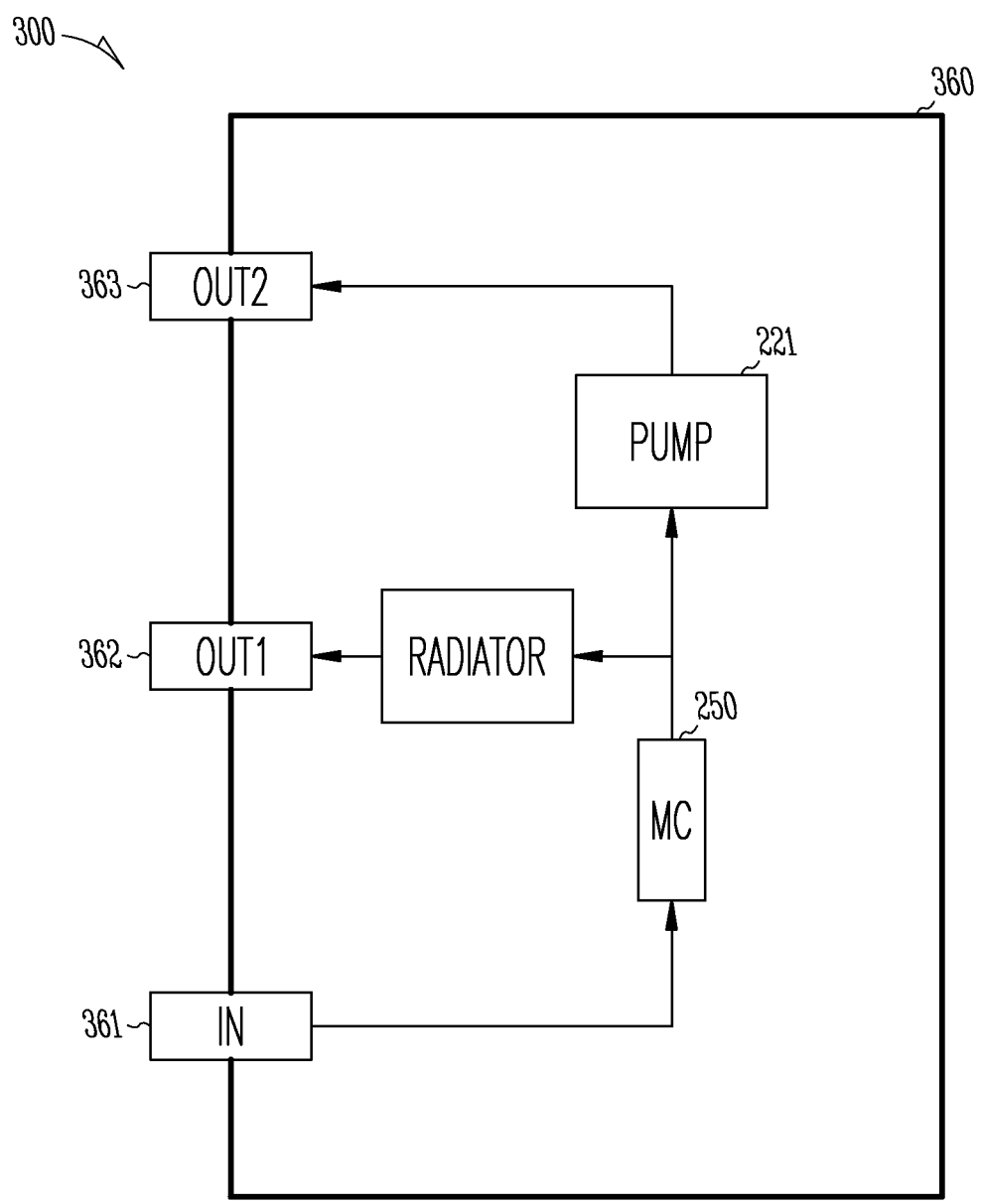
FIG. 3 illustrates generally a possible design of the ALF sampling system.

FIG. 3 illustrates a diagram of an example of an ALF sampling system. In an example, the ALF sampling system can be used to provide flow-through measurements, such as using both external (e.g., from a shipboard water sampling system to conduct the underway measurements) and internal (e.g., for discrete sample analysis) pumping of the analyzed water through the measurement cell. In an example, three auto-locking water connectors, such as In 361, Out1 362, and Out2 363 (e.g., PLCD16004B5, Colder Products), can provide inflow and outflow of the sampled water such as via tubes, such as silicone tubes (e.g., Nalgene 8060-0030) (see, for example, FIG. 1B at 104, 105, 124, 125). During underway measurements, such as using an underway measurement device 130 coupled to a boat 128, water flow, supplied by the shipboard sampling pump 221, can pass through the input water connector, such as In 361, into the bottom of a measurement cell MC 250. After measurements have been taken, the water can pass to the discharge connector, such as Out1 362, such as via a radiator 364 (e.g., HWLabs) with a fan for heat removal from the sealed instrument case. An external sampling pump, such as a battery-operated peristaltic pump 121 (e.g., MasterFlex 07571-00, Cole-Parmer; see FIG. 1B), can be used for the ALF deployments on small boats. In an example, an ALF instrument can be used for flow-through underway shipboard measurements, monitoring at a stationary setting (e.g., docks, piers, platforms, etc.) or for discrete sample analyses. In the latter case, a sample bottle can be connected to the input water connector In 361 (see, e.g., FIG. 3). An instrument pump, such as a miniature diaphragm pump (e.g., NF11 KPDC, KNF Neuberger) inside the ALF instrument, can provide water flow, such as through a measurement cell MC 250, to the sample discharge connector, Out2 363. The water can be drained to the sink or returned back to the sample bottle for sample circulation. A sample bottle 103, such as a dark glass bottle of 100-500 ml (e.g., 141-0500, I-Chem), can be used for the measurements.

A multifunction USB controller board 233 (e.g., U12, LabJack, see FIG. 2) can be used to control and interface several instrument components. The lasers 211, 212 and the pump 221 can be controlled via outputs of the USB controller board 233; a relay power switch 236 (e.g., 70M-ODC5, Grayhill), controlled via outputs of the USB controller 233, can also be used to switch the pump 221 on or off. The PMT 234 gain can be controlled via the USB controller board 233. Additional sensors, such as a temperature sensor (e.g., E11022, LabJack) to monitor the temperature inside the instrument case, can be connected to the inputs of USB controller board 233. An external or internal computer, Comp 101, such as a rugged notebook computer (e.g., Toughbook 52, Panasonic) can communicate with the USB controller board 233, the spectrometer 210, and the digitizer 235, such as via a USB cable and a USB hub 232, such as internal to the ALF instrument. In an example, Comp 101 can include a processor circuit, such as can be coupled to the first or second measurement circuits. In an example, the processor circuit can be configured to compute or record characteristics of fluorescent constituents in a water sample using information from the first or second measurement circuits.

A compact GPS system 231 (e.g., 76S with GA 29 antenna, Garmin) can be communicatively coupled to the Comp 101, and can be configured for use during shipboard underway measurements, such as to provide time or location information that can be saved along with recorded measurement data. In an example, the ALF instrument components can be powered using 14-19 VDC power can be provided by either an internal or external AC adapter or rechargeable battery. For example, a 160 VAH battery (e.g., PowerPad, 160 Electrovaya), enclosed with the ALF instrument in, for example, a waterproof Pelican case, can be used for approximately 4.5 hours of measurements on small boats (see FIG. 1B) or in stationary settings (see FIG. 1A).

In an example, ALF operational software can be configured to use the LabView instrument control package from National Instruments, among other instrument control packages. Each measurement cycle can include three sequent sub-cycles, such as to measure (i) the $LSE^v$ spectrum with a blue or violet (e.g., 405 nm) excitation, (ii) the $LSE^g$ spectrum with a green (e.g., 532 nm) excitation, and (iii) the fluorescence induction stimulated at 405 nm. (The superscripts "v" and "g" here and below stand for the violet/blue and green excitation, respectively). In an example, an operator can preset the LSE spectral integration time (typically, 0.3 to 3 s), the PMT gain, the duration of the PDP actinic flashes and their repetition rate, and the number of acquisitions (e.g., 5-25), such as to average the fluorescence induction, such as to optimize the volume sampled during the measurement, as well as the spectral S/N ratio. The duration of the ALF measurement cycle can vary, such as in a 5-25 second range. The measurement parameters can be automatically adjusted with regard to the signal variability; the SDC and PDP data can be analyzed and displayed in real time (along with the GPS data during the shipboard measurements), and stored on the computer along with GPS data and screen captures that can be useful for documentation or data analysis. The discrete sample measurement can begin with an automatic filling of the measurement cell MC 250 with sampled water using the ALF pump 221. The measurement cell MC 250 can be monitored via the time course of CDOM and Chl-a fluorescence. In an example, a particular sample measurement can include 5 to 15 measurement cycles.

Spectral Deconvolution Components

SDC analyses of the ALF LSE spectral measurements can be based on linear amplitude scaling of discrete spectral components attributable to fluorescent constituents in a liquid sample. The liquid sample can include natural waters, acetone, or methanol, among other substances. The SDC analyses can be used to provide a best fit of the spectrum resulting from the summation of discrete spectral components to the LSE signature in the selected spectral range. In an example, a set of the SDC spectral components, $\{E(\lambda)\}$, can be derived from LSE spectra measured in laboratory and field conditions and corrected for a spectrometer spectral sensitivity. PeakFit software (e.g., from SeaSolve Software, Inc.) can be used for implementing LSE spectral deconvolution to retrieve analytical approximations of the basic spectral components, such as using the Pearson's IV function(s) to describe the asymmetrical spectral shape of the constituent emission bands:

$$y = \frac{a_0\left[1 + \frac{\left(x - \frac{a_2 a_4}{2 a_3} - a_1\right)^2}{a_2^2}\right]^{-a_3} \exp\left[-a_4\left(\tan^{-1}\left(\frac{x - \frac{a_2 a_4}{2 a_3} - a_1}{a_2}\right) + \tan^{-1}\left(\frac{a_4}{2 a_3}\right)\right)\right]}{\left(1 + \frac{a_4^2}{4 a_3^2}\right)^{-a_3}},$$

where $a_0$, $a_1$, $a_2$, $a_3$, and $a_4$ are parameters that represent the amplitude, center, width, $shape_1$, and $shape_2$, respectively, of the Pearson's IV band.

Figure 4A:
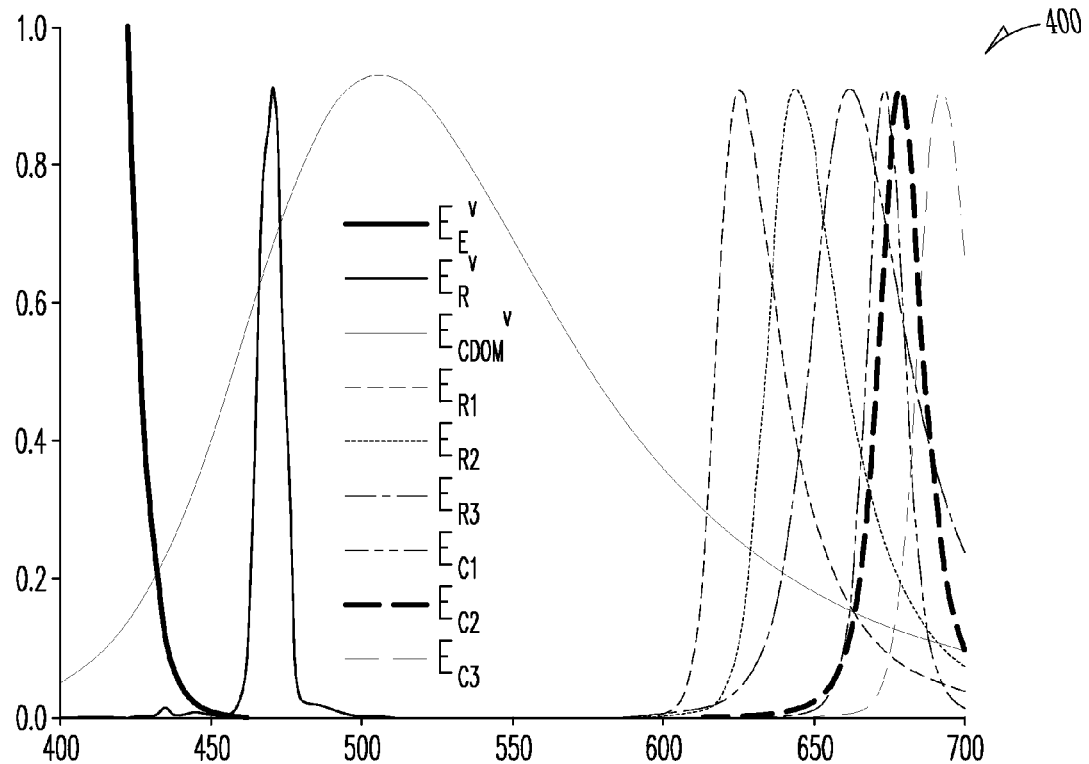
FIG. 4A illustrates generally the basic spectral components used for spectral deconvolution of the LSE signatures of natural waters measured with blue laser excitation.
Figure 4B:
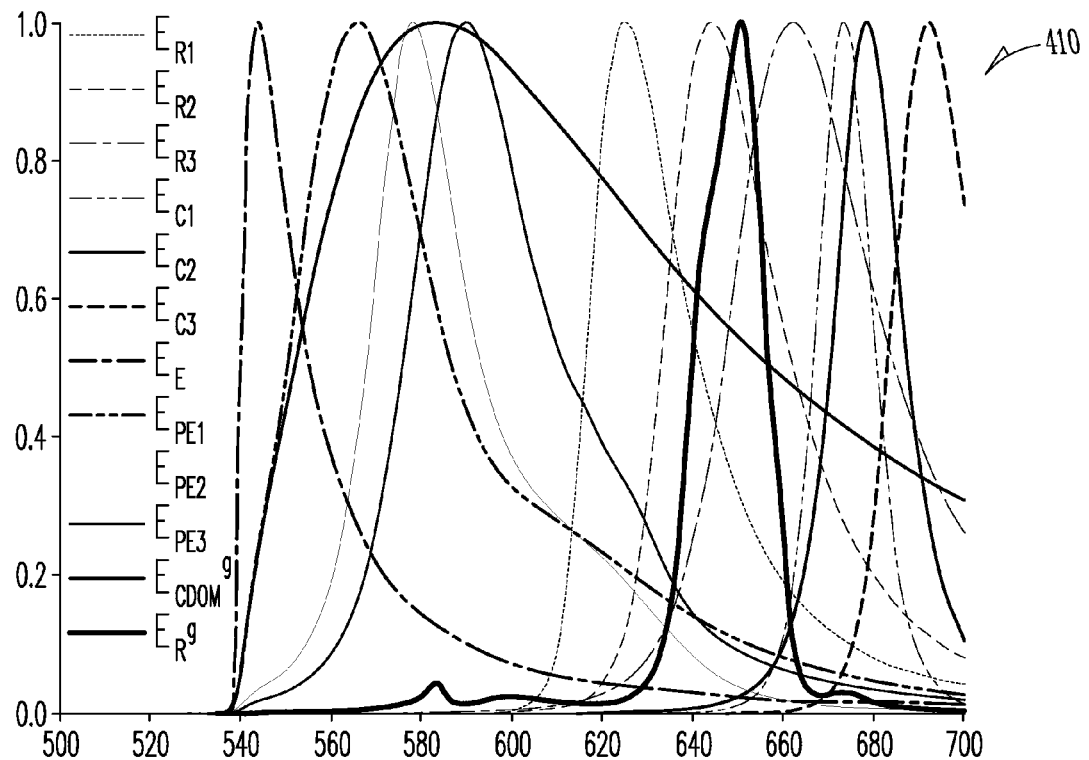
FIG. 4B illustrates generally the basic spectral components used for spectral deconvolution of the LSE signatures of natural waters measured with green laser excitation.

In an example, 15 basic, discrete spectral components (see, e.g., FIGS. 4A, 4B, and Table 1) can be included in the SDC procedure, such as to account for the LSE spectral variability observed in the field. In an example, the The $E_E^{v,g}$ and $E_R^{v,g}$ SDC components, such as representing the elastic and Raman scattering, such as water Raman (WR) scattering, can be retrieved from the ALF LSE measurements of a water sample with analytical parameterization of their respective spectral bands, such as using the PeakFit software. In an example, the WR scattering can be approximated using several Pearson's IV components to account for its complex spectral shape. In an example, the CDOM fluorescence components can be extracted from the LSE spectra of water samples from the Delaware River, filtered via 0.2 μm filters (e.g. Supor brand) to remove the particulate matter. In an example, the Raman and elastic scattering components can be appropriately scaled and digitally subtracted from the $LSE^v$ and $LSE^g$ signatures of the filtrates to parameterize the residual CDOM fluorescence spectra.

In an example, a set of the LSE signatures of laboratory-grown cultures of phytoplankton and cyanobacteria can be analyzed such as to derive several spectral components that can describe spectral variability in the phycoerythrin (PE) and Chl-a fluorescence observed in the field measurements (see, e.g., FIGS. 5A-5F, and 6A-6F, and the relevant discussion in the Assessment portion of this document). Such cultures can be maintained, for example, in L1 media and diluted to concentrations close to those occurring in natural waters. In an example, the $E_{C2}$ and $E_{C2}$ SDC components ($\lambda_{max}$=679 and 693 nm, respectively) can be retrieved from the $LSE^v$ spectrum of the red-tide dinoflagellate Alexandrium Monilatum via digital subtraction of the CDOM background fluorescence and by a PeakFit SDC analysis and parameterization of the residual. In an example, SDC analysis of the LSE spectra measured in diverse water types can show that these components can be used to describe most of the spectral variability in the 680-685 nm range, where the Chl-a fluorescence peak is typically located. Nonetheless, several ALF field deployments during the dinoflagellate blooms have indicated significant short-wavelength shifts in the Chl-a fluorescence peak that could be found in the 673-677 nm range (see, e.g., FIG. 6B, and the relevant discussion in the Assessment portion of this document). The $E_{C1}$ component ($\lambda_{max}$=673.4 nm) can be included in the SDC set to detect and quantify the short-wavelength Chl-a fluorescence variability. In an example, the $E_{C1}$ component can be derived via PeakFit parameterization of the intense short-wavelength shoulder of Chl-a fluorescence detected in the laboratory-grown culture of dinoflagellate Prorocentrum Scutellum, such as can be diluted with cold filtered seawater to induce a possible physiological response represented by the peak wavelength shift.

In an example, three additional spectral bands, $E_{PE1}$, $E_{PE2}$, and $E_{PE3}$, can be included in the SDC set of components to address the spectral variability in the PE fluorescence that can provide potential for discrimination and assessment of the cyanobacteria and PBP-containing eukaryotic cryptophytes in the mixed phototrophic populations. In a particular example, the $E_{PE1}$ SDC component (e.g., $\lambda_{max}$=565 nm) can be used for characterization of cyanobacteria that contain the Type1 PE with high phycourobilin/phycoerythrobilin (PUB/PEB) ratio, which makes them better adapted for light harvesting in the high-transparent blue oceanic waters. The $E_{PE2}$ component (e.g., $\lambda_{max}$=578 nm) can be used for detection of cyanobacteria containing the low-PUB/PEB Type 2 PE that can have advantage in greenish shelf and slope waters, such as with elevated CDOM and relatively high attenuation of blue light. The $E_{PE3}$ component (e.g., $\lambda_{max}$=589 nm) can be used for assessment of PE545-containing cryptophytes, such as can be abundant in coastal, bay and estuarine environments, as shown by our recent ALF deployments. In an example, the PE SDC components can be derived via the PeakFit SDC analysis of the $LSE^g$ spectra of laboratory-grown cultures of cyanobacteria and cryptophytes containing the respective PE spectral types. In a particular example, the WH8102 strain of *Synechococcus* sp. (e.g., CCMP2370, Provasoli-Guillard culture collection) and unicellular PE-rich Synechococcus-type cyanobacteria isolated from Pensacola Bay can be used to derive the $E_{PE1}$ and $E_{PE2}$ components, respectively. In an example, the fluorescence analysis of cryptophyte *Rhodomonas* sp. 768 can be used to derive the $E_{PE3}$ component. In an example, along with the main maxima, the long-wavelength vibrational shoulders of the PE fluorescence, such as can be detected by the PeakFit analysis, can be included in the PE component spectra as additional Pearson's IV sub-peaks (see, e.g., Table 2) to improve the SDC accuracy in the spectrally-complex yellow-red portions of the $LSE^g$ signatures (see, e.g., FIGS. 6D-F).

While most of the components can be attributed to the fluorescence or scattering bands of the specific aquatic constituents, the origin of several emission bands detected in the field in the red portion of the spectrum remains to be identified. In an example, three spectral components, $E_{R1}$, $E_{R2}$, and $E_{R3}$ ($\lambda_{max}$=625, 644, and 662 nm, respectively), can be included in the SDC component set to address an observed LSE variability and provide for its quantification and analysis. In an example, the spectral shape of the red SDC components can be retrieved from the residual spectra, such as can be composed via digital subtraction of the known overlapped SDC components from $LSE^v$ signatures containing unidentified red spectral bands. The magnitudes of the Pearson's parameters, $a_0$, $a_1$, $a_2$, $a_3$ and $a_4$, for the spectral components used in the SDC procedure are presented in Table 2. The peak-normalized spectral distribution for each of the components can be calculated using the Pearson's function (or a sum of the functions if several lines of Pearson's parameters are listed for the component in Table 2) with the argument $x=\lambda$. Here, $\lambda$ is the spectral wavelength in nm, e.g., 532 nm or 651 nm.

SDC Analysis of $LSE^v$ Spectra

In an example, the SDC processing of the $LSE^v$ spectra can include the following steps:

1v. The measured $LSE^v$ signature can be corrected for the spectrometer spectral sensitivity and normalized to its peak to yield the $LSE^v_n(\lambda)$ signature scaled down to the normalized amplitudes of the SDC basic components, such as to minimize the number of the SDC best fitting iterations.

2v. Fit$^v(\lambda)$, the sum of the 9 spectral components listed in Table 1, can be calculated with a set of scaling amplitude coefficients, $\{v_i\}$:

$$\text{Fit}^v(\lambda) = v_1 E_R^v(\lambda) + v_2 E_E^v(\lambda) + v_3 E_{CDOM}^v(\lambda) + v_4 E_{C1}(\lambda) + v_5 E_{C2}(\lambda) + v_6 E_{C3}(\lambda) + v_7 E_{R1}(\lambda) + v_8 E_{R2}(\lambda) + v_9 E_{R3}(\lambda) \quad (1)$$

where $\lambda$ represents a spectral wavelength. The magnitudes of the scaling coefficients can be varied until the sum of squares of residuals between the Fit$^v$ and $LSE^v_n$ is minimized in the fitting spectral range. For the ALF $LSE^v$ measurements, the fitting range can, in an example, include two spectral sub-ranges, such as 423 nm to 515 nm, and 550 nm to 700 nm, where the emission peaks of the key aquatic constituents are located in the $LSE^v$ spectra (see, e.g., FIGS. 5A-5F). The initial (e.g., 380-423 nm) and intermediate green (e.g., 515-550 nm) portions of the $LSE^v$ signatures, where F1 and F2 filters 246 of the ALF spectrometer 210 have high optical density, can be excluded from the SDC analysis. The NIR portion (700-808 nm) can also be excluded, in an example, because of the NIR decline in the spectrometer sensitivity.

3v. The retrieved values of scaling amplitude coefficients can be used to calculate the SDC components of the $LSE^v_n$ signature, such as can be displayed by the ALF software in a representation of the $LSE^v$ spectral panel, along with the $LSE^v_n$ and $LSE^v_{fit}$ spectra, to visualize the results of best fitting (for example, see FIGS. 5A-5F):

$$S_R^v(\lambda) = v_1 E_R^v(\lambda)$$

$$S_E^v(\lambda) = v_2 E_E^v(\lambda)$$

$$F_{CDOM}^v(\lambda) = v_3 E_{CDOM}^v(\lambda)$$

$$F_{C1}^v(\lambda) = v_4 E_{C1}(\lambda)$$

$$F_{C2}^v(\lambda) = v_5 E_{C2}(\lambda) \quad (2)$$

$$F_{C3}^v(\lambda) = v_6 E_{C3}(\lambda)$$

$$F_{R1}^v(\lambda) = v_7 E_{R1}(\lambda)$$

$$F_{R2}^v(\lambda) = v_8 E_{R3}(\lambda)$$

$$F_{R3}^v(\lambda) = v_9 E_{R3}(\lambda)$$

In an example, the SDC ALF algorithm can integrate the $F_{C1}^v(\lambda)$, $F_{C2}^v(\lambda)$, and $F_{C3}^v(\lambda)$ spectral components, such as to synthesize the Chl-a fluorescence component of the $LSE_n^v$ spectrum:

$$F_{Chla}^v(\lambda) = v_4 E_{C1}(\lambda) + v_5 E_{C2}(\lambda) + v_6 E_{C3}(\lambda) \quad (3)$$

$$v_{Chla} = \max(F_{Chla}^v(\lambda))$$

where $v_{Chla}$ is the $F_{Chla}^v(\lambda)$ peak magnitude. The $F_{Chla}^v(\lambda)$ synthesis can account for the spectral variability in Chl-a fluorescence observed in the field (see, e.g., FIGS. 5A-5F). In an example, the wavelength of the $F_{Chla}^v(\lambda)$ peak, $\lambda_{Chla}^v$, can also be determined to assess the spectral variability in Chl-a fluorescence and spectral correction of variable fluorescence, as described below.

4v. A set of relative parameters for the $LSE^v$ spectral components can be calculated as:

$$I_{Chla/R}^v = v_{Chla} v_1^{-1}$$

$$I_{CDOM/R}^v = v_3 v_1^{-1}$$

$$I_{R1/R}{}^v = v_7 v_1{}^{-1} \quad (4)$$

$$I_{R2/R}{}^v = v_8 v_1{}^{-1}$$

$$I_{R3/R}{}^v = v_9 v_1{}^{-1}$$

These parameters can represent signal intensities of the constituent fluorescence bands contributing to the $LSE^v$ spectrum normalized to $WR^v$. They can be used for quantitative assessment of the major fluorescent constituents, such as Chl-a or CDOM (see, e.g., FIGS. 7A and 7B) or for parameterization of the $LSE^v$ spectral shape, which can be described with the set of five relative parameters determined by equation (4).

Figure 15:
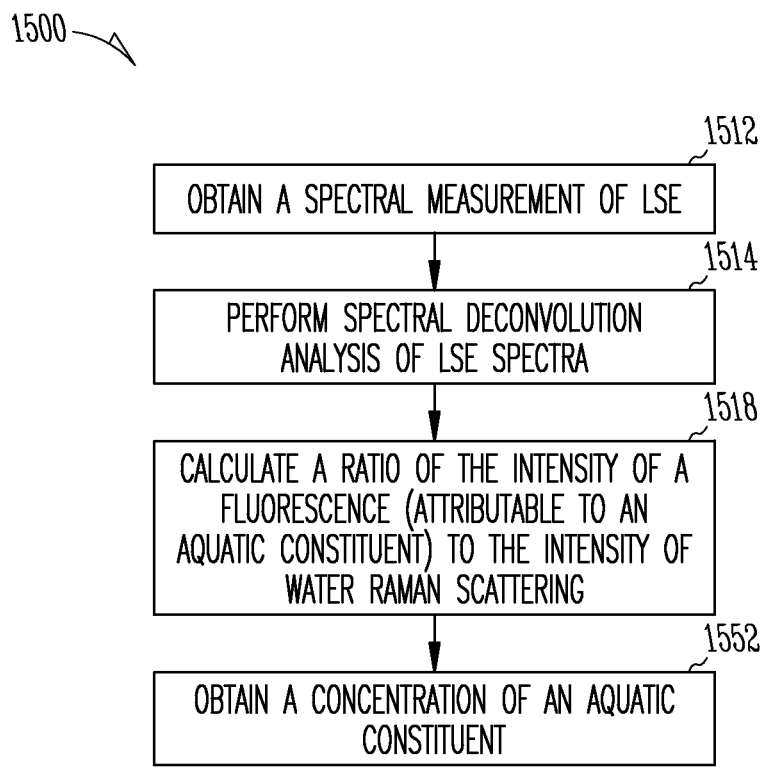
FIG. 15 illustrates generally an example that can include obtaining a concentration of an aquatic constituent.

FIG. 15 illustrates generally an example of obtaining a quantitative assessment of a fluorescent constituent that can include a concentration of an aquatic constituent, such as Chl-a. At 1512, a spectral measurement can be obtained of LSE, such as using the ALF instrument. At 1514, SDC analysis of LSE spectra can be performed, such as to deconvolve from the measured spectra individual bands attributable to discrete aquatic constituents. In an example, the SDC analysis can yield the magnitude of a fluorescence intensity attributable to Chl-a, among other aquatic constituents.

At 1518, a ratio of the intensity of a fluorescence, such as can be attributable to a fluorescent constituent, to the intensity of WR scattering can be calculated. In an example, several ratios can be calculated, such as using equation (4). In an example, the set of relative fluorescent parameters in equation (4) can be used to provide a quantitative assessment of a constituent-specific concentration in a liquid sample, such as an absolute measurement of a concentration of an individual fluorescent constituent in a water sample.

Figure 7A:
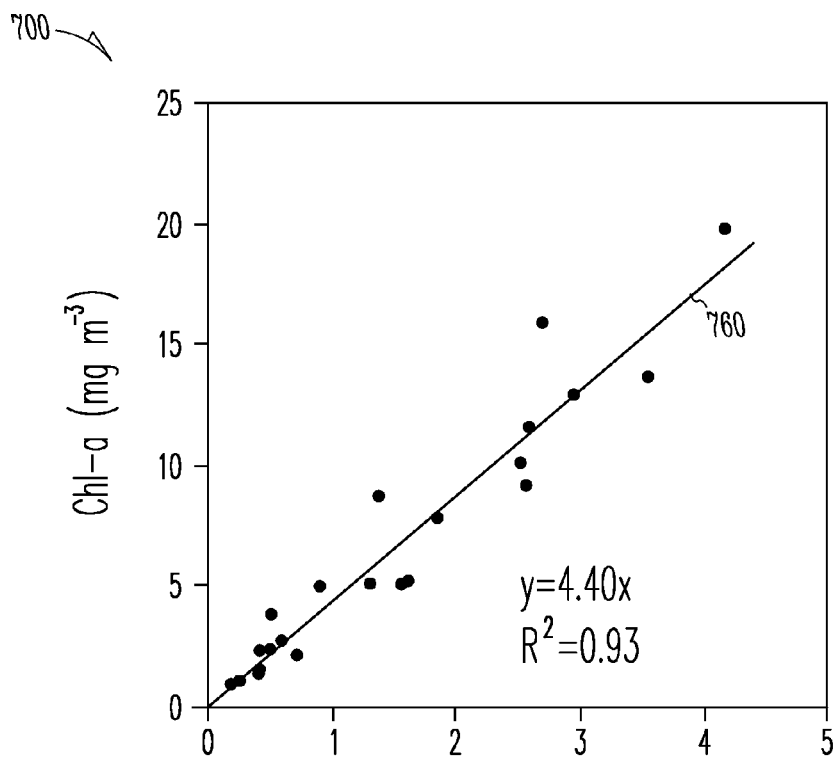
FIG. 7A illustrates generally a correlation between the SDC retrievals of the $I_{Chla/R}^v$ fluorescence parameter and the HPLC measurements of total Chl-a conducted in the Middle Atlantic Bight, Chesapeake and Delaware Bays, and in the Sough Slough estuary (Oregon) and York River (Va.).
Figure 7B:
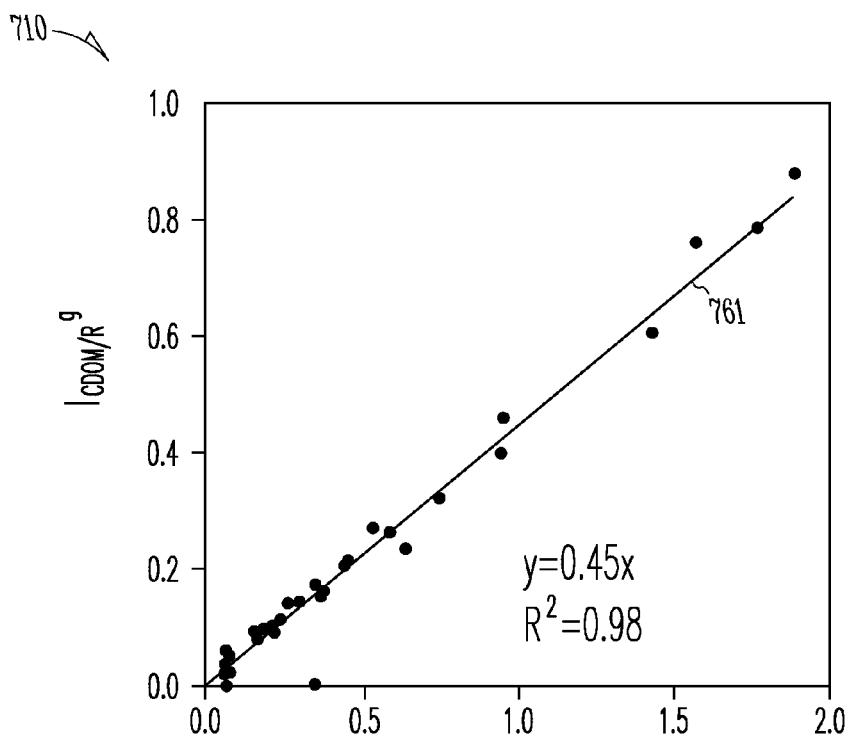
FIG. 7B illustrates generally a correlation between the $I_{CDOM/R}^v$ and $I_{CDOM/R}^g$ parameters of CDOM fluorescence measured with blue and green laser excitation, respectively, in the Delaware Bay and adjacent coastal and offshore areas of the Middle Atlantic Bight.

At 1552, a concentration of an aquatic constituent can be obtained. In an example, concentrations of individual fluorescent constituents can be determined by multiplying the intensities of constituent-specific fluorescence bands normalized to WR scattering (i.e., a relative parameter determined using equation (4)) and a conversion coefficient, such as can be obtained from a regression line in a plot of the intensities of constituent-specific fluorescence bands normalized to WR scattering and independent measurements of the constituent-specific concentrations. For example, FIG. 7A illustrates generally an example of how such conversion coefficient can be obtained. $I_{Chla/R}{}^v$, a relative, dimensionless quantity indicative of Chl-a fluorescence intensity normalized to WR scattering, can be plotted along a horizontal axis. Independent measurements of Chl-a fluorescence intensity, such as can be obtained using HPLC, for example, can be plotted along a vertical axis. In the example of FIG. 7A, a regression line can be determined, and the conversion coefficient 4.40 can be obtained. The conversion coefficient can be used to convert the relative, dimensionless quantity $I_{Chla/R}{}^v$ to an absolute quantity of fluorescence concentration (e.g., in mg m$^{-3}$). In an example, the conversion coefficient can be obtained during a calibration procedure using the ALF instrument and a set of dark-adapted liquid samples containing photosynthesizing microorganisms. In an example, $I_{Chla/R}{}^v$, although a relative, dimensionless quantity, can be a useful index of Chl-a concentration where it can be compared to other $I_{Chla/R}{}^v$ measurements conducted using various instrumental implementations of the ALF technique and platforms, including autonomous unmanned vehicles and airborne or satellite remote sensing. Further improvements in the accuracy of fluorescence assessments of Chl-a concentration are described below.

SDC Analysis of $LSE^g$ Spectra

The SDC analysis of the $LSE^g$ spectra can be similar to the $LSE^v$ SDC analysis, though three additional components can be included in the SDC procedure to account for the spectral variability in PE fluorescence efficiently stimulated with a green laser excitation, such as using the green laser 212. In an example, the SDC processing of the $LSE^g$ spectra can include the following steps:

1g. The measured $LSE^g$ signature can be corrected for the spectrometer spectral sensitivity and normalized to its peak to yield the $LSE^g{}_n(\lambda)$ signature.

2g. Fit$^g(\lambda)$ the sum of the 12 spectral components listed in Table 1, is calculated with a set of scaling amplitude coefficients $\{g_i\}$:

$$\text{Fit}^g(\lambda) = g_1 E_R^g(\lambda) + g_2 E_E^g(\lambda) + g_3 E_{CDOM}^g(\lambda) + g_4 E_{C1}(\lambda) + g_5 E_{C2}(\lambda) + g_6 E_{C3}(\lambda) + g_7 E_{R1}(\lambda) + g_8 E_{R2}(\lambda) + g_9 E_{R3}(\lambda) + g_{10} E_{PE1}(\lambda) + g_{11} E_{PE2}(\lambda) + g_{12} E_{PE3}(\lambda) \quad (5)$$

where $\lambda$ is a spectral wavelength. The magnitudes of the scaling coefficients can be varied until the sum of squares of residuals between the $LSE^g{}_{fit}$ and $LSE^g{}_n$ is minimized in the spectral range of SDC fitting, such as the spectral range 544 nm to 700 nm, where the emission peaks of key aquatic constituents can be located in the $LSE^g$ spectra (see, e.g., FIG. 6).

3g. The retrieved values of scaling coefficients can be used to calculate the SDC components of the $LSE^g{}_n$ signature, such as can be displayed by the ALF software in a representation of the LSEg spectral panel, along with the $LSE^g{}_n$ and $LSE^g{}_{fit}$ spectra, to visualize the results of best fitting (for example, see FIGS. 6A-6F):

$$S_R^g(\lambda) = g_1 E_R^g(\lambda);$$

$$S_E^g(\lambda) = g_2 S_E^g(\lambda)$$

$$F_{CDOM}^g(\lambda) = g_3 E_{CDOM}^g(\lambda)$$

$$F_{C1}^g(\lambda) = g_4 E_{C1}(\lambda)$$

$$F_{C2}^g(\lambda) = g_5 E_{C2}(\lambda)$$

$$F_{C3}^g(\lambda) = g_6 E_{C3}(\lambda)$$

$$F_{R1}^g(\lambda) = g_7 E_{R1}(\lambda) \quad (6)$$

$$F_{R2}^g(\lambda) = g_8 E_{R3}(\lambda)$$

$$F_{R3}^g(\lambda) = g_9 E_{R3}(\lambda)$$

$$F_{PE1}^g(\lambda) = g_{10} E_{PE1}(\lambda)$$

$$F_{PE2}^g(\lambda) = g_{11} E_{PE2}(\lambda)$$

$$F_{PE3}^g(\lambda) = g_{12} E_{PE3}(\lambda)$$

In an example, the SDC ALF algorithm can integrate the $F_{C1}^g(\lambda)$, $F_{C2}^g(\lambda)$, and $F_{C3}^g(\lambda)$ spectral components, such as to synthesize $F_{Chla}^g(\lambda)$, the Chl-a fluorescence component of the $LSE^g{}_n$ spectrum, or to use in determining the $F_{Chla}^g(\lambda)$ peak magnitude, $g_{Chla}$:

$$F_{Chla}^g(\lambda) = g_4 E_{C1}(\lambda) + g_5 E_{C2}(\lambda) + g_6 E_{C3}(\lambda) \quad (7)$$

$$g_{Chla} = \max(F_{Chl-a}^g(\lambda))$$

The wavelength of the $F_{Chla}^g(\lambda)$ peak, $\lambda_{Chla}^g$, can also be determined to assess a spectral variability in Chl-a fluorescence.

The SDC retrievals of the $F_{PE1}^g(2)$ and $F_{PE2}^g(2)$ bands can be used for discrimination and assessment of the Type 2 and Type 1 PE-containing cyanobacteria, respectively. In addition, the integrated synthetic cyanobacterial PE fluorescence band, $F_{PE12}{}^g(\lambda)$, and its peak magnitude, $g_{PE12}$ can also be generated for the overall assessment of the PE-containing cyanobacterial population:

$$F_{PE12}{}^g(\lambda) = g_{10}E_{PE1}(\lambda) + g_{11}E_{PE2}(\lambda) \quad (8)$$

$$g_{PE12} = \max(F_{PE12}{}^g(\lambda))$$

These parameters can be used to examine a relationship with high-performance liquid chromatography (HPLC) and other analyses that do not discriminate within the cyanobacterial group.

4g. A set of relative parameters for the $LSE^g$ spectral components is calculated as:

$$I_{Chla/R}{}^g(\lambda) = g_{Chla}g_1{}^{-1}$$

$$I_{CDOM/R}{}^g = g_3 g_1{}^{-1}$$

$$I_{R1/R}{}^g = g_7 g_1{}^{-1}$$

$$I_{R2/R}{}^g = g_8 g_1{}^{-1}$$

$$I_{R3/R}{}^g = g_9 g_1{}^{-1} \quad (9)$$

$$I_{PE1/R}{}^g = g_{10}g_1{}^{-1}$$

$$I_{PE2/R}{}^g = g_{11}g_1{}^{-1}$$

$$I_{PE3/R}{}^g = g_{12}g_1{}^{-1}$$

These parameters can represent $WR^g$-normalized peak signal intensities of the major fluorescence bands contributing to the formation of the $LSE^g$ signature. As analogues of parameters retrieved from the $LSE^v$ SDC analysis, they can be used for quantitative assessment of the major fluorescence constituents, such as Chl-a, PE, or CDOM, or for parameterization of the $LSE^g$ spectral shape, which can be described with a set of, for example, eight relative parameters, such as can be determined using equation (9). Several additional parameters, which can provide useful indexes for structural characterization of the mixed population of phytoplankton and cyanobacteria (see, e.g., FIGS. 8A-8D), can also be calculated:

$$I_{PE12/Chla} = g_{PE12}g_{Chl}{}^{-1}$$

$$I_{PE1/Chla} = g_{10}g_{Chl}{}^{-1}$$

$$I_{PE2/Chla} = g_{11}g_{Chl}{}^{-1} \quad (10)$$

$$I_{PE3/Chla} = g_{12}g_{Chl}{}^{-1}$$

$$I_{PE1/PE2} = g_{10}g^{-1}$$

Spectral Correction of Temporal Retrievals of Variable Fluorescence

The Chl-a fluorescence induction, caused by the gradual closure of the reaction centers of photosystem II (PSII), occur over the single PSII turnover time scale (e.g., 40-100 μs) with the appropriate excitation flux. The parameters of variable fluorescence, a proxy of the quantum yield of PSII photochemistry and handy index of photo-physiological status of photosynthesizing organisms, can be retrieved from the PDP induction measurements. In particular, the Chl-a fluorescence induction, $F_{Chla}(t)$, measured using the PDP excitation protocol employed in the ALF instrument, can be approximated as:

$$F_{Chla}(t) = (F_m{}^{-1} - (F_m{}^{-1} - F_o{}^{-1})\exp(-t/A))^{-1} \quad (11)$$

where, $F_o$ and $F_m$ represent initial and maximum intensity of Chl-a fluorescence, respectively, and A represents a time constant. The non-linear best fitting with equation (11) to a measured Chl-a fluorescence induction yields the parameters of variable fluorescence, $F_o$, $F_m$ and A. The magnitude of variable fluorescence can be calculated as $F_v/F_m = (F_m - F_o)/F_m$. In an example, the magnitude of variable fluorescence can be used to account for physiological variability in the quantum yield of chlorophyll-a fluorescence. In an example, the magnitude of variable fluorescence can be used as a quantitative measure of a physiological status of photosynthesizing organisms, and the quantitative measure can be used to adjust an intensity measurement of chlorophyll-a fluorescence, such as can be obtained using SDC analysis of LSE.

Figure 5A:
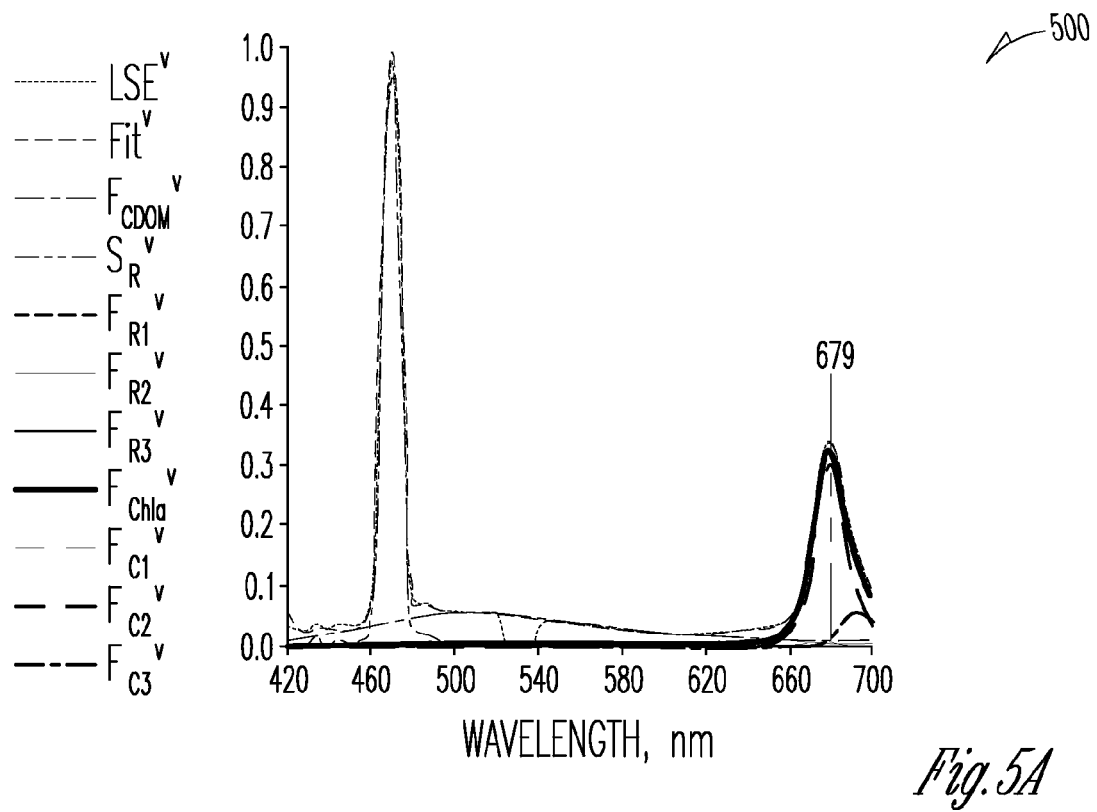
FIGS. 5A, 5B, 5C, 5D, 5E, and 5F illustrate generally variability in the $LSE^v$ spectra measured in diverse water types with blue laser excitation.
Figure 5B:
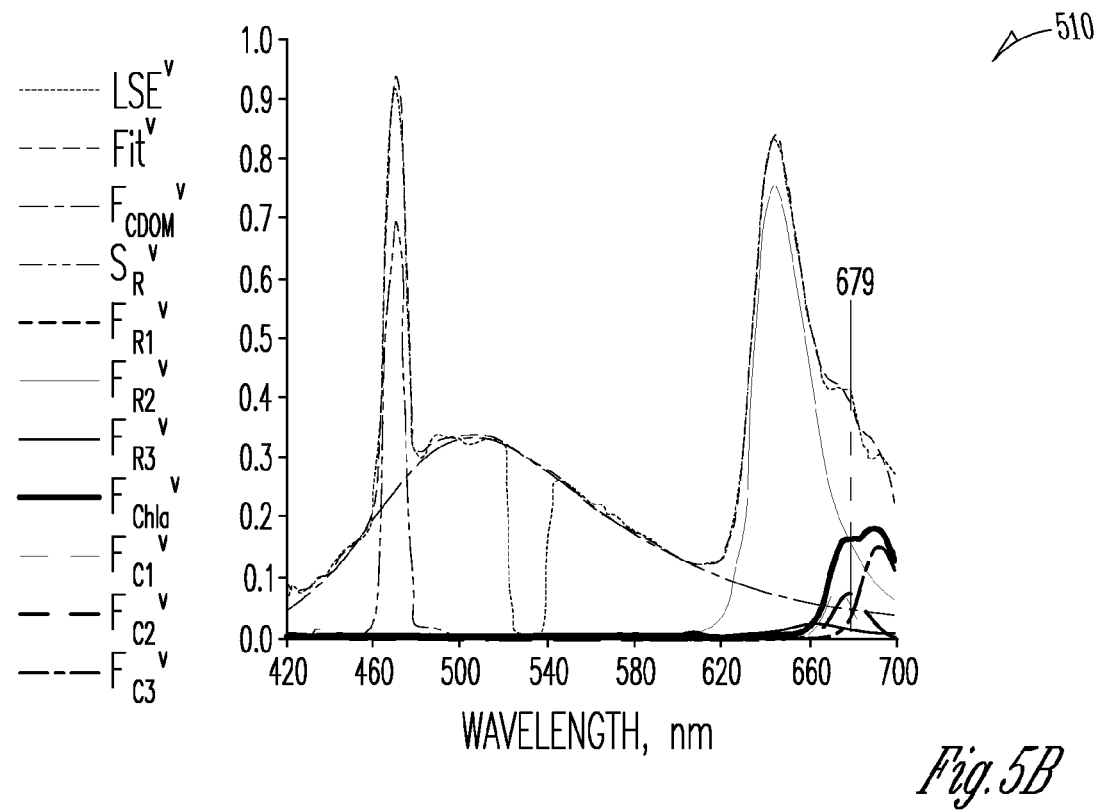
Figure 5C:
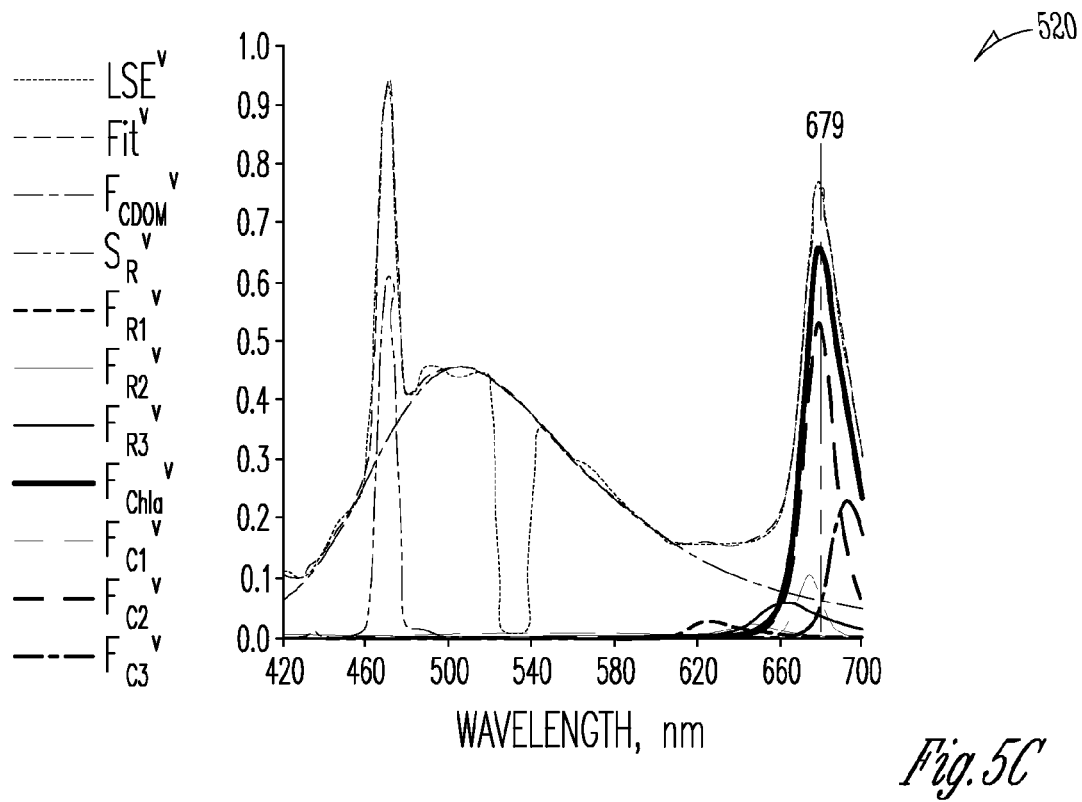
Figure 5D:
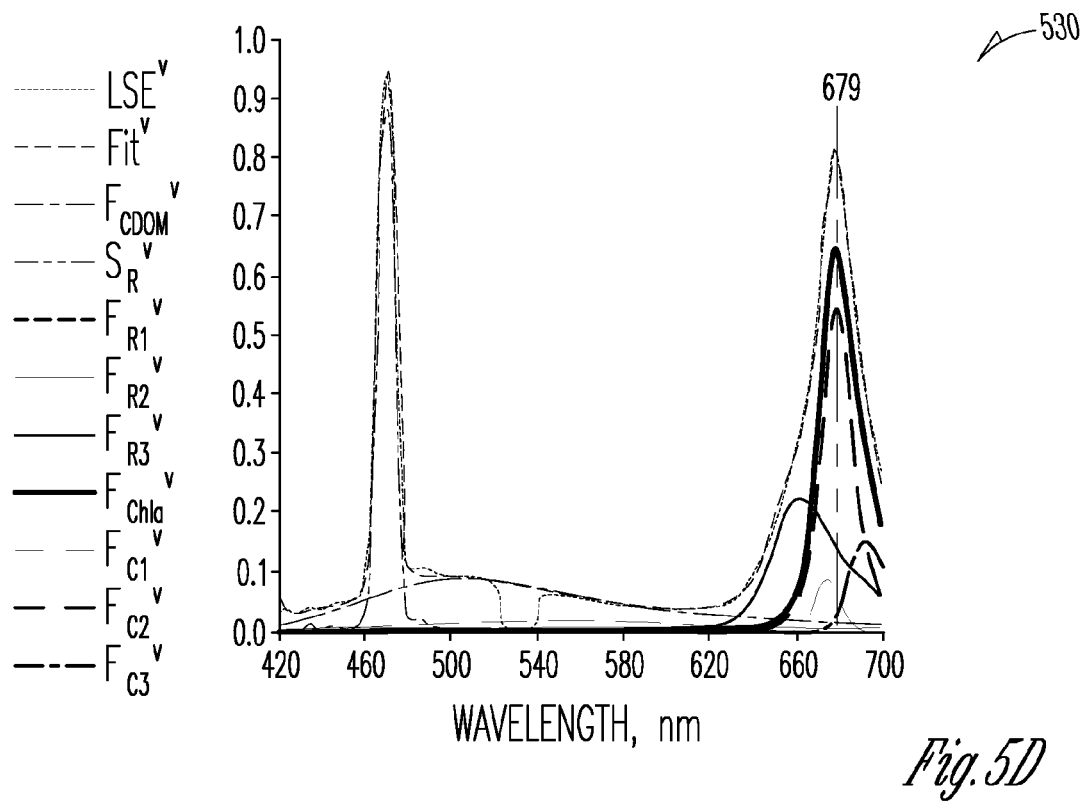
Figure 5E:
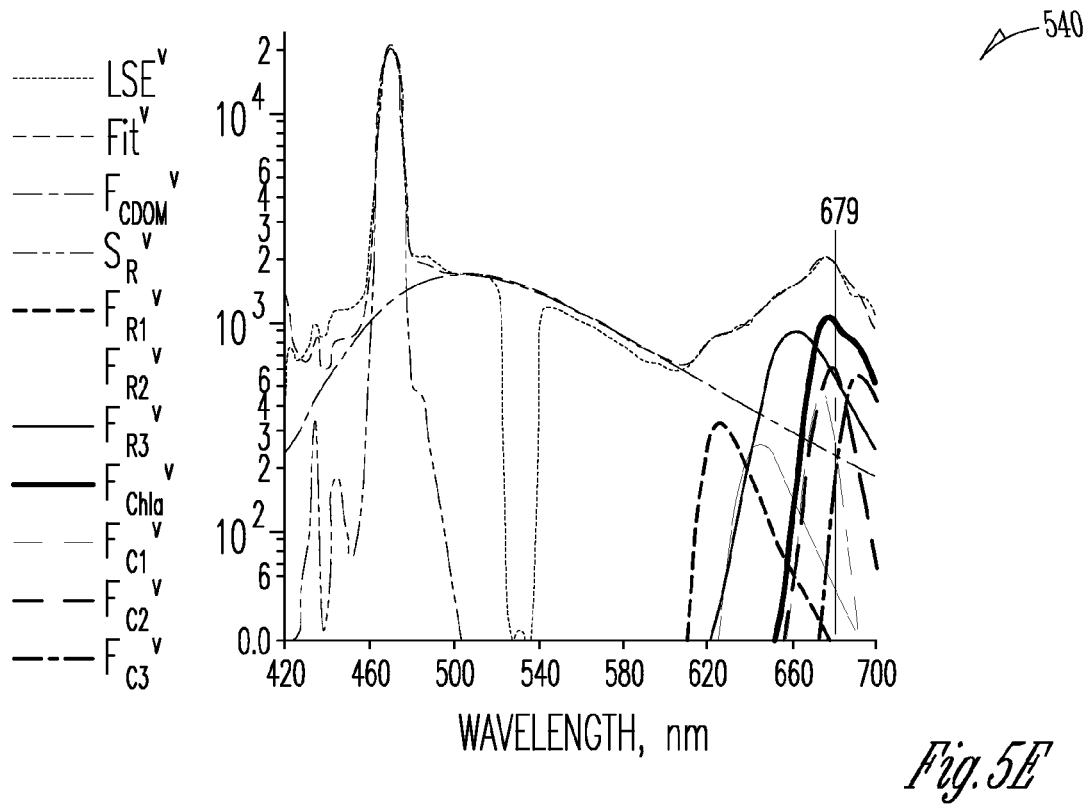
Figure 5F:
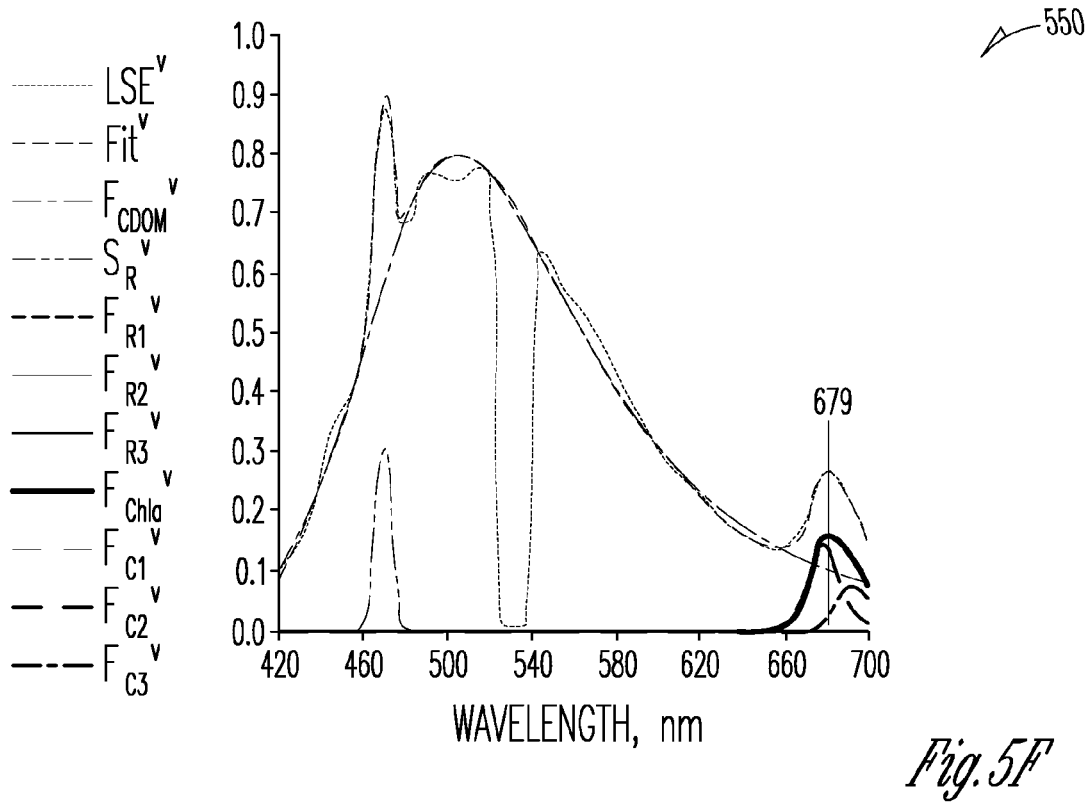

In an example, the fluorescence induction measured in natural waters can be corrected for the non-Chl-a background emission, $B_{NC}$, such as can be produced by the broadband CDOM fluorescence in the area of the Chl-a fluorescence peak (e.g., FIG. 5F). Elevated levels of phaeophytin can also affect measurements of the variable fluorescence. Other constituents present in natural waters can also contribute to the $B_{NC}$ in this spectral region (for example, see FIGS. 5B, 5C, 5E, and 5D). The $B_{NC}$ magnitude remains unchanged during the Chl-a fluorescence induction, as it has no relation to the dynamic changes in the PSII status stimulated by the actinic flash. Not accounting for the $B_{NC}$ background can result in flattening the induction curves and underestimating the variable fluorescence, which can be significant even in the offshore oceanic waters with low CDOM content.

Most fluorometers that measure variable fluorescence do not possess adequate spectral resolution for discrimination between the Chl-a fluorescence and $B_{NC}$. One approach could be to use periodic measurements of the blanks and filtrates to address the issue. A further advance to this approach can use automatic assaying of the filtrate fluorescence each hour during the continuous underway flow-through measurements. Though it may partially improve the $F_v/F_m$ assessments, the variable fluorescence retrievals can be corrected for the $B_{NC}$ background measured in the same water sample to account for the $B_{NC}$ spatial and temporal variability. Also, both dissolved and particulate organic matter present in natural waters may contribute to the $B_{NC}$ background, while the filtrate measurements account only for the dissolved component.

The ALF instrument, which can uniquely combine both spectrally and temporally resolved LSE measurements of a sampled liquid, can be used to compute characteristics of fluorescent substances in the sampled liquid, such as using information from one of the spectral or temporal measurements to adjust the other of the spectral or temporal measurement. For example, quantitative information about aquatic constituents, such as can be obtained from spectrally resolved measurements, can be used to improve an assessment of a photo-physiological status of phytoplankton, such as can be obtained from temporally resolved measurements. In an example, physiological information, such as information obtained from temporally resolved measurements, can be used to improve a quantitative assessment, such as an assessment of a Chl-a concentration in a water sample obtained from spectrally resolved measurements. In an example, combining the spectrally and temporally resolved LSE measurements of the sampled water can be used to compute characteristics of fluorescent substances, such as a chlorophyll-a concentration. In an example, the Comp 101, including a processor circuit, can be used to perform the computations of characteristics of fluorescent substances.

In an example, the ALF instrument can provide potential for retrieving from the induction measurements an actual Chl-a fluorescence signal and its spectral discrimination, regardless of the $B_{NC}$ origin and magnitude. Because the temporal and spectral measurements can be conducted in a continuous flow of sampled water with a few seconds delay, the spectrally and temporally resolved measurements can represent the same analyzed water and can be directly related. In an example, a spectral measurement can include the intensity of non-Chl-a fluorescence background in the $LSE^v_n$ spectrum, which can be assessed via subtracting the SDC-retrieved spectral peak magnitude of the Chl-a fluorescence, $v_{Chla}$ (see, e.g., equation (3)), from the $LSE^v_n$ spectral intensity around Chl-a peak, $LSE^v_n(\lambda_{Chla}')$. The $I_{NC/Chla}$ parameter to assess the ratio of the non-Chl-a background to the $v_{Chla}$ magnitude can be therefore calculated from the SDC spectral analysis of $LSE^v$ as:

$$I_{NC/Chla} = LSE^v_n(\lambda_{Chla}')v_{Chla}^{-1} - 1 \quad (12)$$

The $I_{NC/Chla}$ spectral retrievals can be used for correction of the temporal measurements of fluorescence induction for the non-Chl-a background emission to improve photo-physiological assessments of phytoplankton variable fluorescence. The relationship between the $I_{NC/Chla}$ parameter yielded by the SDC analysis of the LSE spectrum and the $B_{NC}$ magnitude in the fluorescence induction is not trivial. The intensity of the 405 nm laser excitation is the same for measuring both the $LSE^v$ spectra and the fluorescence induction. Therefore, during the $LSE^v$ spectral acquisition (e.g., 1-3 s), the Chl-a fluorescence exhibits the initial fast (e.g., ~50 µs) induction rise followed by several additional transitional stages, referred to as Kautsky effect, to reach the steady state level approximately equal to its initial magnitude when the excitation is turned on. Therefore, the $I_{NC/Chla}$ value derived from the SDC LSE analysis can be determined by the average over the spectral acquisition time magnitude of the Chl-a fluorescence yield. The latter can be close to the mean magnitude of the Chl-a yield during the PDP induction measurements under conditions of the measurements. Thus, to a first approximation, the $B_{NC}$ background and the $B_{NC}$-corrected time course of variable fluorescence, $F_{Chla}(t)$, can be estimated as (see, e.g., FIG. 9B for illustration):

$$B_{NC} = (I + I_{NC/Chla}^{-1})^{-1} \text{mean}(F_{PDP}(t)), \text{ and} \quad (13)$$

$$F_{Chla}(t) = F_{PDP}(t) - B_{NC} \quad (14)$$

where $F_{PDP}(t)$ is a temporal measurement, such as the time course of fluorescence induction measured in the spectral region of the Chla-fluorescence peak by the ALF instrument. Equations 13 and 14 can be used during the real-time processing of the temporal fluorescence measurements to retrieve a corrected induction curve of Chl-a fluorescence, $F_{Chla}(t)$. The non-linear fitting with equation (11) can provide the $B_{NC}$-corrected magnitude of variable fluorescence, $F_v/F_m = (F_m - F_o)/F_m$. For evaluation, the non-spectrally corrected magnitude of variable fluorescence, $F_v/F_m^{NC}$, can be calculated from results of fitting of $F_{PDP}(t)$ to equation (11). In an example, the Comp 101, such as using a processor circuit, can be configured to perform calculations using the equations 11-14, among others.

FIG. 13 illustrates generally an example that can include using information from a spectrally-resolved measurement to improve an assessment based on a temporally-resolved measurement. For example, at 1310, fluorescence induction over time, $F_{PDP}(t)$, can be obtained, such as using the ALF measurement system described above. $F_{PDP}(t)$ can represent a waveform indicative of a time course of PDP fluorescence induction, such as in response to a laser excitation of a water sample.

At 1320, spectral measurements of LSE can be used to determine quantitative information about the magnitude of a non-chlorophyll-a background fluorescence, $B_{NC}$, such as can be present in the temporal measurements of $F_{PDP}(t)$ in the spectral region of chlorophyll-a fluorescence. In an example, $B_{NC}$ can be calculated using equations 12 and 13.

At 1330, the measurement of fluorescence induction over time, $F_{PDP}(t)$, can be corrected or adjusted for the influence of background fluorescence, such as using $B_{NC}$, the magnitude of non-chlorophyll-a background fluorescence. In an example, $B_{NC}$ can be subtracted from the measurement of fluorescence induction over time to yield $F_{Chla}(t)$, a corrected waveform representative of the time course of Chl-a fluorescence induction, such as using equation 14.

At 1340, the corrected waveform $F_{Chla}(t)$ can be used to determine one or more parameters of a variable fluorescence. For example, equation 11 can be used to approximate $F_{Chla}(t)$ by adjusting the variables $F_o$, $F_m$, and A to achieve a best-fit. In an example, an alternative biophysical model, such as a model other than equation 11, can be used to approximate $F_{Chla}(t)$, and thus to determine the parameters of the variable fluorescence.

At 1350, the magnitude of the variable fluorescence can be calculated, such as using the equation $F_v/F_m = (F_m - F_o)/F_m$ and the parameters of the variable fluorescence obtained at 1340. At 1360, the magnitude of the variable fluorescence can be used, for example, to provide an indication of a physiological status of photosynthesizing organisms. In an example, the magnitude of the variable fluorescence can be used to provide a characteristic of a fluorescent substance in the water sample, such as a photo-physiological status of phytoplankton. Thus, using quantitative information, such as can be obtained from a spectral measurement of a water sample, physiological assessments of aquatic photosynthesizing organisms, such as can be obtained from a temporally-resolved measurement of the water sample, can be improved.

Improving Spectral Retrievals of Pigment Concentration Using Temporal Measurements In an example, the technique employed by the ALF instrument can provide potential for retrieving from the spectral measurements a more accurate quantitative assessment of aquatic constituents, such as an assessment of a Chl-a concentration. Because the temporal and spectral measurements can be conducted in continuous flow of the sampled water in substantially real-time (e.g., with a few seconds delay), the spectrally and temporally resolved measurements can represent the same analyzed water and can be directly related.

In an example, a spectrally-corrected magnitude of variable fluorescence, $F_v/F_m$, a convenient index of the photo-physiological status of photosynthesizing organisms, can be retrieved from the ALF temporal measurements as described in the previous section. The variable fluorescence information can be used, for example, to correct the magnitude of a Chl-a fluorescence for photo-physiological, including photo-protective, variability in its quantum yield. In an example, a normalization of Chl-a fluorescence to $F_v/F_m$ can minimize the adverse effect of a photo-physiological dependence of Chl-a fluorescence intensity on the accuracy of Chl-a concentration assessments, such as can be obtained using a spectral fluorescence measurement alone.

Figure 14:
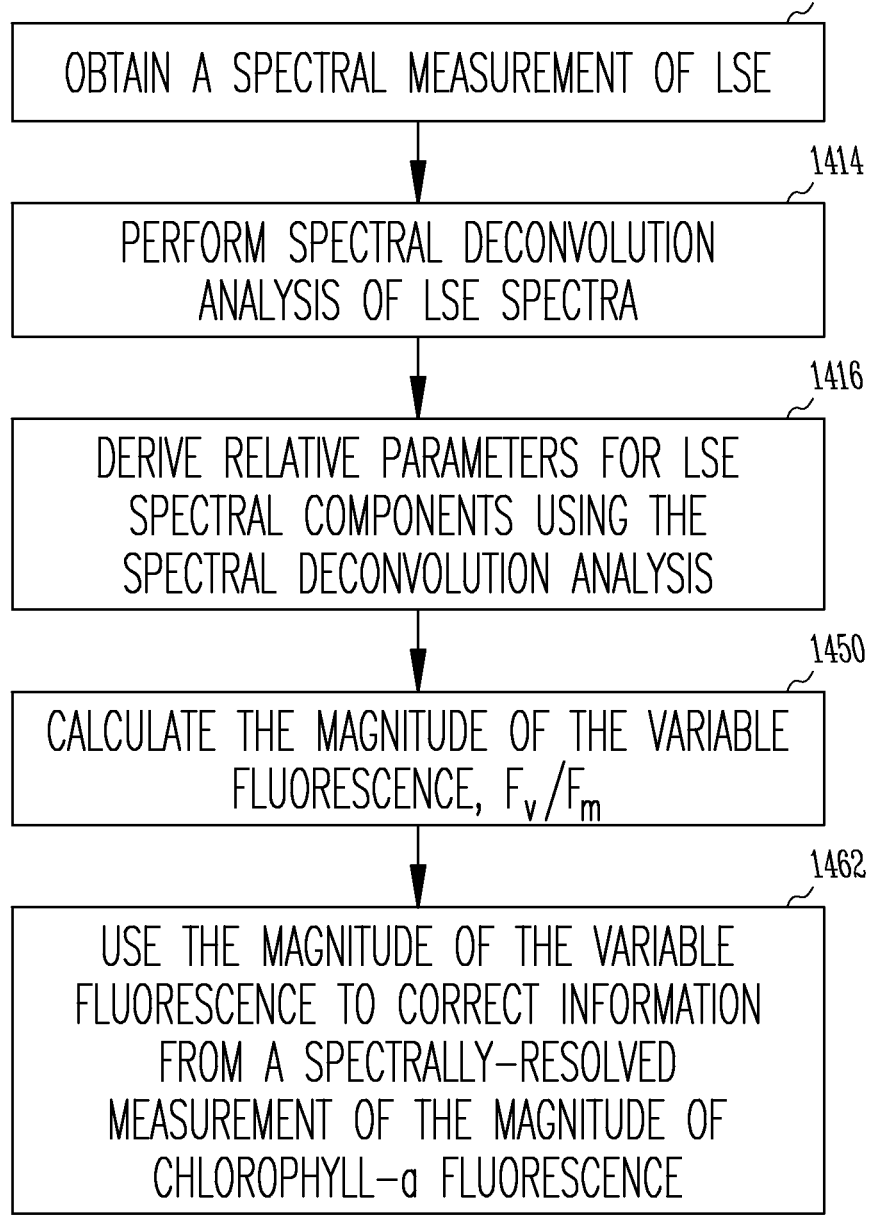
FIG. 14 illustrates generally an example that can include using information from a temporally-resolved measurement to improve an assessment based on a spectrally-resolved measurement.

FIG. 14 illustrates generally an example that can include using information from a temporal measurement to improve an assessment based on a spectral measurement. For example, at 1412, a spectral measurement of LSE can be obtained, such as using the ALF measurement system. In an example, the spectral measurement can be a broadband spectral measurement containing LSE spectral information from a variety of aquatic constituents.

At 1414, spectral deconvolution (SDC) analysis can be performed on a spectral measurement, such as the measurement obtained at 1412, to assess discrete aquatic constituents. For example, SDC can be used to retrieve from LSE signatures the individual spectral bands of aquatic constituents, thus permitting qualitative and quantitative assessment of the aquatic constituents. Some of the components that can be retrieved using SDC analysis are discussed above.

At 1416, relative parameters describing the LSE spectral components can be derived, such as using the SDC analysis performed at 1414. The relative parameters can include the ratios in equations (4), (9), or (10), among others, which can represent signal intensities of constituent fluorescence bands contributing to the spectral measurement obtained at 1412, normalized to water Raman scattering. In an example, the ratios can be used to perform quantitative assessments of fluorescent constituents such as Chl-a.

At 1450, the magnitude of the variable fluorescence can be calculated. For example, the magnitude of the variable fluorescence can be calculated according to the example of FIG. 13. The magnitude of the variable fluorescence can be used, such as at 1462, to correct information obtained from a spectrally-resolved measurement of the magnitude of a Chl-a fluorescence. The variable fluorescence can be used as a correction factor for phytoplankton physiological variability, such as to compensate for physiological regulation in Chl-a fluorescence yield caused by phytoplankton photo-protective mechanisms. Such photo-protective mechanisms can also affect the magnitude of the variable fluorescence. In an example, the ratios obtained using equations (4), or (9), such as the $I_{Chla/R}^v$ and $I_{Chla/R}^g$ parameters of Chl-a concentration, can be normalized to the magnitude of the variable fluorescence to improve the correlation between the SDC retrievals and independent HPLC measurements of pigment concentrations.

In an example, physiological information derived from a temporally-resolved measurement, such as information about the magnitude of the variable fluorescence, can be used to improve an assessment of a characteristic of a fluorescent substance in a liquid sample, such as a quantitative assessment of a chlorophyll concentration, such as can be obtained using a spectrally-resolved measurement. In some cases, a normalization of chlorophyll-a fluorescence to the magnitude of the variable fluorescence, $F_v/F_m$, can be used to minimize or eliminate the adverse effects of the photo-physiological dependence or photo-protective regulation of chlorophyll-a fluorescence intensity on the accuracy of chlorophyll-a concentration assessments, such as can be derived from spectrally-resolved measurements. Thus, using physiological information, such as can be obtained from a temporally-resolved measurement of a water sample, quantitative assessments of some aquatic constituents, such as pigments obtained from a spectrally-resolved measurement of the water sample, can be improved.

Figure 12A:
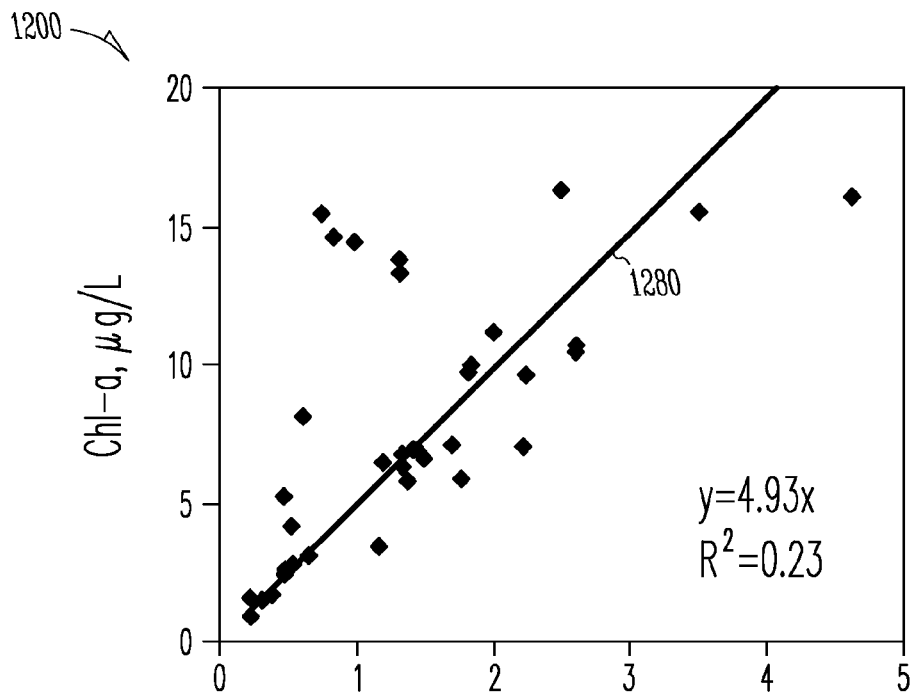
FIGS. 12A and 12B illustrate generally examples of improving the accuracy of in vivo spectral fluorescence assessments of Chl-a concentration using photo-physiological data on variable fluorescence retrieved from temporal measurements of fluorescence induction.
Figure 12B:
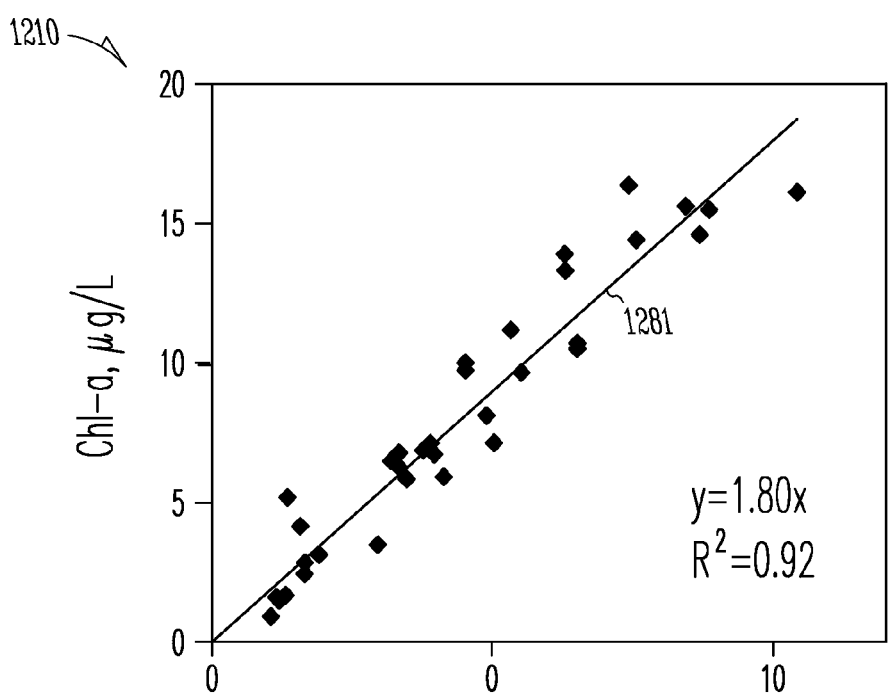

Referring now to the example of FIG. 12A, there is poor correlation ($R^2=0.23$ at 1280) between the ALF underway flow-through spectral measurements of Chl-a fluorescence normalized to the Raman scattering, $I_{Chla/R}^v$, in the Delaware and Chesapeake Bay (horizontal axis) and independent measurements of Chl-a concentration using high-performance liquid chromatography (vertical axis). FIG. 12B illustrates an example of the same data set as shown in FIG. 12A, but the Chl-a fluorescence is normalized to water Raman scattering and the spectrally corrected variable fluorescence magnitudes, $F_v/F_m$, retrieved as described in FIG. 13 from concurrent, temporal fluorescence induction measurements, $F_{PDP}$ (t). In the example of FIG. 12B, there is an improvement in the correlation ($R^2=0.92$ at 1281) between the physiologically corrected spectral fluorescence retrievals and the HPLC measurements of Chl-a concentration. Thus, the example of FIGS. 12A and 12B illustrates generally the potential of using information from temporal measurements to improve retrievals from spectral measurements, such as to improve a quantitative assessment of Chl-a concentration retrieved from spectrally resolved fluorescence measurements.

In an example, normalization can provide the improvement in the correlation with the HPLC measurements of Chl-a concentration because the zeaxanthin cycling, a major photo-protective mechanism of diatoms that often dominate during the coastal and estuarine spring blooms, affects the efficiency of energy transfer from light-harvesting antenna to the photosystem II reaction centers, where the photochemistry occur and from which most of the Chl-a fluorescence originates. More sophisticated approaches can be used, such as in more diverse water types, to improve the spectral assessment of pigment concentration using physiological information retrieved from temporal measurements of fluorescence induction.

Assessment $LSE^v$ Spectral Variability

Development of the SDC analytical algorithms described above was to a large extent built upon a series of ALF field deployments. The objectives were (i) to test the ALF instrument in a broad range of natural aquatic environments and (ii) to develop a simple yet adequate SDC procedure that would provide accurate retrievals of the constituent emission bands from the complex overlapped LSE spectral patterns. Regionally, the ALF deployments included the offshore and coastal zones of the Atlantic and Pacific Oceans, Chesapeake, Del. and Monterey Bays, and a number of estuaries and rivers of the East and West US coast.

Some examples of the $LSE^v$ spectral variability observed during the field measurements are presented in FIGS. 5A-5F along with the SDC analyses of the $LSE^v$ signatures. The legend indicates the measured spectra as $LSE^v$, and the SDC best fits as $Fit^v$, respectively. As evident from FIGS. 5A-5F, in most cases the SDC fits can be almost indistinguishable from the measured spectra except for some minor deviations around the CDOM fluorescence peak. The $LSE^v$ signatures measured in surface off-shore oceanic waters were mostly determined by the overlapping bands of the WR scattering ($S_R^v$), broadband CDOM fluorescence ($F_{CDOM}^v$), and Chl-a fluorescence ($F_{Chla}^v$) (for example, FIG. 5A; Southern California Bight, April 2007). Up to two orders of magnitude of variability in the $F_{CDOM}^v$ intensity relative to the $S_R^v$ peak were observed due to significant variations in the CDOM content in different water types. For example, compare the $LSE^v$ spectra measured in oceanic waters (FIG. 5A), Delaware Bay (FIG. 5B) and Delaware River (FIG. 5F). The $F_{CDOM}^v$ component, such as can be derived from the ALF measurements in the Delaware River, was found to work well in all measured water types, including the offshore oceanic waters, despite the chemical and spectral complexity and variability of CDOM in natural waters. It is believed that the satisfactory SDC performance of the simple single CDOM component, $F_{CDOM}^v$, may be due to the relatively long-wavelength excitation, 405 nm, used in the ALF instrument. Chl-a fluorescence was a major contributor to the $LSE^v$ in the red portion of the spectra. Though the $F_{Chla}^v$ peak was located around 680 nm in most of the $LSE^v$ signatures, both blue- and red-shifts in the peak location, e.g. 677 to 685 nm, accompanied by changes in its spectral shape were detected. Most of the spectral variability in the Chl-a fluorescence can be reasonably well described via linear scaling the $E_{C1}$, $E_{C2}$ and $E_{C3}$ SDC components (see equation (3)).

Along with the Chl-a fluorescence, three other spectrally distinct emission bands can be detected in the red portion of the $LSE^v$ spectra during the ALF field deployments. The underway ALF measurements in the Delaware Bay revealed an intense emission peak at 644 nm that significantly exceeded the Chl-a fluorescence (see, e.g., FIG. 5B). Similar, though less extreme, spectral patterns were also observed during the underway measurements in the coastal zone of the Middle-Atlantic Bight near the Chincoteague Island. Another spectral band with maximum around 625 nm was detected during the ALF underway measurements in the surface waters of the Delaware Bay (FIG. 5C). The emission band peaking at 662 nm was observed in the $LSE^v$ signatures at various locations during the ALF underway measurements (for example, see FIG. 5D). Finally, the broadband red emission, such as ranging from 610 to 700 nm, which seemed to be composed of several overlapped emission bands, was consistently detected in the $LSE^v$ spectra of the water samples taken in the euphotic layer below the Chl-a maximum in the Southern California Bight, California Current and in the Middle Atlantic Bight (for example, see FIG. 5E). The $E_{R1}$, $E_{R2}$, and $E_{R3}$ SDC spectral components were derived from the $LSE^v$ field data (see above) to account for the observed variability in the red portion of the $LSE^v$ signatures. As evident from FIGS. 5A-5F, they describe well not only the individual spectral bands detected in the surface waters (see, e.g., FIGS. 5B, 5C, and 5D), but also the broadband red emission observed in the water samples taken from the bottom of the euphotic layer (see, e.g., FIG. 5E).

The origin of the red emission bands peaking at 625, 644 and 662 nm in the $LSE^v$ spectra stimulated to 405 nm remains to be identified. Based on their spectral location and characteristic shape, they can be interpreted as fluorescence of PBP pigments. Indeed, the cryptophyte-specific phycoerythrin PE566 has an in vivo emission peak around 620 nm. The fluorescence maximum of phycocyanin, an accessory PBP pigment present in cyanobacteria and cryptophytes, is located in the 642-645 nm range, while some spectral forms of cyanobacterial allophycocyanin have their emission peaks around 662 nm. Despite the spectral similarity, the PBP origin of the red fluorescence in the $LSE^v$ spectra seems to be doubtful. Indeed, the SDC analysis of the $LSE^g$ signatures has detected no respective red fluorescence, though the green excitation is more efficient than the violet one in stimulating the in vivo PBP emission. Also, no significant correlation was found between the red emission detected in the $LSE^v$ spectra and the PE fluorescence observed in the $LSE^g$ signatures. It is believed that the red emission detected in some $LSE^v$ signatures may originate from a dysfunctional or degrading photosynthetic apparatus of phytoplankton. In particular, the 644 nm emission peak can be attributed to the accessory chlorophyll-c (Chl-c) from poorly-functional light-harvesting complexes. The weak in vivo Chl-c fluorescence peaking at 644 nm is from photosynthetically functional phytoplankton. Regarding the emission at 662 nm, similar spectral features can be observed in the $LSE^{405}$ signatures of senescent phytoplankton cultures, consistently with the presumable photodegradation origin of the emission. Similar investigations can be used to identify the red emission bands observed in the field.

$LSE^g$ Spectral Variability

Some characteristic spectral features of the $LSE^g$ signatures of natural waters are illustrated in FIGS. 6A-6F. Despite their significant variability, the SDC best fits, $Fit^g$, well reproduce the measured $LSE^g$ spectra. The WR scattering band, $S_R^g$, has its major maximum at 651 nm (the Raman shift $\upsilon_{max}=3440$ cm$^{-1}$) and is a dominant or subdominant spectral component in most of the $LSE^g$ spectra. Two less intense WR bands, 1600 and 2200 cm$^{-1}$, also can be seen in the $LSE^g$ spectra at 583 and 602 nm in FIG. 6A. Although their intensities are only a few percent of the major Raman peak at 651 nm, they can play important role in formation of the $LSE^g$ patterns in the oceanic waters, where CDOM and PE fluorescence are often comparable to the intensity of these weak Raman bands (see, e.g., FIG. 6A).

As evident from FIGS. 6A-6F, Chl-a fluorescence can be an important contributor to the $LSE^g$ spectra of natural waters. Significant variability in the location (e.g., 673-686 nm) and spectral shape of a Chl-a fluorescence band was observed during the ALF field measurements. For example, a short-wavelength spectral shift in the Chl-a fluorescence was detected during the dinoflagellate blooms in Monterey Bay and adjacent Elkhorn Slough (see, e.g., FIG. 6B, where $\lambda_{Chla}^g=673$ nm), in the lower Chesapeake Bay and adjacent York River (see, e.g, FIG. 6E, where $\lambda_{Chla}^g=676$ nm), and in the Pacific coastal zone of San Diego (where $\lambda_{Chla}^g=675$ nm). High linear anti-correlation ($R^2=0.90$) between the blue shift and decline in variable fluorescence observed in the Monterey Bay suggests a potential physiological origin of the spectral shift. For instance, the dinoflagellate-specific water soluble peridinin-chlorophyll-protein light-harvesting complexes (sPCP LHC) do not fluoresce in the normally functional PSII, but have their sPCP-specific Chl-a fluorescence peak around 673-676 nm. A decrease in the efficiency of energy transfer from the sPCP LHC to the PSII core might lead to appearance of the sPCP Chl-a fluorescence accompanied by a decline in Chl-a fluorescence from the core, which could result in the blue shift of the overall Chl-a peak. The fact that the blue shift was stronger with the green vs. violet excitation is consistent with such an assumption, because the peridinin absorption peak locates in the green spectral region.

The red spectral shifts in Chl-a fluorescence were also observed during the ALF field deployments. For example, the Chl-a emission peaking at 686 nm with the shoulder at 692 nm was detected in both $LSE^v$ and $LSE^g$ spectra measured in the Delaware River (see, e.g., FIGS. 5F and 6C). As evident from the SDC examples presented in FIGS. 5A-5F and 6A-6F, the observed field-based spectral variability in Chl-a fluorescence can be reasonably well described via SDC linear scaling of the $E_{C1}$, $E_{C2}$, and $E_{C3}$ spectral components. The origin of the spectral variability may be driven by both structural and physiological changes in the algae, among other factors.

Figure 10A:
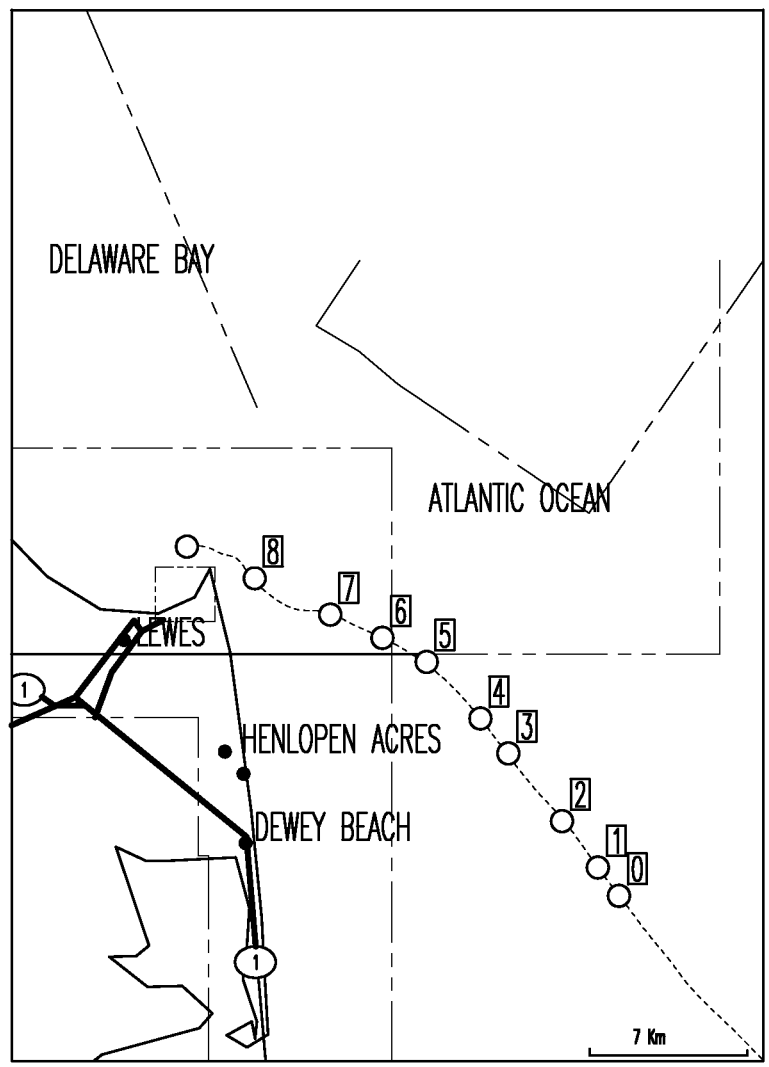

A distinct feature of the $LSE^g$ signatures is the significant variability in the 540-620 nm portions of the spectra mainly caused by the overlap of the PE and CDOM fluorescence bands (see, e.g., FIGS. 6A-6F). The ALF/SDC analyses often detect significant cryptophyte-specific fluorescence, $F_{PE3}^g$ ($\lambda_{max}=589$ nm) in this spectral range of the $LSE^g$ spectra measured in various coastal, estuarine and fresh waters. For example, see FIGS. 6D and 6E measured respectively near Point Conception in the Southern California Bight and in the lower Chesapeake Bay. The significant $F_{PE3}^g$ fluorescence was also detected in the upper and middle portions of the Delaware Bay, in the York River (Va.), and in the Sough Slough estuary (Oregon). The cyanobacterial high PUB/PEB (Type 1) PE fluorescence, $F_{PE1}^g$ ($\lambda_{max}=565$ nm) dominated in the yellow-orange $LSE^g$ region in the samples obtained in the zone of Middle Atlantic Bight adjacent to the Delaware Bay (FIG. 6F); similarly significant, though less intense, $F_{PE1}^g$ fluorescence was consistently detected in the offshore waters of the Middle Atlantic Bight (see a transect distribution of $I_{PE1/R}^g$ in FIG. 10) and in the California current. Fluorescence of low PUB/PEB, Type 2 spectral form of cyanobacterial PE, $F_{PE2}{}^g$ ($\lambda_{max}$=578 nm), was found to often accompany the $F_{PE1}{}^g$ and/or $F_{PE3}{}^g$ emission in coastal, bay and estuarine environments (see, e.g., FIGS. 6E and 6F). It dominated in the LSE$^g$ spectra between 540 and 620 nm in the lower Chesapeake Bay (FIG. 6E) and coastal waters of Hawaii Island; the significant $F_{PE2}{}^g$ emission was also found in the LSE$^g$ spectra measured in the lower Delaware Bay and near-shore Pacific zone of California.

Figure 6A:
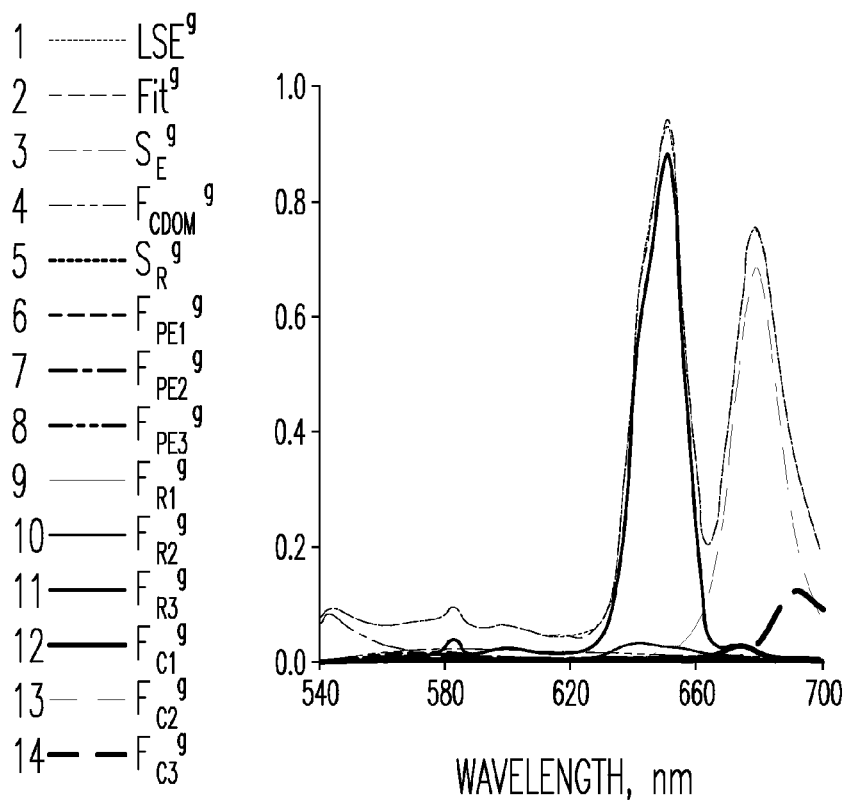
FIGS. 6A, 6B, 6C, 6D, 6E, and 6F illustrate generally variability in the $LSE^g$ spectra measured in diverse surface waters with green laser excitation.
Figure 6B:
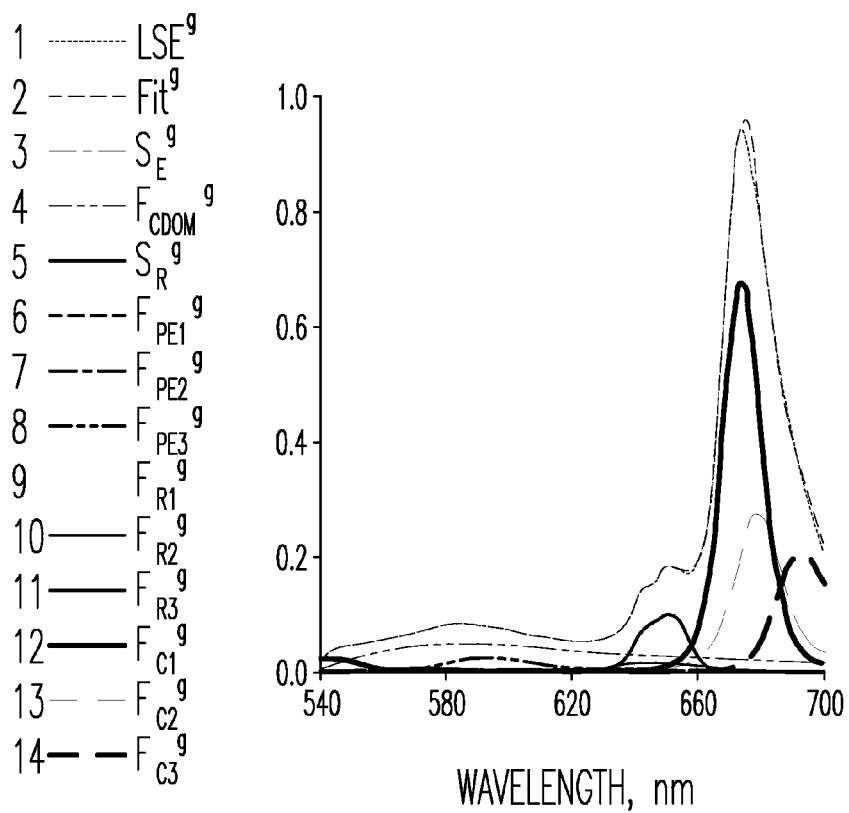
Figure 6C:
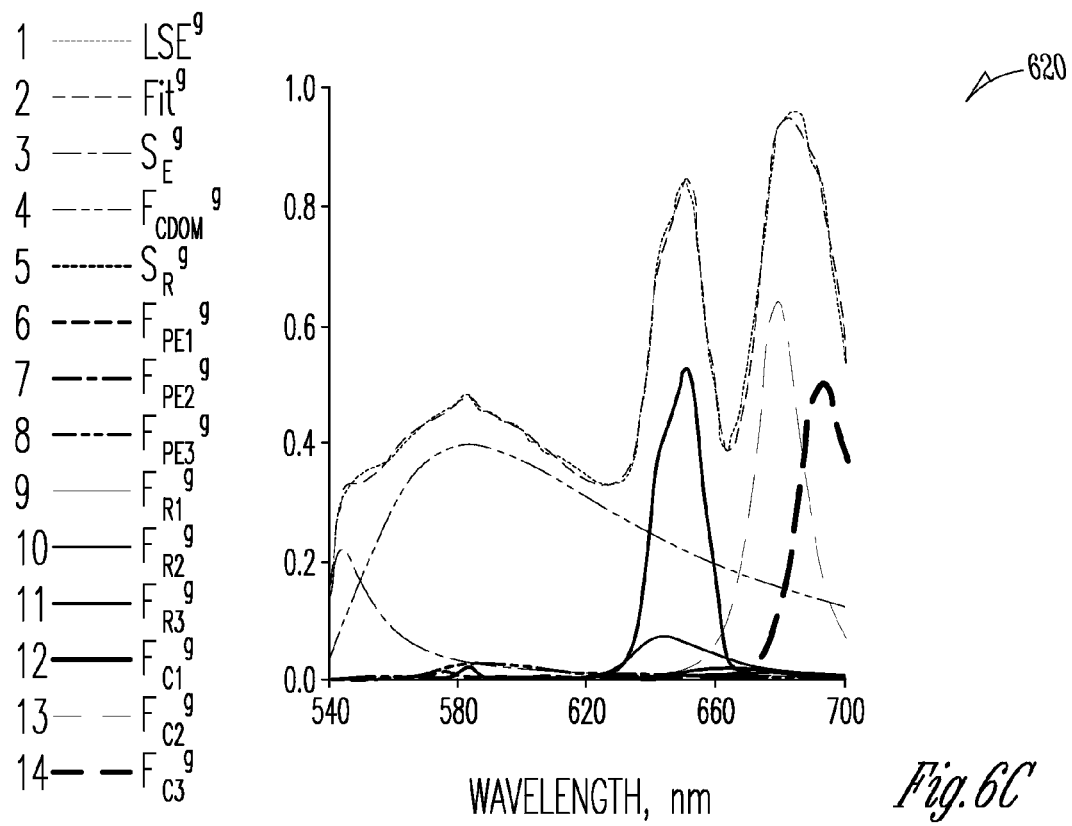
Figure 6D:
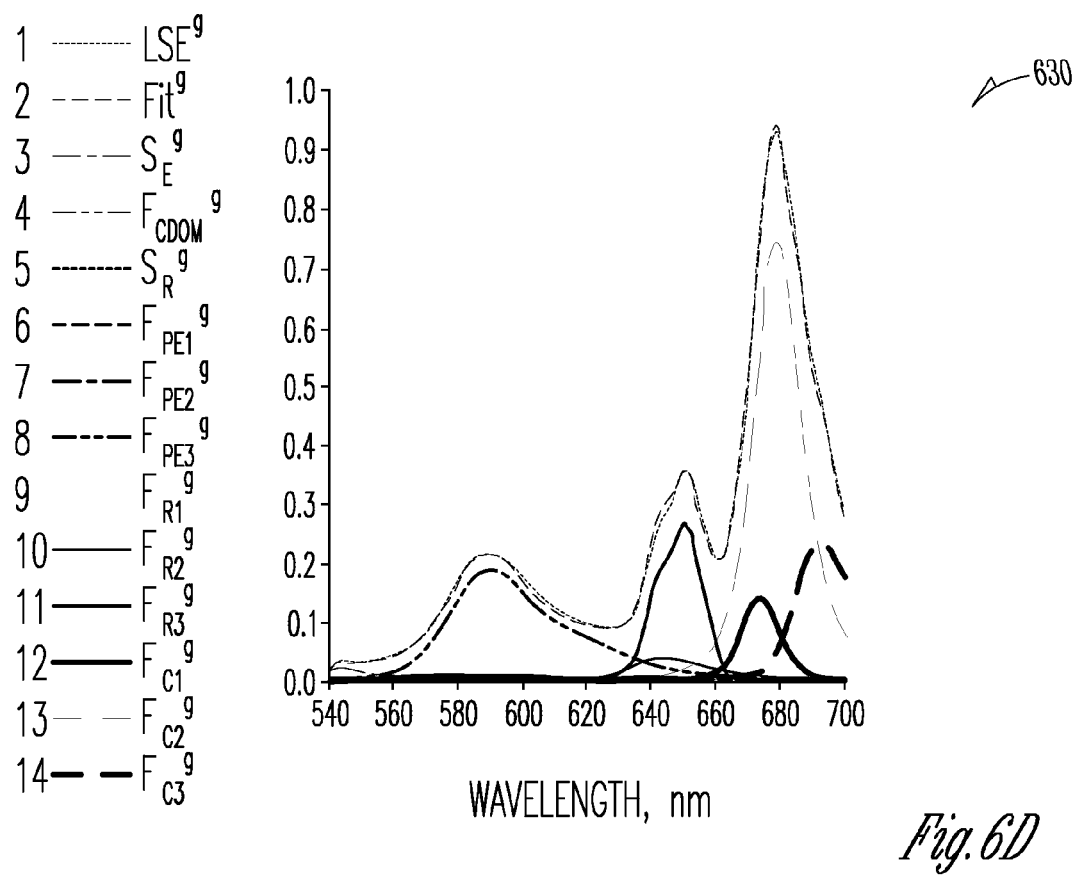
Figure 6E:
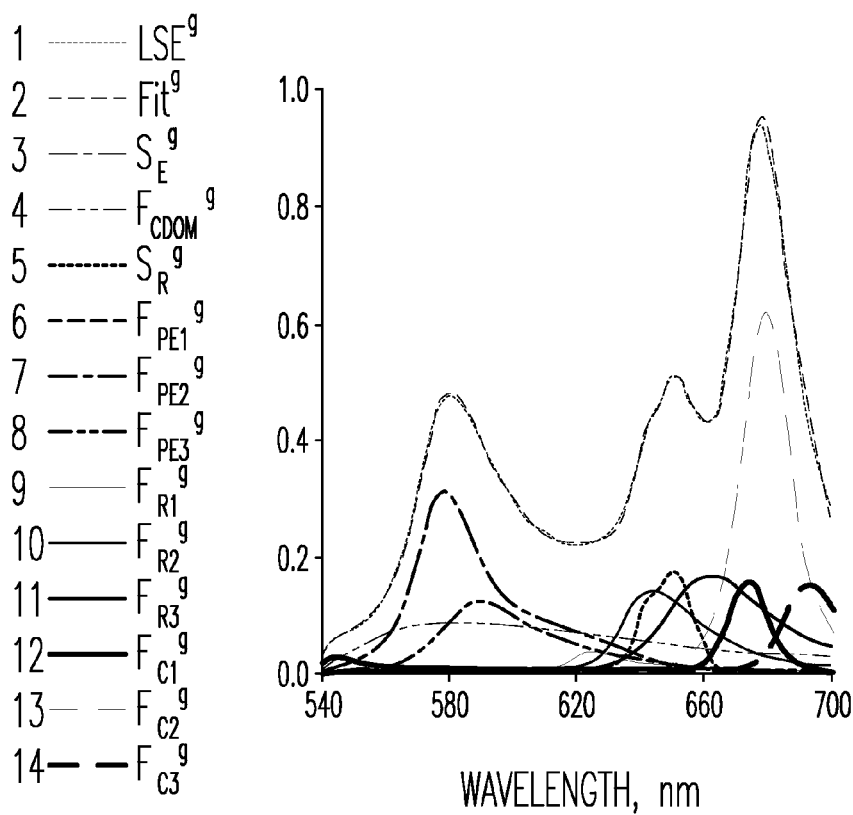
Figure 6F:
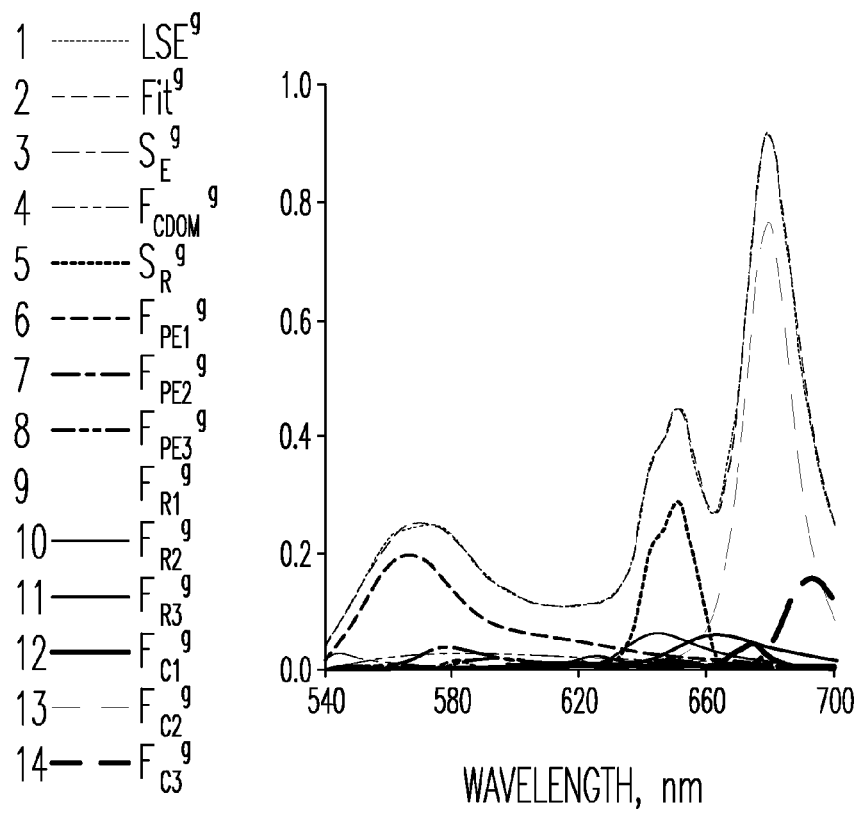

The broadband CDOM emission, $F_{CDOM}{}^g$, though less intense vs. the WR band as compared to the LSE$^v$ signatures, still played an important role in the formation of the orange-red portion of the LSE$^g$ spectra not only in estuaries, but in all the surveyed water types, including offshore oceanic waters. Its intensity was often comparable to the PE fluorescence in the bay and estuarine waters (e.g., FIG. 6E), and could dominate over the PE emission peaks in both oceanic (FIG. 6A) and fresh waters. For example, in the Delaware River (FIG. 6C), about 85% of the LSE$^{532}$ intensity in the 570-620 nm range, which can be interpreted as the PE fluorescence, was actually formed by the CDOM emission (confirmed by the spectral measurement of the sample filtrates). In the CDOM-rich waters, the intense CDOM fluorescence can provide significant background contributions even in the red portion of the LSE$^g$ spectra that needs to be accounted for correct assessment of the red emission bands, such as WR scattering or Chl-a fluorescence (FIGS. 6C and 6E).

The SDC analysis of the LSE$^g$ field measurements has revealed that the linear scaling of the SDC spectral components, attributed to the WR scattering and fluorescence of Chl-a, PE and CDOM, cannot entirely account for the complex spectral patterns observed in the red portion of the LSE$^g$ spectra. The SDC mismatch was particularly evident for the LSE$^g$ signatures that showed the intense PE fluorescence, thus indicating a significant abundance of PBP-containing cryptophytes or/and cyanobacteria. For evaluation, three additional spectral components, $E_{R1}$, $E_{R2}$ and $E_{R3}$, which were originally derived from the LSE$^v$ field data, were included in the SDC procedure described by equation (5). This was done to incorporate the best fitting three additional red spectral bands, $F_{R1}{}^g$, $F_{R2}{}^g$ and $F_{R3}{}^g$ (see equation (6)). The SDC analysis has shown that the $F_{R1}{}^g$ band played a rather insignificant role in the LSE$^g$ formation for most of the explored water types; while the $F_{R2}{}^g$ and $F_{R3}{}^g$ SDC spectral components provided variable contributions in various waters, remaining subdominant relative to the major peaks of WR scattering at 651 nm, Chl-a and PE fluorescence (see, e.g., FIG. 6). The LSE$^g$ patterns observed in the lower Chesapeake Bay (FIG. 6E) constituted an exception, as all three red emission bands provided significant contributions to the LSE$^g$ formation, comparable to the usually dominant band of WR scattering, $S_R{}^g$. The correlation patterns with the group-specific spectral types of PE emission suggest that in the areas abundant with PBP-containing cyanobacteria and cryptophytes the $F_{R2}{}^g$ and $F_{R3}{}^g$ SDC retrievals may be associated with the phycocyanin and allophycocyanin fluorescence.

Correlation Analysis of the SDC Retrievals

To evaluate ALF capacity for quantitative assessments of aquatic fluorescent constituents, the ALF spectral retrievals were compared with HPLC pigment analyses. The $I_{Chla/R}{}^v$ and $I_{Chla/R}{}^g$ SDC retrievals (see Eqs. 4 and 9) showed high correlation with the HPLC assessments of Chl-a concentration in a range of water types surveyed during the ALF field deployments. For example, FIG. 7A displays the linear correlation ($R^2$=0.93) 760 between the $I_{Chla/R}{}^v$ retrievals and the HPLC measurements of total Chl-a conducted in the Middle Atlantic Bight, Chesapeake and Delaware Bays, in the Sough Slough estuary (Oregon) and York River (Va.). Similarly high correlation ($R^2$=0.92) was observed between the $I_{Chla/R}{}^g$ magnitudes and the HPLC Chl-a data for the same integrated data set. The WR normalization, as well as the relatively short (<1 cm) path of the excitation and emission light in the measurement cell, likely provided for the robustness of the correlation between Chl-a fluorescence and concentration up to 20 mg m$^{-3}$ despite the significant variability in turbidity (up to 10 NTU as measured in the York River) within the data set.

Assuming that the CDOM fluorescence stimulated at 405 and 532 nm originates from the same organic chromophores, comparison of the $I_{CDOM/R}{}^v$ and $I_{CDOM/R}{}^g$ magnitudes can provide a good overall test for the ALF SDC analysis. Indeed, the CDOM and WR emission bands are located in different portions of the LSE$^v$ and LSE$^g$ spectra and have different and variable patterns of spectral overlap with the emission bands of other water constituents (FIGS. 5A-5F and 6A-6F). In spectrally complex environments, the peak magnitudes of the CDOM and WR emission bands often constitute only a fraction of the LSE intensity at their peak locations (for example, see FIGS. 5B, 5C, 5F, 6A, 6B, 6C, 6E, and 6F). Nonetheless, the correlation analysis yielded consistently high linear correlations between the $I_{CDOM/R}{}^v$ and $I_{CDOM/R}{}^g$ retrievals in various water types examined. For example, FIG. 7B displays their correlation for the combined data set measured in the Delaware Bay and adjacent coastal and offshore areas of the Middle Atlantic Bight.

Figure 8A:
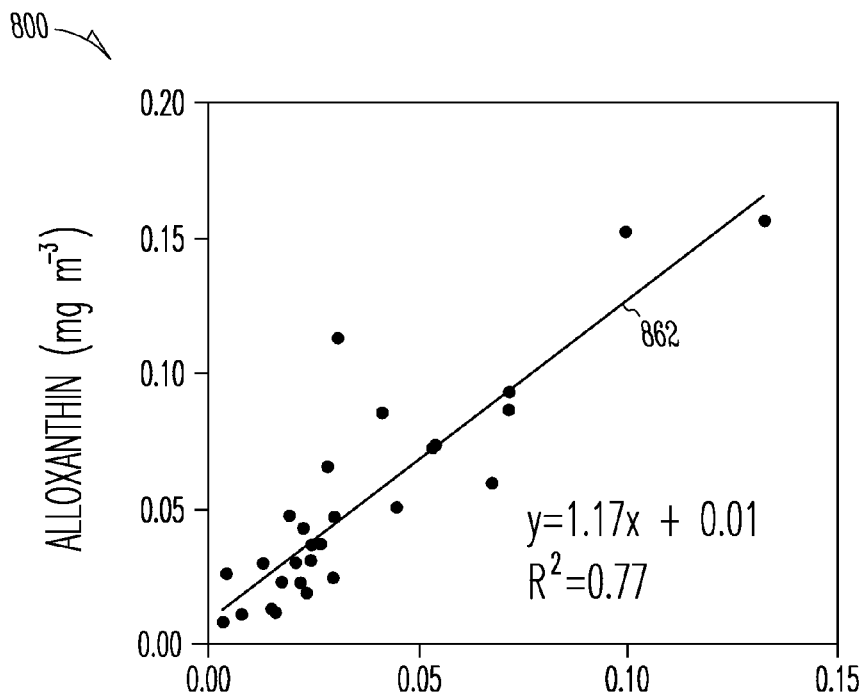
FIGS. 8A, 8B, 8C, and 8D illustrate generally correlations between the group-specific PE spectral indices retrieved by the SDC LSE analysis using the ALF and independent HPLC measurements of alloxanthin and zeaxanthin, the carotenoid biomarkers for the cryptophytes and cyanobacteria, respectively.
Figure 8B:
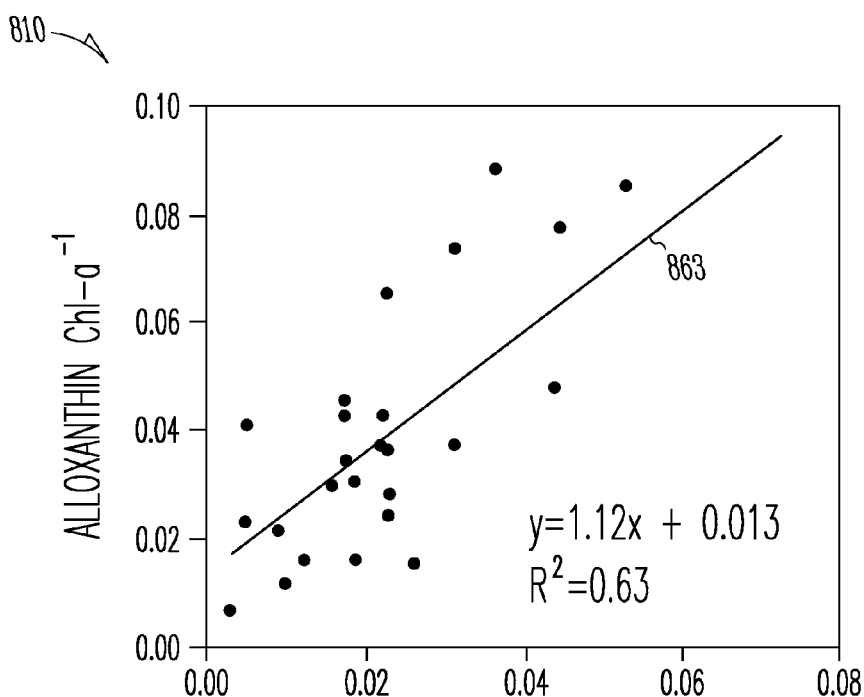
Figure 8C:
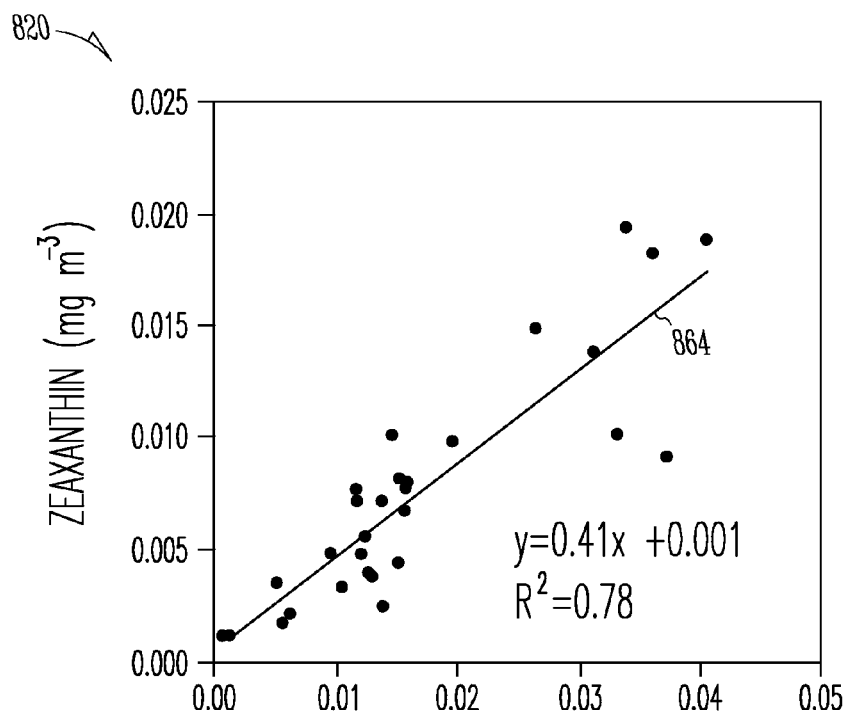

To evaluate the ALF/SDC potential for assessment of the PBP-containing photosynthesizing organisms in the mixed phototrophic populations, we compared ALF SDC retrievals of the group-specific PE spectral indices with independent HPLC measurements of alloxanthin and zeaxanthin, the carotenoid biomarkers for the cryptophytes and cyanobacteria, respectively. FIG. 8 displays the correlations for the water samples collected in the Southern California Bight. High linear correlation, $R^2$=0.77 at 862, was found between the magnitudes of the $I_{PE3/R}{}^g$ fluorescence parameter and the alloxanthin concentration (FIG. 8A) despite its relatively low magnitudes. A similar linear correlation, $R^2$=0.78 at 864, was observed between the $I_{PE1/R}{}^g$ values and the zeaxanthin concentration (FIG. 8C). It is believed that these data demonstrate that the ALF/SDC retrievals provide potential for detection, discrimination and quantitative assessment of cryptophytes and cyanobacteria in natural aquatic environments.

Assuming the alloxanthin, zeaxanthin and Chl-a concentrations as proxies for biomass of cryptophytes, cyanobacteria and total population of the photosynthesizing microorganisms, respectively, the alloxanthin/Chl-a and zeaxanthin/Chl-a ratios can be considered as first-order indices for assessment of a relative abundance of cryptophytes and cyanobacteria in the mixed phototrophic populations. Evaluation of the relationships between these pigment indexes and respective fluorescence parameters can be yielded by the SDC LSE analysis. For the data sets displayed in FIGS. 8A and 8C, the correlations between the $I_{PE3/Chla}$ vs. alloxanthin/Chl-a ratio (FIG. 8B) and $I_{PE1/Chla}$ vs. zeaxanthin/Chl-a ratio (FIG. 8D) were somewhat lower ($R^2$=0.63 at 863), which can be explained by the higher errors in the ratios vs. the absolute magnitudes of fluorescence and HPLC retrievals (FIGS. 8A and 8C). The magnitudes of both pigment and fluorescence ratios were in the range of a few percent, which might also affect the correlations. Nonetheless, the trends observed in FIGS. 8B and 8D indicate the potential of the ALF/SDC technique for structural analysis of the mixed algal populations.

Thus, fluorescent characterization of aquatic constituents can include characteristics such as a quantitative assessment of phycobiliprotein-containing groups of photosynthesizing microorganisms in mixed phototrophic populations present in a water sample, such as including a basic structural characterization of the populations. For example, FIGS. 8A and 8C illustrate generally examples of assessing PE3- and PE1-containing cryptophytes and cyanobacteria, respectively. The SDC analysis of the LSE spectral measurements can yield magnitudes of group-specific $I_{PE3/R}^g$ and $I_{PE1/R}^g$ fluorescent parameters, such as using equation (10). These fluorescence parameters can show good correlation with independent measurements of the respective group-specific pigment biomarkers that are generally accepted as indices of biomass for these groups of photosynthesizing microorganisms.

Figure 8D:
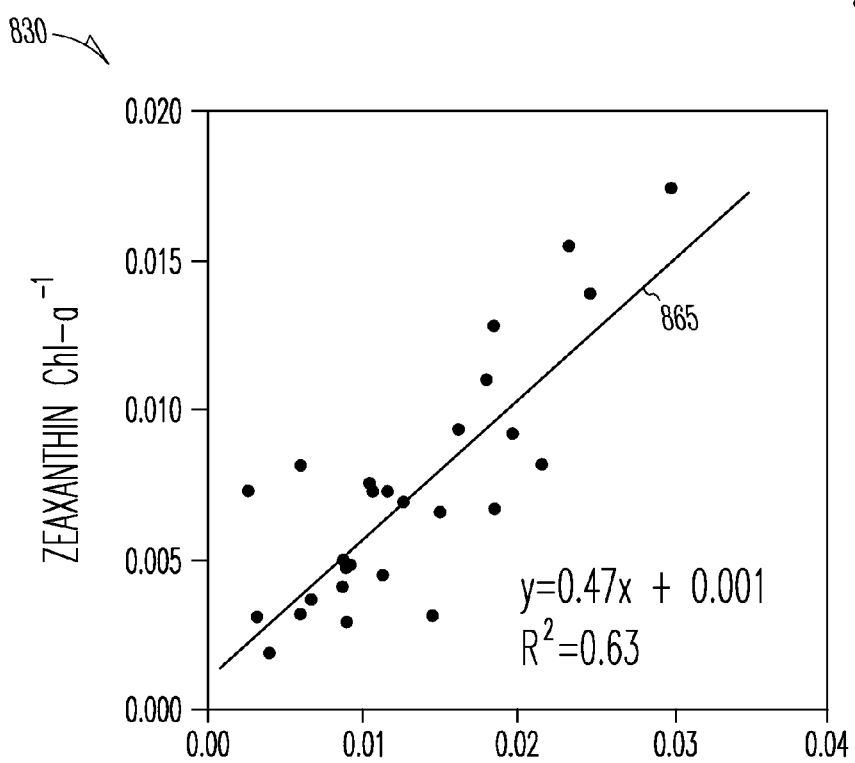

The PE group-specific fluorescence can be a useful index to quantitatively assess the respective PBP-containing group in the water sample. Chl-a can be taken as an index of total biomass of photosynthesizing organisms present in the same water sample. Thus, the ratio $I_{PE/Chla}$ can be used as an index to indicate a relative abundance of the PE-containing group in mixed populations of photosynthesizing organisms in a water sample. FIGS. 8B and 8D illustrate generally examples of structural characterization of photosynthesizing populations in a natural water sample that contain the PBP-containing groups of microorganisms, cryptophytes and blue-water cyanobacteria. In the examples of FIGS. 8B and 8D, the SDC analysis of the LSE spectral measurements can yield, such as using equation (10), the ratios of the magnitudes of group-specific PE fluorescence bands to Chl-a fluorescence, such as $I_{PE3/Chla}$ and $I_{PE1/Chla}$. These fluorescent parameters can show satisfactory correlation with independent measurements of the ratios of concentrations of their respective group-specific pigment biomarkers and Chl-a.

For example, $I_{PE3/Chla}$ can be used to indicate a relative population of cryptophytes (see, e.g., FIG. 8C). In the example of FIG. 8C, alloxanthin can be used as an independent index of cryptophyte abundance. Plotting $I_{PE3/Chla}^g$ against alloxanthin can yield a conversion coefficient (e.g., 1.12 in the example of FIG. 8C), such as can be used to convert the dimensionless fluorescence parameter $I_{PE3/Chla}^g$ into the Alloxanthin/Chl-a ratio, an index based on commonly accepted units, such as alloxanthin and chlorophyll-a concentrations. In the example, the correlation plot 8C can be used as a calibration procedure.

Spectral Correction of Variable Fluorescence

As described above, the real-time SDC $LSE^v$ analysis can yield the $I_{NC/Chla}$ parameter to assess non-Chl-a background emission, $B_{NC}$, in the area of a Chl-a fluorescence peak. The latter can then be subtracted from the PDP induction curve to retrieve a spectrally-corrected variable fluorescence (Eqs. 12-14). The ALF field spectral measurements have shown that the magnitudes of $B_{NC}$ and relevant $I_{NC/Chla}$ parameters can exhibit significant variations in natural aquatic environments. For example, in surface oceanic waters the $I_{NC/Chla}$ magnitude can vary from a few percent (see, e.g., FIG. 5A) to approximately 25 percent, depending on the relationship between the CDOM and Chl-a fluorescence intensity. The non-Chl-a red fluorescence bands, such as $F_{R2}$ and/or $F_{R3}$, can provide a comparable to or greater than CDOM contribution in the spectral range of the Chl-a fluorescence peak (see, e.g., FIGS. 5C and 5D, respectively). The $I_{NC/Chla}$ magnitude can reach up to 50-100% in the CDOM-rich freshwater or estuarine environments (see, e.g., FIG. 5F) or at the bottom of euphotic layer (see, e.g., FIG. 5E). In the latter case, a decline in the Chl-a fluorescence is typically accompanied by an increase in CDOM fluorescence and the broadband red emission of other, non-Chl-a constituents (see, e.g., FIG. 5E and the vertical profiles of $I_{CDOM/R}^v$ and $I_{R3/R}^v$ in FIG. 11A). In extreme cases, the non-Chl-a red background emission can significantly exceed the peak magnitudes of the Chl-a and CDOM fluorescence (see, e.g., FIG. 5B).

Figure 9A:
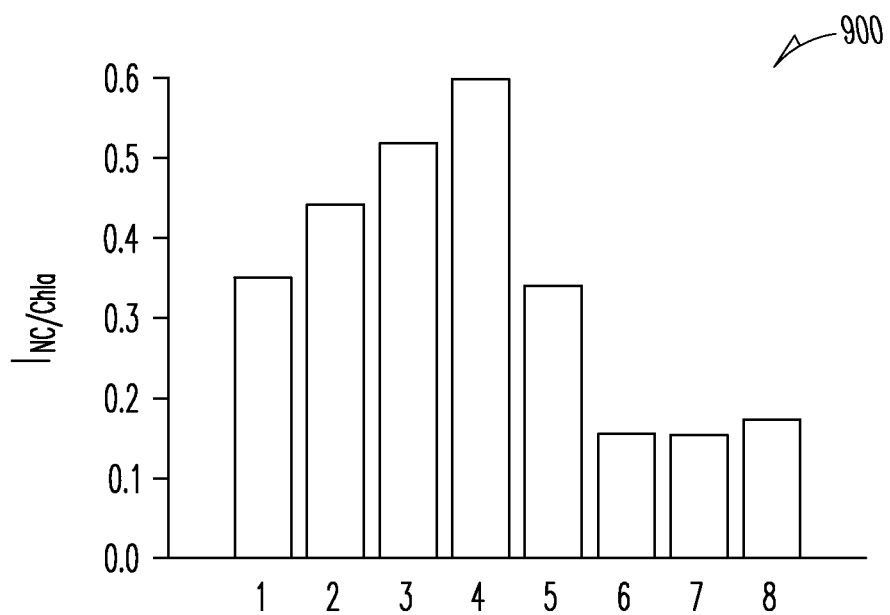
FIG. 9A illustrates generally an example of SDC retrievals of $I_{NC/Chla}$, the ratio of the non-Chl-a background emission to the actual intensity of Chl-a fluorescence in the $LSE^v$ spectrum, at eight stations in the Delaware River.
Figure 9B:
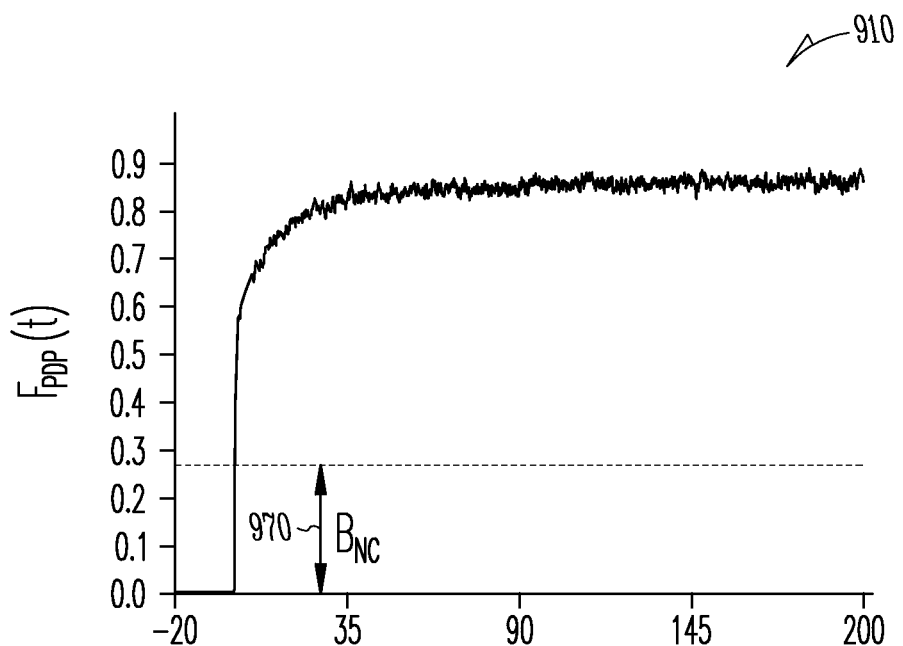
FIG. 9B illustrates generally fluorescence induction, $F_{PDP}$(t), measured by the ALF instrument at station 4.
Figure 9C:
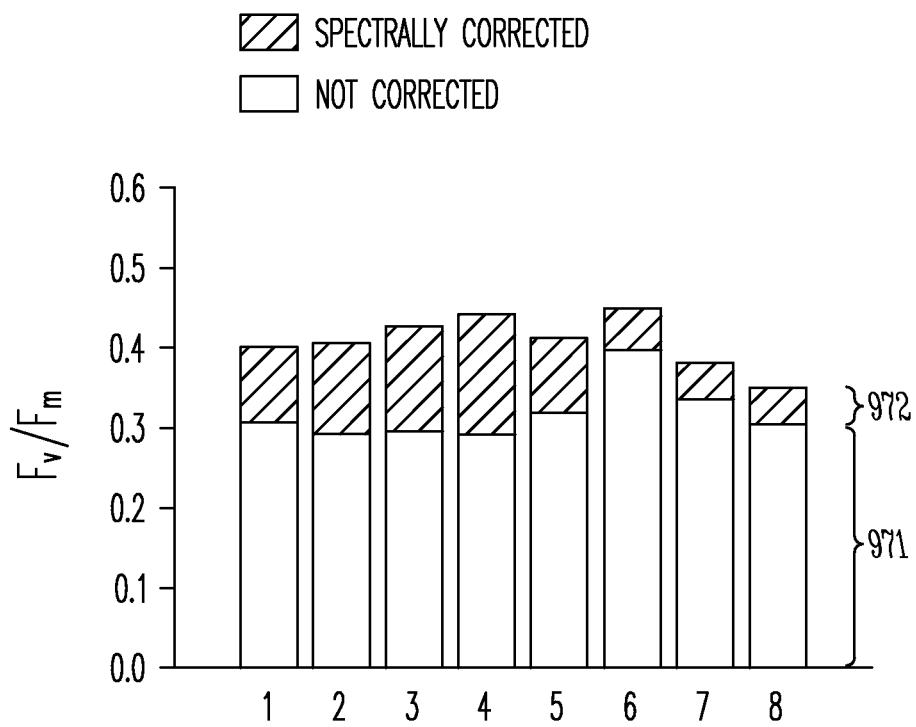
FIG. 9C illustrates generally background emission subtraction from measured induction curves.

The ALF spectral correction of variable fluorescence can be configured to automatically account for a variable $B_{NC}$ background in an analyzed water sample, thus yielding more accurate assessments of variable fluorescence in spectrally complex aquatic environments. To illustrate the importance of the spectral correction, FIGS. 9A and 9C illustrate the $I_{NC/Chla}$ magnitudes and the comparison of the $F_v/F_m$ values calculated with and without the correction for the $B_{NC}$ parameter for the water samples taken in the Delaware River between Trenton, N.J., and the river mouth adjacent to the Delaware Bay. As evident from these data, up to 35% underestimation of the $F_v/F_m$ magnitude can occur, such as without the spectral correction due to the high CDOM content in the turbid waters. In the example of FIG. 9C, compare $F_v/F_m=0.29$ vs. 0.45 at station 4 in the middle of the transect. In addition, $F_v/F_m$ values as high as 0.65 were observed after the spectral correction during a phytoplankton spring bloom. The ALF spectral correction of variable fluorescence can be automatically and routinely conducted in real time during discrete sample analyses and during underway shipboard measurements (see, e.g., the spectrally corrected $F_v/F_m$ transect data in FIG. 10). The ALF system requires no filtration or other treatment of the sample, and can be implemented in various instrument configurations and settings potentially capable of the broadband SDC spectral measurements, including implementations of in situ and airborne sensors of variable fluorescence.

ALF Transect Measurements

A significant amount of the ALF underway flow-through measurements onboard research ships and small vessels were acquired during the instrument deployments in diverse water types. To illustrate the analytical capabilities of the ALF/SDC underway analysis, we present an example of the transect measurements conducted in the coastal zone of the Middle-Atlantic Bight adjacent to the Delaware Bay. Distributions of the SDC-retrieved fluorescent parameters are displayed in FIG. 10B; the major transect features are marked with numbers to relate them with their spatial locations respectively numbered on the map in FIG. 10A. An arrow in FIG. 10B marks a technical break in the data acquisition occurred between points 6 and 7. The $I_{Chla/R}^v$ values have been converted into the units of Chl-a concentration (right vertical axis in FIG. 10B) based on the linear correlation displayed in FIG. 7A. Magnitudes of the other ALF variables, including the spectrally-corrected variable fluorescence, $F_v/F_m$ can be assessed using the left axis of the plot. The $F_v/F_m$ values varied in the 0.3-0.4 range along the entire transect thus showing a somewhat depressed physiological status of the phytoplankton population. Seven Chl-a peaks, ranging from 5 to 13 mg m$^{-3}$, were detected along the transect indicating costal mesoscale variability in phytoplankton biomass. As evident from the $I_{CDOM/R}^v$ distribution, the CDOM spatial variability followed closely the Chl-a spatial patterns suggesting a biological origin of CDOM in the surveyed area. The PBP-containing cryptophytes, indexed by the $I_{PE3/R}^g$ fluorescence parameter, showed quite patchy and somewhat distinct spatial patterns, compared to those of Chl-a, reaching the highest concentration in the DB mouth (see points 1, 2, 4 and 8 in FIG. 10A). By contrast, the high PUB/PEB PE-containing cyanobacteria, indexed by the $I_{PE1/R}^g$ fluorescence parameter, had their highest concentration in the coastal zone at point 5, with several smaller sub-peaks around points 0, 1, 2, and 8. The low PUB/PEB PE-containing cyanobacteria, characterized by the $I_{PE2/R}^g$ distribution, showed spatial patterns well correlated with Chl-a; they were most abundant in the Delaware Bay mouth (points 7-8), but also showed patchy structures in the adjacent section of the transect (points 0-2, 3-4, and 6).

Along with the characterization of pigment biomass, the ALF/SDC analysis can illustrate significant structural variability in the mixed population of phytoplankton and cyanobacteria in the surveyed area. The cryptophytes were not detected along the initial, offshore portion of the transect and represented a relatively small fraction of the phototrophic community in the coastal zone of the Middle Atlantic Bight. This was indicated by the magnitudes of the $I_{PE3/Chla}$ parameter that were below 0.05 along the transect everywhere except the sharp peak around point 1, where they reached 0.1 (not displayed in FIG. 10B). A similar range of the $I_{PE3/Chla}$ variability was observed in the Southern California Bight and corresponded to the alloxanthin/Chl-a ratio below 0.1 (see FIG. 8B). By contrast, the high PUB/PEB PE-containing cyanobacteria were more abundant in the populations along the offshore and initial coastal portions of the transect as indexed by the $I_{PE1/Chla}$ magnitudes that reached 0.16 at point 5 in FIG. 10B, one order of magnitude above the highest $I_{PE1/Chla}$ values observed in the Southern California Bight (FIG. 8D). In the Delaware Bay mouth (points 7-8 in FIG. 10B), their fraction exhibited a very sharp decline with the $I_{PE1/Chla}$ values below 0.03. Within the cyanobacterial group, the high PUB/PEB PE spectral type was overwhelmingly dominant in the offshore waters and around point 5 in FIG. 10B, as indicated by $I_{PE1/PE2}$ retrievals that vary from about 2 to 3.5.

Vertical Distributions of Fluorescence Constituents

Figure 11A:
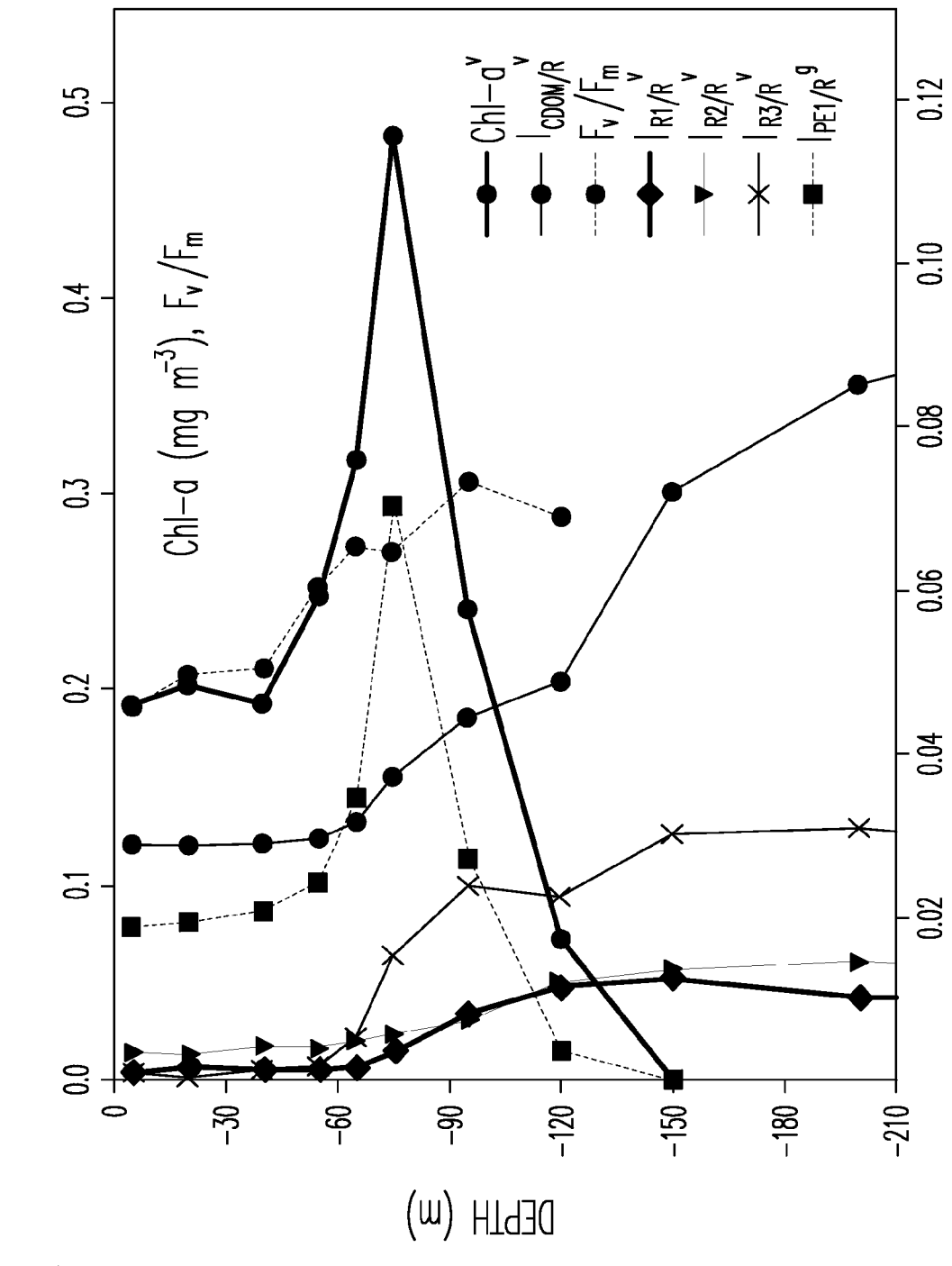
FIGS. 11A and 11B illustrate generally examples of vertical profiles of fluorescence parameters in the euphotic layer retrieved from the ALF sample measurements.
Figure 11B:
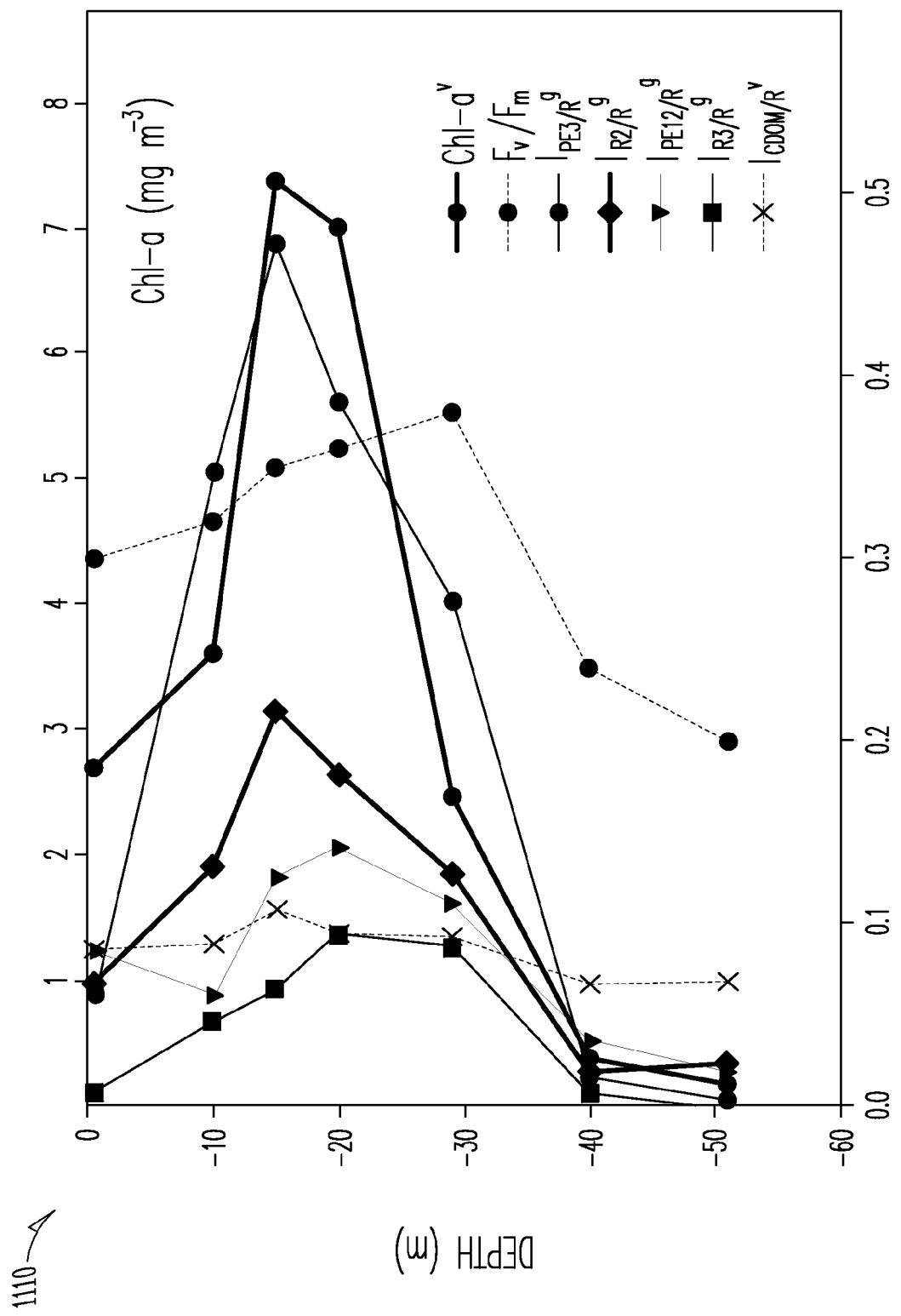

The ALF/SDC suite can provide shipboard underway characterization of aquatic constituents in the surface waters, and it can also provide useful complementary information via laboratory and field analyses of discrete water samples. Two examples of the vertical distributions of the fluorescent constituents, compiled using the ALF analysis of the dark-adapted water samples collected at various depths in the offshore and coastal oceanic waters, are illustrated in FIGS. 11A and 11B. The upper horizontal scale in FIGS. 11A and 11B displays Chl-a concentrations based on the $I_{Chla/R}^v$ regionally-analyzed correlation with the HPLC pigment data.

In the offshore waters of the California current (FIG. 11A), biomass of phototropic phytoplankton and Type1, high PUB/PEB cyanobacteria (indexed by the $I_{Chla/R}^v$ and $I_{PE1/R}^g$ magnitudes, respectively) had almost identical vertical distributions, showing their gradual buildup with depth in the upper 50 m followed by a sharp increase to their maximum magnitudes at 75 m and a decline to less than a few percent of their maxima at 150 m. The ALF assessments of the Chl-a concentration were 0.18 and 0.48 µg/l, in the samples from 2 and 75 m, respectively. No PE3 fluorescence was detected at this location indicating an absence of cryptophytes in the phytoplankton population, as was consistently observed in the offshore waters of the California current. The spectrally-corrected variable fluorescence, $F_v/F_m$, gradually increased from 0.19 at 5 m depth to 0.3 at 95 m below the Chl-a maximum, and no photosynthetically active Chl-a was detected by the SDC analysis at 150 m. The low $F_v/F_m$ magnitudes indicated a generally depressed photo-physiological status of phytoplankton despite the relatively high Chl-a concentration in the Chl-a peak. The CDOM content indexed by the $I_{CDOM/R}^v$ parameter showed no significant change in the upper 50 m of the water column, a 2-fold gradual increase between 50 and 150 m, and a slower rise with depths between 150 and 500 m (ALF measurements of the 500 m sample are not shown). The $I_{R1/R}^v$, $I_{R2/R}^v$, and $I_{R3/R}^v$ magnitudes, which quantify the broadband red fluorescence typically observed below the Chl-a maximum (see, e.g., FIG. 5E), exhibited a significant increase at 50-150 m, consistent with the above hypothesis that it may be due to fluorescence of a degrading pigment photosystem. Contrary to the CDOM emission, a further gradual decline in the $I_{R1/R}^v$, $I_{R2/R}^v$, and $I_{R3/R}^v$ magnitudes was typically observed below the bottom of the euphotic layer (i.e., below 150-200 m in FIG. 11A).

In the coastal zone of the South California Bight near Point Conception, most SDC-retrieved fluorescent parameters reached their peak magnitudes at much shallower depths, e.g. 15-20 m (FIG. 11B). Significantly higher surface and peak magnitudes of Chl-a concentration, e.g. 2.74 and 7.18 µg/l, respectively, were detected. The intense $F_{PE3}$ fluorescence, with the peak value of the cryptophyte-specific parameter $I_{PE3/R}^g$ as high as 0.47, was observed in the water samples thus indicating significant cryptophyte abundance at this location (confirmed by the HPLC analysis). Though the $I_{PE12/R}^g$ magnitudes indexing the cyanobacterial biomass were somewhat higher compared to the offshore cast samples, the low, ~0.03, $I_{PE12/Chla}$ values indicated a relatively small fraction of cyanobacteria in the coastal phototrophic population. The vertical distribution of variable fluorescence, $F_v/F_m$, showed a slow gradual rise with depth from 0.3 at the surface to 0.38 at 30 m followed by decline to 0.2 at 51 m. Similar to the offshore profile, the $F_v/F_m$ peak was located somewhat deeper than the maximum of the pigment biomass (30 vs. 15 m, respectively). By contrast to the offshore measurements, the CDOM fluorescence profile, 1 was more uniform. It reached its peak in the pigment maximum at 15 m followed by a gradual, approximately 30% decline between 15 and 50 m. The green-induced red fluorescence, peaking at 644 nm and indexed by the $I_{R2/R}^g$ magnitudes, showed the vertical profile correlated well with the cryptophyte-specific PE fluorescence indexed by $I_{PE3/R}^g$. The vertical profile of another green-induced red emission fluorescence, peaking at 662 nm and indexed by $I_{R3/R}^g$ parameter, was rather correlated with the vertical distribution of the cyanobacterial high PUB/PEB PE fluorescence, $I_{PE12/R}^g$. The observed patterns suggest that the red emission consistently detected in the $LSE^g$ signatures around 644 nm and 662 nm can be associated in these PBP-rich coastal waters with in vivo fluorescence of phycocyanin and allophycocyanin, respectively.

Discussion

The described ALF/SDC analytical suite can provide new tools such as for characterization of the fluorescent constituents in liquids, including natural waters, and bioenvironmental monitoring. The ALF can provide a compact, easily transportable and deployable instrument for high-resolution shipboard underway measurements over a range of spatial and temporal scales as well as discrete sample analyses. The ALF technology can take advantage of selective dual-wavelength laser excitation and broadband LSE spectral detection combined with spectrally corrected measurements of variable fluorescence. The SDC LSE analysis allows retrievals of the overlapped emission bands of aquatic constituents and more accurate photo-physiological assessments of photosynthesizing organisms, including more accurate assessments of biomass and abundance of photosynthesizing organisms. The ALF measurements provide real-time information about intensity and spectral variability in Chl-a, phycoerythrin, and CDOM fluorescence. This approach may lead to improved assessments of pigment biomass and CDOM content, indication of structural changes in the phytoplankton community and quantitative assessment of the PBP-containing phytoplankton and cyanobacteria.

The ALF dual-wavelength violet/green laser excitation can provide for assessment of the key fluorescent constituents, including CDOM, Chl-a and PE pigments. The 405 nm excitation is efficient in assaying of CDOM (see, e.g., FIGS. 5A-5F) and variable fluorescence, but is not as suitable for use for PE analysis because of low PE absorption in the violet spectral range. The 532 nm excitation can provide for efficient PE fluorescence stimulation, but yields generally more complex $LSE^g$ signatures (see, e.g., FIGS. 6A-6F). As shown by the initial field deployments, the ALF dual-wavelength excitation also extends the concentration range of Chl-a assessments. For example, the $I_{Chla/R}^v$ parameter measured with 405 nm excitation has yielded quite reasonable assessments of Chl-a concentration during measurements of the dinoflagellate blooms in the York River (>50 mg m$^{-3}$) and in Monterey Bay (>100 mg m$^{-3}$), where the accuracy of the $I_{Chla/R}$g retrievals can be somewhat compromised.

The use of lasers for emission excitation can provide certain advantages over the broadband light emitting diodes or flash lamps such as can be utilized in other field fluorometers. Indeed, as evident from the sample LSE spectra in FIGS. 5A-5F and 6A-6F, WR scattering is an important and often dominant LSE spectral component. With the narrow-band laser stimulation, the ALF has a characteristic, relatively narrow spectral band, which allows its reliable SDC detection and discrimination in the overlapped LSE spectral patterns. The broadband excitation can result in respective broadening of the Raman spectral band, thus significantly complicating its discrimination from the constituent fluorescence. Normalization of the constituent fluorescence to WR scattering can account for the highly variable optical properties of natural waters and can create units that can be directly compared to the data acquired by various shipboard and airborne laser fluorosensors.

As shown by the ALF field measurements, the LSE signatures measured in the diverse water types can represent complex and highly variable patterns formed by the overlapped spectral bands of fluorescent aquatic constituents (see, e.g., FIGS. 5A-5F, and 6A-6F). Because of the spectral overlap, the spectral intensity at the wavelength of the constituent emission in most cases overestimates the actual intensity of the constituent emission. The overestimation is particularly significant in the estuarine, bay and fresh waters known to be spectrally complex (see, e.g., FIGS. 5B, 5C, 5F, 6C and 6E), but it may occur as well in the oceanic waters (see, e.g., FIGS. 5D, 5E, and 6F). Accounting for the spectral overlap can be particularly important for the correct fluorescence assessment of PE pigments (see, e.g., FIGS. 6B, 6C, 6E, and 6F) and water Raman scattering (see, e.g., FIGS. 5B, 5C, 5F, and 6B-F). The SDC LSE analysis can allow for accurate retrievals of the constituent bands, thus providing for improved qualitative and quantitative constituent assessment. Incorporation of the broadband hyperspectral LSE SDC analysis in the shipboard and airborne laser remote sensing and in situ laser measurements can further improve observational capabilities and provide important information about natural aquatic environments over a range of spatial and temporal scales.

Another aspect of the spectral complexity of natural waters concerns the accuracy of photo-physiological assessment of photosynthesizing organisms via measurements of variable fluorescence. As revealed by the ALF field spectral measurements in various water types, the background non-Chl-a emission produced by CDOM and other constituents in the spectral area of Chl-a fluorescence can vary in a range of several percent to a hundred percent of the Chl-a fluorescence intensity. Not accounting for the non-Chl-a fluorescence background can result in significant, such as up to 35-50%, underestimation of the magnitude of variable fluorescence (see, e.g., FIG. 9). The spectrally-corrected photo-physiological assessment of variable fluorescence is another distinct feature of the ALF measurement and analytical protocols that provides for improved characterization of natural aquatic environments.

In turn, the information about the physiological and photo-protective status of photosynthesizing microorganisms retrieved from temporal measurements of Chl-a fluorescence induction can be used to significantly improve the accuracy of spectral retrievals of pigment concentration as shown above (see, e.g., FIG. 12).

Comments

This document describes, among other things, (i) designing a robust compact laser spectrofluorometer capable of routine broadband LSE/PDP measurements in the field, (ii) acquiring a set of field observations representing diverse liquid types, and (iii) the thorough analysis of the laboratory and field ALF measurements to develop the new analytical algorithms. The constituent fluorescence parameters yielded by the SDC algorithms can be converted into commonly accepted units (e.g., constituent concentrations), such as via a series of laboratory and field calibrations. The correlations between the Chl-a fluorescence retrievals and independent assessments of Chl-a concentration look reasonably good. The available field data sets can be analyzed to verify the robustness of the correlation in the extended concentration range and the regional/seasonal dependence of the correlation parameters that can affect the accuracy of the fluorescence retrievals. At the short time scale, the diel variability in the pigment fluorescence yield caused by various physiological photo-protective mechanisms can be accounted for, such as to further improve assessments of Chl-a and PBP concentrations from the shipboard underway flow-through measurements. The ALF measurements of variable fluorescence can provide important feedback to the LSE spectral analysis of Chl-a and PBP fluorescence to account for the photo-physiological variability in the pigment fluorescence yields. The field-based observations of spectral variability in Chl-a fluorescence can provide new means for assaying phytoplankton physiology and functional groups. The detected red emission peaks at 625, 644 and 662 nm can be identified and interpreted to provide additional information about pertinent complex bio-geochemical processes in the natural aquatic environments. Extension of the ALF measurements and the SDC algorithms into the near ultraviolet and infrared spectral range can yield valuable information about other fluorescent constituents, such as spectrally-distinct forms of CDOM and bacteriochlorophyll. Finally, the ALF methods and analytical protocols, which have been tested and employed in the flow-through instrument, can be implemented in a variety of instrument configurations and settings, including in situ and airborne laser fluorosensors, to improve our capacity for oceanographic observations and bioenvironmental monitoring.

TABLE 1

SDC spectral components. Three bands of the water Raman scattering with the Raman shifts $v_{max}$ = 1660, 2200 and 3440 cm$^{-1}$, respectively, are integrated into one SDC component representing the Raman scattering in the LSE spectra. Spectral location of the individual Raman peak can be calculated as $\lambda_{max} = (\lambda_{exc}^{-1} - v_{max})^{-1}$; here, $\lambda_{max}$ and $\lambda_{exc}$ are the wavelengths of the Raman scattering peak and excitation, respectively.

|   | Spectral component | Abbreviation | Emission peak, nm |
|---|---|---|---|
| 1 | Elastic scattering | $E_E^v$ | 405 |
| 2 | CDOM fluorescence | $E_{CDOM}^v$ | 508 |
| 3 | Water Raman scattering, 1660, 2200, and 3440 cm$^{-1}$ | $E_R^v$ | 434, 445, 471 |
| 4 | Elastic scattering | $E_E^g$ | 532 |
| 5 | CDOM fluorescence | $E_{CDOM}^g$ | 587 |
| 6 | Water Raman scattering, 1660, 2200, 3440 cm$^{-1}$ | $E_R^g$ | 583, 602, 651 |
| 7 | Red emission 1 | $E_{R1}$ | 625 |
| 8 | Red emission 2 | $E_{R2}$ | 644 |
| 9 | Red emission 3 | $E_{R3}$ | 662 |
| 10 | Chl-a fluorescence | $E_{C1}$ | 673 |
| 11 | Chl-a fluorescence | $E_{C2}$ | 679 |
| 12 | Chl-a fluorescence | $E_{C3}$ | 693 |
| 13 | PE fluorescence 1 | $E_{PE1}$ | 565 |
| 14 | PE fluorescence 2 | $E_{PE2}$ | 578 |
| 15 | PE fluorescence 3 | $E_{PE3}$ | 589 |

TABLE 2

Parameters of the Pearson's IV function(s) for the analytical approximation of the SDC components of the constituent emission bands observed in natural waters ($E_E^v$ is approximated with $y = a_0 \exp(-a_1 \lambda)$). The superscripts "v" and "g" indicate excitation at 405 and 532 nm, respectively. If several lines of coefficients are listed, the emission band is presented as a sum of the Pearson's functions calculated with the listed coefficients.

| Spectral component | Emission Band | $\lambda_{max}$, nm | $a_0$ | $a_1$ | $a_2$ | $a_3$ | $a_4$ |
|---|---|---|---|---|---|---|---|
| $E_{CDOM}^v$ | CDOM fluorescence | 505 | 1 | 505.2 | 87.7 | 2.22 | −2.85 |
| $E_R^v$ | Water Raman scattering: 1660, 2200, and 3440 cm$^{-1}$ | 471 | 0.025 | 422.3 | 1.49 | 0.413 | −0.988 |
|  |  |  | 0.016 | 434.8 | 1.35 | 0.789 | 0.540 |
|  |  |  | 0.008 | 444.2 | 1.01 | 4.20 | −76.5 |
|  |  |  | 0.619 | 466.7 | 5.11 | 2.68 | −0.539 |
|  |  |  | 0.759 | 471.2 | 6.60 | 3.72 | 0.019 |
|  |  |  | 0.190 | 474.8 | 3.62 | 4.54 | 12.3 |
|  |  |  | 0.019 | 484.5 | 3.27 | 3.60 | −23.3 |
| $E_{CDOM}^g$ | CDOM fluorescence | 583 | 1 | 583.1 | 3.28 | 1.66 | −71.6 |
| $E_R^g$ | Water Raman scattering: 1660, 2200, and 3440 cm$^{-1}$ | 651 | 0.042 | 583.3 | 2.24 | 0.852 | 0.650 |
|  |  |  | 0.016 | 599.2 | 5.47 | 0.724 | −0.710 |
|  |  |  | 0.457 | 641.9 | 7.84 | 2.33 | −0.291 |
|  |  |  | 0.817 | 650.5 | 12.0 | 3.67 | 1.39 |
|  |  |  | 0.169 | 657.9 | 2.87 | 3.35 | 19.6 |
|  |  |  | 0.017 | 672.7 | 16.6 | 14.0 | 83.9 |
| $E_{R1}$ | Red emission 1 | 625 | 1 | 625.1 | 12.1 | 1.59 | −3.11 |
| $E_{R2}$ | Red emission 2 | 644 | 1 | 644.0 | 17.2 | 1.80 | −2.63 |
| $E_{R3}$ | Red emission 3 | 662 | 1 | 661.9 | 23.0 | 1.62 | −1.65 |
| $E_{Ch1}$ | Chl-a fluorescence 1 | 673 | 1 | 673.4 | 13.7 | 2.95 | −0.616 |
| $E_{Ch2}$ | Chl-a fluorescence 2 | 679 | 1 | 678.5 | 12.8 | 1.86 | −0.444 |
| $E_{Ch3}$ | Chl-a fluorescence 3 | 692 | 1 | 692.1 | 16.1 | 2.23 | −2.37 |
| $E_{PE1}$ | PE fluorescence 1 | 565 | 0.985 | 565.4 | 58.1 | 12.3 | −16.9 |
|  |  |  | 0.233 | 610.9 | 35.3 | 1.85 | −2.49 |
| $E_{PE2}$ | PE fluorescence 2 | 578 | 0.954 | 577.9 | 14.1 | 1.14 | −0.78 |
|  |  |  | 0.163 | 613.8 | 70.3 | 8.17 | 7.74 |
| $E_{PE3}$ | PE fluorescence 3 | 590 | 1.000 | 589.8 | 21.0 | 1.56 | −1.40 |
|  |  |  | 0.056 | 617.1 | 14.6 | 3.57 | −1.59 |
|  |  |  | 0.063 | 628.1 | 18.1 | 4.67 | 0.487 |
| $E_E^g$ | Elastic scattering | 532 | 1 | 543.9 | 0.913 | 1.01 | −15.7 |
| $E_E^v$ | Elastic scattering, approximated with $y = a_0 \exp(-a_1 \lambda)$ | 405 | 6.85$^{30}$ | 1.68$^{-1}$ |  |  |  |

Additional Notes & Examples

Example 1 includes subject matter, such as a method, comprising stimulating a liquid, which can include dissolved or particulate matter, such as fluorescent constituents, using a laser, and obtaining a spectral measurement of laser-stimulated emission (LSE) from the liquid sample. Example 1 can include subject matter such as obtaining a temporal measurement of an LSE induction from the liquid sample, and performing spectral deconvolution (SDC) analysis using the spectral measurement. Example 1 can include subject matter such as determining a characteristic of a fluorescent constituent in the liquid sample using information from the SDC analysis and the temporal measurement.

In Example 2, the subject matter of Example 1 can optionally include performing spectral deconvolution (SDC) analysis using linear amplitude scaling of discrete spectral components attributable to constituents present in the liquid.

In Example 3, the subject matter of one or any combination of Examples 1-2 can optionally include determining a characteristic of a fluorescent constituent using information from one of the spectral or temporal measurements to adjust the other of the spectral or temporal measurements.

In Example 4, the subject matter of one or any combination of Examples 1-3 can optionally include stimulating a water volume using the laser, and determining a characteristic of a fluorescent constituent, such as assessing a chlorophyll-a concentration in the water volume.

In Example 5, the subject matter of one or any combination of Examples 1-4 can optionally include assessing a chlorophyll-a concentration by determining a best fit to a waveform indicative of a chlorophyll-a fluorescence induction corrected for a non-chlorophyll background emission, such as using the equation $$[F_m^{-1}-(F_m^{-1}-F_0^{-1})\exp(-t/A)]^{-1}.$$

wherein $F_m$ is a maximum intensity of the chlorophyll fluorescence, $F_0$ is an initial intensity of the chlorophyll fluorescence, t is time, and A is a time constant. Example 5 can include subject matter such as determining a magnitude of variable fluorescence, $F_v/F_m$, by subtracting the initial intensity of the chlorophyll fluorescence, $F_0$, from the maximum intensity of the chlorophyll fluorescence, $F_m$, and normalizing the result to the maximum intensity of the chlorophyll fluorescence, $F_m$, such as using the equation $$F_v/F_m=(F_m-F_o)/F_m.$$

Example 5 can include subject matter such as using the magnitude of variable fluorescence to adjust information received from the spectral deconvolution analysis.

In Example 6, the subject matter of one or any combination of Examples 1-5 can optionally include using the magnitude of variable fluorescence to adjust information received from the spectral deconvolution analysis, such as including normalizing information obtained from the spectral deconvolution analysis to the magnitude of variable fluorescence.

In Example 7, the subject matter of one or any combination of Examples 1-6 can optionally include determining a characteristic of a fluorescent constituent including assessing a chromophoric dissolved organic matter concentration in the liquid.

In Example 8, the subject matter of one or any combination of Examples 1-7 can optionally include stimulating a water volume and determining a characteristic of a fluorescent constituent including assessing a phycobiliprotein, including phycoerythrin, pigment concentration in the water volume.

In Example 9, the subject matter of one or any combination of Examples 1-8 can optionally include determining a characteristic of a fluorescent constituent, including using information from the spectral deconvolution analysis to calculate intensities of constituent-specific fluorescence spectra normalized to Raman scattering, and determining a quantitative assessment of a constituent-specific concentration in the liquid.

In Example 10, the subject matter of one or any combination of Examples 1-9 can optionally include obtaining a temporal measurement of an LSE induction from the liquid in the spectral region of chlorophyll-a fluorescence.

In Example 11, the subject matter of one or any combination of Examples 1-10 can optionally include determining a characteristic of a fluorescent constituent including assessing a photo-physiological status of photosynthesizing microorganisms in the liquid.

In Example 12, the subject matter of one or any combination of Examples 1-11 can optionally include determining a characteristic of a fluorescent constituent including minimizing or eliminating an effect of a non-chlorophyll background emission to improve accuracy of an assessment of a photo-physiological status of phytoplankton based on the temporal measurement.

In Example 13, the subject matter of one or any combination of Examples 1-12 can optionally include stimulating the liquid using a laser configured to emit energy at wavelengths between 200 nm and 800 nm, and obtaining a broadband spectral measurement over a portion of the LSE spectrum in response to the stimulating.

In Example 14, the subject matter of one or any combination of Examples 1-13 can optionally include obtaining a temporal measurement, including obtaining a first waveform, $F_{PDP}(t)$, indicative of a time course of LSE in the spectral area of chlorophyll-a fluorescence.

In Example 15, the subject matter of one or any combination of Examples 1-14 can optionally include determining a characteristic of a fluorescent constituent by determining a best fit to a second waveform using a biophysical modeling function, the second waveform determined using the magnitude of the non-chlorophyll background emission, $B_{NC}$, to adjust the first waveform, $F_{PDP}(t)$, determining a magnitude of variable fluorescence using one or more parameters derived from the biophysical modeling function, and using the magnitude of variable fluorescence and information from the spectral measurement to adjust a quantitative assessment of chlorophyll-a fluorescence retrieved from the spectral deconvolution analysis.

In Example 16, the subject matter of one or any combination of Examples 1-15 can optionally include determining a characteristic of a fluorescent constituent, including determining a magnitude of a non-chlorophyll background emission, $B_{NC}$, in the first waveform using the spectral measurement, determining a second waveform, $F_{Chla}(t)$, indicative of chlorophyll-a fluorescence induction over time, the second waveform determined using the magnitude of the non-chlorophyll background emission, $B_{NC}$, to adjust the first waveform, $F_{PDP}(t)$, determining a magnitude of a variable fluorescence, $F_v/F_m$, using the second waveform, and using the variable fluorescence to assess a photo-physiological status of phytoplankton.

In Example 17, the subject matter of one or any combination of Examples 1-16 can optionally include determining the magnitude of the non-chlorophyll background emission, $B_{NC}$, including determining the LSE spectral intensity around a chlorophyll-a fluorescence peak using the spectral measurement, determining a magnitude of a chlorophyll-a fluorescence band using spectral deconvolution of the spectral measurement, obtaining an intensity of the non-chlorophyll fluorescence in the spectral measurement around the chlorophyll-a fluorescence peak by subtracting the magnitude of the chlorophyll-a fluorescence from a portion of the spectral measurement around the chlorophyll-a fluorescence peak, calculating a ratio, $I_{NC/Chla}$, of the intensity of the non-chlorophyll fluorescence in the spectral measurement around the chlorophyll-a fluorescence peak to the magnitude of the chlorophyll-a fluorescence band, and determining the magnitude of the non-chlorophyll background emission, $B_{NC}$, such as using the equation:

$$B_{NC}=(1+I_{NC/Chla}^{-1})^{-1}\mathrm{mean}(F_{PDP}(t)).$$

In Example 18, the subject matter of one or any combination of Examples 1-17 can optionally include determining a magnitude of a chlorophyll-a fluorescence band using spectral deconvolution, including fitting scaled amplitudes of discrete spectral components of fluorescent constituents to the spectral measurement.

In Example 19, the subject matter of one or any combination of Examples 1-18 can optionally include using variable fluorescence to assess a photo-physiological status of phytoplankton, including determining a best fit to the second waveform using the equation:

$$[F_m^{-1}-(F_m^{-1}-F_o^{-1})\exp(-t/A)]^{-1},$$

wherein $F_m$ is a maximum intensity of the chlorophyll fluorescence, $F_0$ is an initial intensity of the chlorophyll fluorescence, t is time, and A is a time constant.

In Example 20, the subject matter of one or any combination of Examples 1-19 can optionally include determining the magnitude of a variable fluorescence, $F_v/F_m$, by subtracting the initial intensity of the chlorophyll fluorescence, $F_0$, from the maximum intensity of the chlorophyll fluorescence, $F_m$, and normalizing the result to the maximum intensity of the chlorophyll fluorescence, $F_m$:

$$F_v/F_m=(F_m-F_o)/F_m.$$

Example 21 can include, or can be combined with the subject matter of one or any combination of Examples 1-20 to optionally include subject matter such as a system, comprising a laser configured to stimulate a liquid, a first measurement circuit configured to obtain a spectral measurement of laser-stimulated emission (LSE) from the liquid, a second measurement circuit configured to obtain a temporal measurement of an LSE time course from the liquid, and a processor circuit, configured to control the first and second measurement circuits, and configured to compute an assessment of a fluorescent substance in the liquid using information from one of the spectral or temporal measurements to adjust the other of the spectral or temporal measurements.

In Example 22, the subject matter of one or any combination of Examples 1-21 can optionally include a processor circuit configured to compute a non-chlorophyll background fluorescence in the liquid to improve accuracy of the temporal measurements.

In Example 23, the subject matter of one or any combination of Examples 1-22 can optionally include a processor circuit configured to perform spectral deconvolution analysis using information received from the first measurement circuit to determine a magnitude of a constituent-specific fluorescence band, the spectral deconvolution including fitting scaled amplitudes of discrete spectral components of fluorescent constituents to a portion of the information received from the first measurement circuit.

Example 24 can include, or can be combined with the subject matter of one or any combination of Examples 1-23 to optionally include subject matter such as a method, comprising stimulating a water volume, which includes fluorescent constituents, using a laser; obtaining a spectral measurement of laser-stimulated emission (LSE) from the water volume, obtaining a temporal measurement of an LSE induction from the water volume, performing spectral deconvolution (SDC) analysis of LSE to assess individual fluorescent constituents, including pigments and organic matter, computing a photo-physiological status of phytoplankton using information from the spectral deconvolution (SDC) analysis to improve accuracy of the temporal measurement, and computing a pigment concentration using information from the spectral deconvolution (SDC) analysis and the photo-physiological status information.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is::

1. A method, comprising:
stimulating a liquid, which includes dissolved and particulate matter, using a laser;
obtaining a spectral measurement of a laser-stimulated emission (LSE) from the liquid;
obtaining a temporal measurement of a LSE from the liquid; and
determining a characteristic of a fluorescent constituent in the liquid, the determining using information from the temporal measurement of the LSE to adjust the spectral measurement of the LSE.

2. The method of claim 1, further comprising performing spectral deconvolution (SDC) analysis using the spectral measurement of the LSE, wherein the determining the characteristic of the fluorescent constituent in the liquid includes using information from the temporal measurement of the LSE to adjust information from the SDC analysis.

3. The method of claim 2, wherein the performing spectral deconvolution (SDC) analysis includes linear amplitude scaling of discrete spectral components attributable to fluorescent constituents present in the liquid.

4. The method of claim 2, wherein the determining a characteristic of a fluorescent constituent includes using information from the SDC analysis to adjust information from the temporal measurement.

5. The method of claim 2, wherein the determining a characteristic of a fluorescent constituent includes:
using information from the SDC analysis to calculate intensities of constituent-specific fluorescence spectra normalized to Raman scattering; and
determining a quantitative assessment of a constituent-specific concentration in the liquid.

6. The method of claim 1, wherein the stimulating a liquid includes stimulating a water volume, and wherein the determining a characteristic of a fluorescent constituent includes assessing a chlorophyll-a concentration in the water volume.

7. The method of claim 6, wherein the assessing a chlorophyll-a concentration includes:
determining a best fit equation to a waveform indicative of a chlorophyll-a fluorescence induction corrected for a non-chlorophyll background emission, the equation including parameters representative of a maximum intensity of the chlorophyll fluorescence, an initial intensity of the chlorophyll fluorescence, and time;
determining a magnitude of variable fluorescence by subtracting the initial intensity of the chlorophyll fluorescence from the maximum intensity of the chlorophyll fluorescence, and normalizing the result to the maximum intensity of the chlorophyll fluorescence; and
using the magnitude of variable fluorescence to adjust information from the spectral measurement.

8. The method of claim 7, wherein the using the magnitude of variable fluorescence to adjust information from the spectral measurement includes normalizing information from the spectral measurement to the magnitude of variable fluorescence.

9. The method of claim 1, wherein the determining a characteristic of a fluorescent constituent includes assessing a chromophoric dissolved organic matter concentration in the liquid.

10. The method of claim 1, wherein the stimulating a liquid includes stimulating a water volume, and wherein the determining a characteristic of a fluorescent constituent includes assessing a phycobiliprotein, including phycoerythrin, pigment concentration in the water volume.

11. The method of claim 1, wherein the obtaining a temporal measurement of the LSE from the liquid includes obtaining a temporal measurement of a LSE from the liquid in the spectral region of chlorophyll-a fluorescence.

12. The method of claim 1, wherein the determining a characteristic of a fluorescent constituent includes assessing a photo-physiological status of photosynthesizing microorganisms in the liquid.

13. The method of claim 1, wherein the determining a characteristic of a fluorescent constituent includes minimizing or eliminating an effect of a non-chlorophyll background emission to improve accuracy of an assessment of a photo-physiological status of phytoplankton based on the temporal measurement.

14. The method of claim 1, wherein the stimulating the liquid using a laser includes using a laser configured to emit energy at wavelengths between 200 nm and 800 nm; and
wherein the obtaining the spectral measurement includes obtaining a broadband spectral measurement over a portion of the LSE spectrum in response to the stimulating.

15. The method of claim 1, wherein the obtaining a temporal measurement includes obtaining a first waveform indicative of a time course of a LSE in the spectral area of chlorophyll-a fluorescence.

16. The method of claim 15, wherein the determining a characteristic of a fluorescent constituent includes:
determining a best fit equation to a second waveform using a biophysical modeling function, the second waveform determined using a magnitude of a non-chlorophyll background emission to adjust the first waveform;
determining a magnitude of variable fluorescence using one or more parameters derived from the biophysical modeling function; and
using the magnitude of variable fluorescence and information from the spectral measurement to adjust a quantitative assessment of chlorophyll-a fluorescence retrieved from a result of spectral deconvolution analysis of the spectral measurement of the LSE.

17. The method of claim 15, wherein the determining a characteristic of a fluorescent constituent includes:
determining a magnitude of a non-chlorophyll background emission in the first waveform using the spectral measurement;
determining a second waveform indicative of chlorophyll-a fluorescence induction over time, the second waveform determined using the magnitude of the non-chlorophyll background emission to adjust the first waveform;
determining a magnitude of a variable fluorescence using the second waveform; and
using the variable fluorescence to assess a photo-physiological status of phytoplankton.

18. The method of claim 17, wherein the determining the magnitude of the non-chlorophyll background emission includes:
determining the LSE spectral intensity around a chlorophyll-a fluorescence peak using the spectral measurement;
determining a magnitude of a chlorophyll-a fluorescence band using spectral deconvolution analysis of the spectral measurement of the LSE;
obtaining an intensity of the non-chlorophyll fluorescence in the spectral measurement around the chlorophyll-a fluorescence peak by subtracting the magnitude of the chlorophyll-a fluorescence from a portion of the spectral measurement around the chlorophyll-a fluorescence peak;

calculating a ratio of the intensity of the non-chlorophyll fluorescence in the spectral measurement around the chlorophyll-a fluorescence peak to the magnitude of the chlorophyll-a fluorescence band; and determining the magnitude of the non-chlorophyll background emission using the ratio and the second waveform.

19. The method of claim 18, wherein the determining a magnitude of a chlorophyll-a fluorescence band using spectral deconvolution analysis includes fitting scaled amplitudes of discrete spectral components of fluorescent constituents to the spectral measurement.

20. The method of claim 17, wherein using the variable fluorescence to assess a photo-physiological status of phytoplankton includes determining a best fit equation to the second waveform, the equation including parameters representative of a maximum intensity of the chlorophyll fluorescence, an initial intensity of the chlorophyll fluorescence, and time.

21. The method of claim 20, including determining the magnitude of a variable fluorescence by subtracting the initial intensity of the chlorophyll fluorescence from the maximum intensity of the chlorophyll fluorescence, and normalizing the result to the maximum intensity of the chlorophyll fluorescence.

22. A system, comprising:
a laser configured to stimulate a liquid;
a first measurement circuit configured to obtain a spectral measurement of laser-stimulated emission (LSE) from the liquid;
a second measurement circuit configured to obtain a temporal measurement of a LSE time course from the liquid; and
a processor circuit, configured to control the first and second measurement circuits, and configured to compute an assessment of a fluorescent substance in the liquid using information from the temporal measurement to adjust the spectral measurement.

23. The system of claim 22, wherein the processor circuit is configured to compute a non-chlorophyll background fluorescence in the liquid to improve accuracy of the temporal measurement.

24. The system of claim 22, wherein the processor circuit is configured to perform spectral deconvolution analysis using information received from the first measurement circuit to determine a magnitude of a constituent-specific fluorescence band, the spectral deconvolution including fitting scaled amplitudes of discrete spectral components of fluorescent constituents to a portion of the information received from the first measurement circuit.

25. A method, comprising:
stimulating a water volume, which includes fluorescent constituents, using a laser;
obtaining a spectral measurement of laser-stimulated emission (LSE) from the water volume;
obtaining a temporal measurement of a LSE from the water volume;
performing spectral deconvolution (SDC) analysis of the spectral measurement to assess individual fluorescent constituents, including pigments and organic matter;
computing a photo-physiological status of phytoplankton using information from the temporal measurement to improve accuracy of the spectral deconvolution (SDC) analysis; and
computing a pigment concentration using information from the spectral deconvolution (SDC) analysis and the photo-physiological status information.

* * * * *